(12) United States Patent
Hans et al.

(10) Patent No.: US 10,047,034 B2
(45) Date of Patent: Aug. 14, 2018

(54) POLYHYDROXYLATED PENTACYCLIC TRITERPENE ACIDS AS HMG-COA REDUCTASE INHIBITORS

(71) Applicants: Joachim Hans, Holzminden (DE); Torsten Grothe

(72) Inventors: Joachim Hans, Holzminden (DE); Kathrin Reinhardt, Münster (DE); Torsten Grothe, Affoltern am Albis (CH); Ingo Wöhrle, Dortmund (DE); Jana Moldenhauer, Dortmund (DE); Bärbel Köpcke, Dortmund (DE); Thomas Küper, Reken (DE); Jens Bitzer, Dortmund (DE)

(73) Assignee: Prairie Berry Europe GmbH, Hannover (DE)

( * ) Notice: Subject to any disclaimer, the term of this patent is extended or adjusted under 35 U.S.C. 154(b) by 0 days.

(21) Appl. No.: 14/401,699

(22) PCT Filed: May 7, 2013

(86) PCT No.: PCT/EP2013/059513
§ 371 (c)(1),
(2) Date: Nov. 17, 2014

(87) PCT Pub. No.: WO2013/171100
PCT Pub. Date: Nov. 21, 2013

(65) Prior Publication Data
US 2015/0133552 A1    May 14, 2015

Related U.S. Application Data

(60) Provisional application No. 61/647,617, filed on May 16, 2012.

(51) Int. Cl.

| | | |
|---|---|---|
| *A01N 37/00* | (2006.01) |
| *A61K 31/19* | (2006.01) |
| *C07C 62/32* | (2006.01) |
| *A61K 45/06* | (2006.01) |
| *A61K 31/01* | (2006.01) |
| *A61K 31/015* | (2006.01) |
| *A61K 31/191* | (2006.01) |
| *A61K 31/192* | (2006.01) |

(Continued)

(52) U.S. Cl.
CPC .............. *C07C 62/32* (2013.01); *A21D 2/165* (2013.01); *A21D 2/36* (2013.01); *A21D 8/047* (2013.01); *A23C 9/133* (2013.01); *A23C 9/1315* (2013.01); *A23C 9/1322* (2013.01); *A23C 9/156* (2013.01); *A23C 9/1565* (2013.01); *A23C 11/02* (2013.01); *A23C 15/16* (2013.01); *A23D 7/0056* (2013.01); *A23G 9/32* (2013.01); *A23L 2/39* (2013.01); *A23L 2/40* (2013.01); *A23L 2/52* (2013.01); *A23L 7/126* (2016.08); *A23L 27/10* (2016.08); *A23L 27/60* (2016.08); *A23L 33/105* (2016.08); *A61K 9/0007* (2013.01); *A61K 9/2018* (2013.01); *A61K 9/2027* (2013.01); *A61K 9/485* (2013.01); *A61K 9/4866* (2013.01); *A61K 9/4891* (2013.01); *A61K 31/01* (2013.01); *A61K 31/015* (2013.01); *A61K 31/191* (2013.01); *A61K 31/192* (2013.01); *A61K 31/352* (2013.01); *A61K 31/7048* (2013.01); *A61K 36/73* (2013.01); *A61K 45/06* (2013.01); *A61K 47/26* (2013.01); *A61K 47/46* (2013.01); *A23C 2260/152* (2013.01); *A61K 9/0095* (2013.01)

(58) Field of Classification Search
CPC ... A23C 11/02; A23C 15/16; A23C 2260/152; A23C 9/1315; A23C 9/1322; A23C 9/133; A23C 9/156; A23C 9/1565; A23L 1/1643; A23L 1/221; A23L 1/24; A23L 1/3002; A23L 2/39; A23L 2/40; A23L 2/52
See application file for complete search history.

(56) References Cited

U.S. PATENT DOCUMENTS

2009/0028959 A1* 1/2009 Li .......................... A61K 31/56
424/569

FOREIGN PATENT DOCUMENTS

WO    WO 2010143058 A1 * 12/2010

OTHER PUBLICATIONS

Zhang et al, Cardiovasc. Drugs Ther. (2006) 20:349-357.*

(Continued)

*Primary Examiner* — Jean P Cornet
(74) *Attorney, Agent, or Firm* — Edward E. Sowers; Brannon Sowers & Cracraft PC

(57) ABSTRACT

The present invention relates to certain polyhydroxylated pentacyclic triterpene acids of formula (I) for use as HMG-CoA reductase inhibitors in the prophylactic and/or therapeutic treatment of a disease, disorder or condition that responds to a reduction of the HMG-CoA reductase activity in a mammal, preferably a human being. The present invention further relates to certain mixtures and plant extracts comprising euscaphic acid and tormentic acid, wherein the amount of euscaphic acid to tormentic acid exceeds a certain ratio. Further, the present invention also relates to a formulation, preferably pharmaceutical or nutraceutical formulation, comprising one or more of said compounds of formula (I), a composition according to the present invention or a plant extract according to the present invention. Also, the present invention relates to a process for obtaining certain polyhydroxylated pentacyclic triterpene acids of formula (I), a composition according to the present invention or a plant extract according to the present invention.

8 Claims, No Drawings

(51) Int. Cl.

| | |
|---|---|
| *A61K 31/352* | (2006.01) |
| *A61K 31/7048* | (2006.01) |
| *A61K 36/73* | (2006.01) |
| *A61K 9/46* | (2006.01) |
| *A61K 47/26* | (2006.01) |
| *A61K 47/46* | (2006.01) |
| *A61K 9/20* | (2006.01) |
| *A61K 9/48* | (2006.01) |
| *A23C 9/13* | (2006.01) |
| *A23C 9/133* | (2006.01) |
| *A23C 9/156* | (2006.01) |
| *A23C 11/02* | (2006.01) |
| *A23C 15/16* | (2006.01) |
| *A23L 2/39* | (2006.01) |
| *A23L 2/40* | (2006.01) |
| *A23L 2/52* | (2006.01) |
| *A23G 9/32* | (2006.01) |
| *A21D 2/16* | (2006.01) |
| *A21D 2/36* | (2006.01) |
| *A21D 8/04* | (2006.01) |
| *A23D 7/005* | (2006.01) |
| *A23L 7/126* | (2016.01) |
| *A23L 27/10* | (2016.01) |
| *A23L 27/60* | (2016.01) |
| *A23L 33/105* | (2016.01) |
| *A61K 9/00* | (2006.01) |

(56) References Cited

OTHER PUBLICATIONS

JB, Drugs Aging. 2004;21(9):583-95.*
O'Leary, A First Course in Mathematical Logic and Set Theory 2016.*

* cited by examiner

POLYHYDROXYLATED PENTACYCLIC TRITERPENE ACIDS AS HMG-COA REDUCTASE INHIBITORS

CROSS-REFERENCES TO RELATED APPLICATIONS

This application is a National Stage filing of International Application PCT/EP 2013/059513, filed May 7, 2013, entitled "POLYHYDROXYLATED PENTACYCLIC TRITERPENE ACIDS AS HMG-COA REDUCTASE INHIBITORS". The subject application claims priority to PCT/EP 2013/059513, and U.S. Provisional Application 61/647,617 filed May 16, 2012, incorporates all by reference herein, in their entirety.

BACKGROUND OF THE INVENTION

The present invention relates to certain polyhydroxylated pentacyclic triterpene acids of formula (I), particularly of formula (I-A), defined hereinafter for use as HMG-CoA reductase inhibitors in the prophylactic and/or therapeutic treatment of a disease, disorder or condition that responds to a reduction of the HMG-CoA reductase activity in a mammal, preferably a human being. The present invention further relates to certain mixtures and plant extracts comprising euscaphic acid and tormentic acid, wherein the amount of euscaphic acid to tormentic acid exceeds a certain ratio. Further, the present invention also relates to a formulation, preferably pharmaceutical or nutraceutical formulation, comprising one or more of said compounds of formula (I), a composition according to the present invention or a plant extract according to the present invention. Also, the present invention relates to a process for obtaining certain polyhydroxylated pentacyclic triterpene acids of formula (I), a composition according to the present invention or a plant extract according to the present invention.

Cholesterol is mainly an issue because blood total cholesterol and low density lipoprotein correlate strongly with coronary heart disease. Cholesterol homeostasis is maintained by a complex mechanism of sterol absorption, anabolism, catabolism and excretion.

Hypocholesteremic agents, i.e. agents that lower the (plasma) cholesterol level by influencing the cholesterol metabolism, are considered to be beneficial for the health of mammals, in particular human beings. For example, by avoiding an increase in arterial cholesterol and preferably by lowering the plasma cholesterol level, the formation of precursors of fatty streak, an early lesion in the atherosclerotic process, may beneficially be influenced. Cholesterol metabolism is complex and hitherto several different approaches using different pathways have been proposed to positively influence the (plasma) cholesterol level in mammals and avoid or reduce hypercholesterolemia, foam cells, fatty streak, atherosclerotic lesion, atheroma and ultimately atherosclerosis.

Generally speaking, cholesterol-lowering functional foods and nutraceuticals may be classified into several different types, mainly based on their respective mechanistic activity. These mechanistic types include intestinal acyl-CoA:cholesterol acyltransferase (ACAT) inhibitors, 3-hydroxy-3-methylglutaryl (HMG-CoA) reductase inhibitors, LDL receptor up-regulators, bile acid reabsorption inhibitors, and cholesterol-7α-hydroxylase (CYP7A1) activators.

For example, grape seed proanthocyanidin extract is reportedly cholesterol-lowering nutraceutical. The hypocholesterolemic activity of grape seed proanthocyanidin is probably mediated by enhancement of bile acid excretion and up-regulation of CYP7A1.

HMG-CoA reductase (3-Hydroxy-3-Methyl-Glutaryl-CoA reductase; enzyme commission designation EC 1.1.1.88) is the rate-controlling enzyme of the mevalonate pathway, the metabolic pathway that produces cholesterol in mammals. Normally, in mammalian cells this enzyme is suppressed by cholesterol derived from the internalization and degradation of low density lipoprotein (LDL, the "bad" cholesterol) via the LDL receptor as well as oxidized species of cholesterol. Competitive inhibitors of the reductase induce the expression of LDL receptors in the liver, which in turn increases the catabolism of plasma LDL and lowers the plasma concentration of cholesterol, an important determinant of atherosclerosis. HMG-CoA reductase is anchored in the membrane of the endoplasmic reticulum.

HMG-CoA reductase is a polytopic, transmembrane protein that catalyzes a key step in the mevalonate pathway, which is inter alia involved in the synthesis of sterols. In mammals, in particular in human beings, the step involving HMG-CoA reductase in the metabolic pathway of the cholesterol synthesis is rate-limiting and therefore represents a major drug target for contemporary cholesterol-lowering drugs. The medical significance of HMG-CoA reductase has continued to expand beyond its direct role in cholesterol synthesis following the discovery that it can offer cardiovascular health benefits independent of cholesterol reduction.

Statins are used to lower serum cholesterol levels as a means of reducing the risk for cardiovascular disease by potently inhibiting the enzyme HMG-CoA reductase, which plays a central role in the production of cholesterol in the liver. Increased cholesterol levels have been associated with cardiovascular diseases, and statins are therefore used in the prevention of these diseases. Statins are very effective for treating cardiovascular disease, with questionable benefit in those without previous cardiovascular disease but with elevated cholesterol levels. Statins are currently the most widely used drugs for prevention and treatment of atherosclerosis. However, statins are reported to have adverse side effects such as hepatotoxicity, muscle pain, kidney damage and weakness.

Statins include for example rosuvastatin, lovastatin, atorvastatin, pravastatin, fluvastatin and simvastatin. Several cholesterol-lowering statins are naturally occurring. Red yeast rice contains statins known as monacolins, including mevastatin and the highly active lovastatin; the latter can also be found in oyster mushrooms.

Acyl-CoA: cholesterol acyltransferase [ACAT; also referred to as sterol O-acyltransferase (SOAT); enzyme commission designation EC 2.3.1.26] catalyzes the acylation of cholesterol to cholesteryl ester with long chain fatty acids and ACAT inhibition is also an useful strategy for treating hypercholesterolemia or atherosclerosis. It has rather recently been revealed that ACAT exists in the form of two isozymes, namely ACAT 1 (expressed in many cells and tissues) and ACAT 2 (expressed specifically in the small intestine and liver), which have different in vivo functions from each other. For example, ursolic acid, oleanolic acid, and betulinic acid, e.g. obtainable from the methanol extracts of the leaves of *Lycopus lucidus*, are ACAT-inhibitors. Betulinic acid has been described in the literature as potent inhibitor of human ACAT 1 and human ACAT 2.

Other drugs, like ezetimibe, lower the cholesterol level by decreasing cholesterol absorption in the intestine. These may be used alone or together in combination with statins (e.g., ezetimibe and simvastatin).

DETAILED DESCRIPTION OF THE INVENTION

HMG-CoA reductase inhibitors are also expected to lower LDL) levels and increase high density lipoprotein (HDL; the "good" cholesterol) levels.

Various actives for lowering LDL and/or increasing HDL levels, and for treating hypercholesterolemia as well as HMG-CoA reductase inhibitors have been described in the prior art.

WO 01/80870 A1 relates to compositions derived from cranberry and grapefruit for treating or preventing cancer and hypercholesterolemia in a subject.

WO 2005/069844 describes formulations comprising a processed *Morinda citrifolia* product for inhibiting HMG-CoA reductase, for reducing LDL levels and for increasing HDL levels.

US 2005/0171140 A1 suggests certain compounds having a pyridine ring as HMG-CoA reductase inhibitors, for lowering LDL and/or increasing HDL levels, and for treating hypercholesterolemia and atherosclerosis.

U.S. Pat. No. 6,143,755 discloses pharmaceutical compositions and methods of treatment using a combination of ACAT inhibitors and statins as HMG-CoA reductase inhibitors, thereby obtaining a greater reduction of plasma VLDL (very low density lipoprotein) and LDL cholesterol, and an increase in HDL cholesterol.

WO 2011/085979 A1 discloses that certain tricyclic sesquiterpenes obtainable from *Cynara scolymus*, in particular cynaropicrin, are useful for improving the total cholesterol HDL/LDL ratio.

WO 2011/147028 A2 proposes the use of quercetin-rich apple skin extracts for inhibiting oxidation of LDL, reducing cholesterol levels and for treating atherosclerosis. It is also observed in WO 2011/147028 A2 that a triterpene-rich apple peel extract comprising ursolic acid and corosolic acid did not beneficially influence the serum lipid profile and was found to even increase the total cholesterol level relative to the atherogenic control group (fed with diet comprising 0.15 wt. % of cholesterol).

There remains a need for new safe and effective compounds, compositions and formulations for treating, prophylactically and/or therapeutically, diseases, disorders or conditions that responds to a reduction of the HMG-CoA reductase activity in a mammal, particularly a human being.

DETAILED DESCRIPTION OF THE INVENTION

Thus, the primary object of the present invention is to provide one or more alternative HMG-CoA reductase inhibitors, preferably structurally differing from the class of known statin drugs. These alternative HMG-CoA reductase inhibitors should be active in the treatment of diseases, disorders or conditions that respond to a reduction of the HMG-CoA reductase activity in a mammal, said disease, disorder or condition preferably being a cholesterol disorder, preferably selected from the group consisting of hypercholesterolemia, low HDL levels, high LDL levels, arteriosclerosis, and atherosclerosis (=arteriosclerotic vascular disease). Said active ingredients should preferably be naturally occurring.

Surprisingly, it has now been found that a certain group of compounds, namely the polyhydroxylated pentacyclic triterpene acids of formula (I) as defined herein and the physiologically acceptable salts thereof, have the property to inhibit (i.e. reduce the activity of) mammalian HMG-CoA reductase, in particular human HMG-CoA reductase. They are thus useful in the (prophylactic and/or therapeutic) treatment of diseases, disorders or conditions that respond to a reduction of the HMG-CoA reductase activity in a mammal, preferably a human being.

Further, our experimental data also indicate that an improved HDL/LDL ratio, typically a HDL/LDL-ratio of greater than 1, is achievable by administering one or more of the polyhydroxylated pentacyclic triterpene acids of formula (I) as defined herein and the physiologically acceptable salts thereof. In contrast to the atherogenic LDL, HDL is considered to act cardio-protective. Usually, a high HDL/LDL ratio (preferred is a ratio>1, i.e. a higher level of HDL than LDL is desired) is considered a beneficial blood parameter.

In a first embodiment, the invention relates to a compound of formula (I)

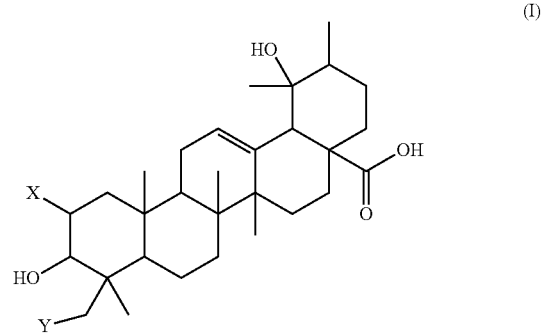

(I)

wherein
X denotes H or OH,
Y denotes H or OH,
or a pharmaceutically acceptable salt thereof,
or mixture of two or more compounds of formula (I), or extract comprising one or more compounds of formula (I) or a pharmaceutically acceptable salt thereof,
for use as HMG-CoA reductase inhibitor in the prophylactic and/or therapeutic treatment of a disease, disorder or condition that responds to a reduction of the HMG-CoA reductase activity in a mammal, preferably a human being.

Preferably, one, several, or all compounds of formula (I) correspond to formula (I-A)

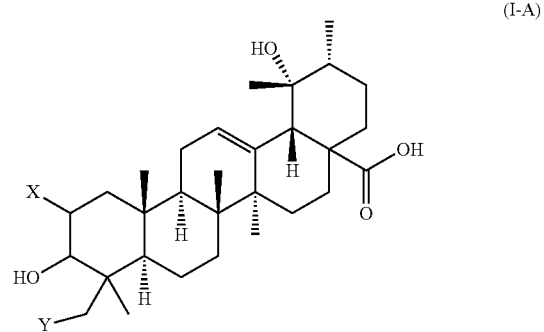

(I-A)

wherein

X denotes H or OH,

Y denotes H or OH, or a pharmaceutically acceptable salt thereof.

In preferred embodiments of the compounds of formula (I) or formula (I-A), X denotes H and Y denotes H; or X denotes H and Y denotes OH; or X denotes OH and Y denotes H; or X denotes OH and Y denotes OH.

In preferred embodiments, the compounds of formula (I) or formula (I-A) contain a total of 2, 3 or 4 hydroxyl groups.

The effects and preferred embodiments described in the context of the present invention particularly are observed and apply for the compounds of formula (I-A).

More specifically, the present invention is based on certain prophylactically and/or therapeutically uses of one or more compounds of formula (I-A), or the physiologically acceptable salts thereof. These compounds are known to be naturally occurring and have been described as such and as being obtainable from several plant materials (details are disclosed hereinbelow).

Preferred compounds of formula (I-A) (for use) according to the present invention are shown in the following Table:

Name (Synonyms) [CAS Registry Number]

Pomolic acid
(Benthamic acid, Randialic acid A)
[CAS RN: 13849-91-7]

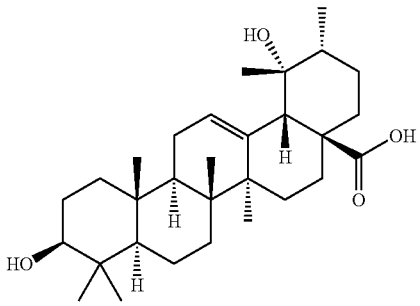

Barbinervic acid
[CAS RN: 64199-78-6]

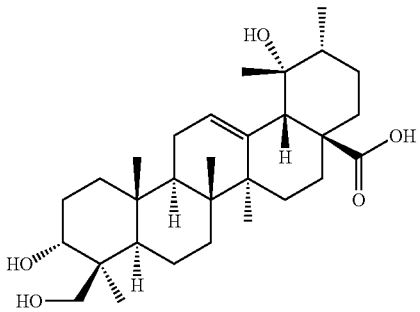

Tormentic acid
[CAS RN: 13850-16-3]

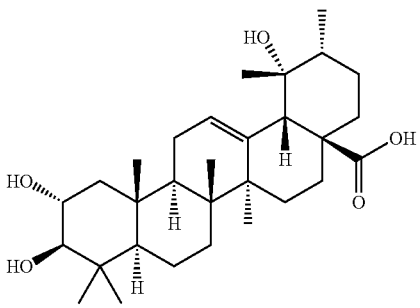

Euscaphic acid
(Acuminatic acid, Jacarandic acid)
[CAS RN: 53155-25-2]

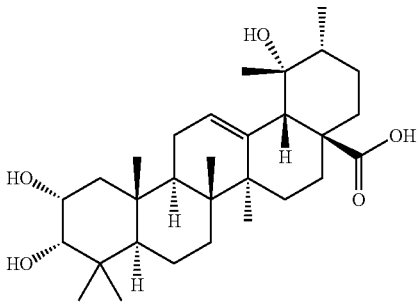

| Name (Synonyms) [CAS Registry Number] | |
|---|---|
| Myrianthic acid<br>[CAS RN: 89786-84-5] | 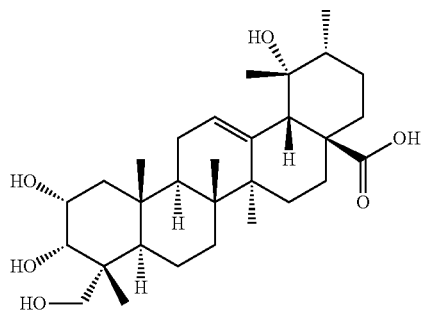 |
| Rotundic acid<br>(Ilexolic acid A)<br>[CAS RN: 20137-37-5] | 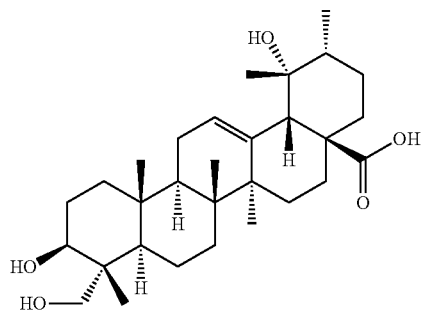 |

Thus, the present invention more specifically relates to a compound or mixture for use as defined above, wherein one, several, or all compounds of formula (I) are selected from the group consisting of pomolic acid, barbinervic acid, tormentic acid, euscaphic acid, and myrianthic acid and the pharmaceutically acceptable salt thereof.

The most preferred compound of formula (I) and the physiologically acceptable salts thereof (for use) according to the present invention is euscaphic acid and mixtures comprising euscaphic acid. In the course of our own investigations it was found that euscaphic acid exhibited the strongest HMG-CoA reductase inhibiting activity of the compounds of formulae (I) and (I-A), and at very low concentrations. Thus, the use of euscaphic acid and the physiologically acceptable salts thereof is particularly preferred in the context of the present invention.

Preferred are therefor also mixtures comprising euscaphic acid or a physiologically acceptable salt of euscaphic acid, and one, preferably two or more, other compounds of formula (I) or the physiologically acceptable salts thereof, wherein the total amount of euscaphic acid and its physiologically acceptable salts is greater than 50 wt. %, more preferably 60 wt. % or more, more preferably 65 wt. % or more, and particularly preferably 70 wt. % or more, in each case based on the total amount by weight of the compounds of formula (I) in said mixture. Preferably, the total amount of euscaphic acid and its physiologically acceptable salts is in the range of 60 to 90 wt. %, more preferably in the range of 65 to 85 wt. %, and particularly preferably in the range of 70 to 80 wt. %, in each case based on the total amount by weight of compounds of formula (I) in said mixture.

For purposes of quantification of the amounts of compounds of formula (I) herein it is emphasized that these amounts include the physiologically acceptable salts of compounds of formula (I) optionally present in a mixture, plant extract, composition or formulation according to the present invention (each as defined herein), said physiologically acceptable salts however being calculated as "free" acid compounds of formula (I), thus disregarding any counterion present in physiologically acceptable salts of compounds of formula (I).

A mixture for use according to the present invention preferably comprises euscaphic acid and tormentic acid, wherein preferably the ratio of euscaphic acid to tormentic acid by weight is greater than 1:1, more preferably equal to or greater than 2:1, more preferably equal to or greater than 5:2, even more preferably equal to or greater than 3:1, particularly preferably equal to or greater than 7:2, especially preferably in the range of 7:2 to 10:1, and most preferably in the range of 4:1 to 8:1.

A mixture for use according to the present invention preferably comprises an effective total amount of compounds of formula (I), such that the activity of human HMG-CoA reductase is reduced in-vitro by 15% or more, preferably by 25% or more, more preferably by 40% or more, most preferably by 50% or more.

In a preferred aspect the invention relates to a compound or mixture for use according to the present invention, wherein the disease, disorder or condition is a cholesterol disorder, preferably selected from the group consisting of hypercholesterolemia (i.e. the compounds of formula (I), in particular euscaphic acid, exhibit hypocholesterolemic activity), low HDL levels, high LDL levels, arteriosclerosis, and atherosclerosis, and/or for increasing the HDL/LDL ratio.

The compounds of formula (I) used in accordance of the present invention occur in different plants of several plant families. It has been reported in the literature that, for example, pomolic acid may be obtained from *Sanguisorba officinalis*, rotundic acid from several *Ilex* species (e.g. *Ilex rotunda* or *Ilex purpurea*), *Mussaenda macrophylla* or *Guettarda platypoda*, and myrianthic acid from *Rhododendron japonicum* or *Myrianthus arboreus*.

US 2007/0014739 A1 describes numerous pentacyclic triterpene acids as being useful for controlling bacterial biofilms and bacterial infections. It also disclosed there that a plant source for tormentic acid and euscaphic acid is *Brazzeia soyauxii*.

CN 101849950 A relates to the use of rotundic acid extracted from the dry bark of *Ilex rotunda* Thunb. in pharmaceutical compositions for regulating blood lipids.

WO 2010/143058 discloses compositions comprising (i) one or more triterpenoids such as asiatic acid, kaji-ichigoside $F_1$, euscaphic acid, asiaticoside, tormentic acid and madecassic acid, and (ii) one or more specific polyphenols.

KR 2011-0018671 A relates to a pharmaceutical composition for preventing and treating cardiovascular diseases due to hypercholesterolemia containing *Cornus kousa* Burg. fruit extract or certain fractions or certain compounds thereof as active ingredient. Said pharmaceutical composition may contain the triterpene compounds ursolic acid, corosolic acid, taraxasterol, betulinic acid or betulinic aldehyde obtained from said fruit extract.

J. Chin. Chem. Soc. 2005, 52(6), 1275-1280 discloses that a methanolic extract of the leaves of *Planchonella duclitan* (Blanco) contains several triterpene acids, e.g. myrianthic acid, corosolic acid, ursolic acid, pomolic acid, and rotundic acid.

In Zhongguo Zhong Yao Za Zhi (China Journal of Chinese Materia Medica) 2001, 26(8), 549-551 cardiotonic effects of a methanolic extract obtained from the fruit of *Rosa bella* were investigated, said extract comprised inter alia pomolic acid, euscaphic acid, oleanolic acid and beta-sitosterol. It is also reported there that a dosage of 400 mg/kg had no obvious effect on total cholesterol, HDL-ac and triglyceride levels in the serum of rats.

Biosci. Biotechnol. Biochem. 2000, 64(8), 1707-1712 reports that unripe, wounded strawberry fruits produce/contain euscaphic acid, tormentic acid and myrianthic acid, said triterpene phytoalexins having antifungal properties.

Biol. Pharm. Bull. 2005, 28(1), 101-104 investigated the anti-inflammatory activity of extracts of the roots of *Rosa rugosa* and certain consitutents thereof, inter alia of tormentic acid and euscaphic acid.

It was observed in Cardiovasc. Drugs Ther. 2006, 20, 349-357 that certain ursane triterpenoids, isolated from the aerial part of *Salvia miltirrhiza* Bge., showed beneficial effects regarding vascular atherosclerotic lesions in treated mice.

Phytotherapy Research 2008, 22, 1040-1045 discloses that a triterpenoids-enriched extract of dried leaves and stems of *Salvia miltiorrhiza* had antiatherogenic activity.

Natural Product Sciences 2007, 13(2), 152-159 reported anti-hyperlipidemic activity of a 19-alpha-hydroxyursane-type triterpenoid rich fraction from leaves of *Rubus crataegifolis*.

Journal of Ethnopharmacology 2009, 122(3), 486-491 evaluated the hypoglycemic and hypolipidemic effects of a triterpene acid fraction from leaves of *Eriobotrya japonica* (Thunb.) Lindl. in the context of diabetes mellitus.

Overall, the prior art does not disclose nor suggest that the compounds of formula (I), particularly of formula (I-A), each as defined hereinbefore, and the plant extracts, the compositions, and the formulations according to the present invention (each as defined hereinafter) are HMG-CoA reductase inhibitors. The same applies for the use of one or more compounds of formula (I), particularly of formula (I-A), each as defined above, and the use of the plant extracts, the compositions, and the formulations according to the present invention (each as defined hereinafter) in the prophylactic and/or therapeutic treatment of a disease, disorder or condition that responds to a reduction of the HMG-CoA reductase activity in a mammal.

The fruits of *Amelanchier alnifolia*, also known as Saskatoon berry, Juneberry or serviceberry, are frequently used as food or in food products. The small dumose tree *Amelanchier alnifolia* is probably native to the northern plain provinces of Canada and the northwestern and midwestern United States. Although it also grows in the Rocky Mountains it is predominantly cultivated in Saskatchewan, Canada. The fruits (berries) may be eaten fresh and are also processed to beverages, marmalade, jam, pies and other bakery products.

Saskatoon berries have been reported to contain inter alia flavonoid polyphenols, chlorogenic acid, several vitamins (including tocopherol and vitamin C), sugars, fatty acids, and several minerals. The properties and health benefits mainly associated with Saskatoon berries and flavonoid polyphenols (in particular anthocyanins) are antioxidant activities. It is also reported that the seed oil obtained from Saskatoon berries' seeds contains very low amounts of sterols, predominant sterols being beta-sitosterol, delta-5-avenasterol and campesterol. Beta-sitosterol is known for reducing serum LDL cholesterol.

The terms and expressions, within the present text, preferably have the meaning given herein. In each embodiment of the present invention one, more than one or all general expressions, independently of one another, may be replaced with the more specific definitions, thus forming preferred or particularly preferred embodiments of the present invention, respectively.

Preferably, the compounds of formula (I) are natural compounds, that is, compounds that are present in and can be isolated or extracted from natural sources (especially those mentioned in detail herein) without chemical synthesis steps (although they may also be prepared synthetically) and are thus present as extracts or purified components of extracts, and not derivatives only obtainable by chemical synthesis.

Further, the compounds of formula (I) include all stereoisomers, such as those which may exist due to asymmetric carbons on the various substituents, including enantiomeric forms and diastereomeric forms. To the extent that compounds of formula (I) and the physiologically acceptable salts thereof may exist in their tautomeric form, all such tautomeric forms are also contemplated herein as part of the present invention.

Pharmaceutically (or nutraceutically) acceptable (i.e., non-toxic, physiologically acceptable) salts are preferred, although other salts are also useful, e.g., in isolation or purification steps which may be employed during preparation. Salts of compounds of formula (I) may be formed, for example, by reacting a compound of formula (I) with an amount of acid or base, such as an equivalent amount, in a medium such as one in which the salt precipitates or in an aqueous medium followed by lyophilization. Salts of the compounds of formula (I) may also be formed by reacting a compound of formula (I) with an alkylating agent, for example, by quaternization of an amine, where natural compounds are preferred. Also ion exchangers can be used to obtained a physiologically acceptable salt of a compound of formula (I) from a free form of a compound of formula (I), and vice versa.

A compound of formula (I) contains several acidic groups which may be deprotonated and form salts. In particular the carboxylic group (—COOH) may form salts (i.e. a carboxylate group). One or more of the acidic groups of a compound of formula (I) used in accordance with the present invention may be deprotonated with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, N-methyl-D-glucamines, N-methyl-D-glucamides, t-butyl amines, and salts with amino acids such as arginine, lysine and the like. Also salts with salt-forming pharmaceutical and/or nutraceutical carrier materials are possible and encompassed by the present invention.

Preferred physiologically, preferably pharmaceutically or nutraceutically acceptable salts of compounds of formula (I) are those in which the one, several or preferably all counterions (counteracting cation) are selected from the group consisting of $Na^+$, $K^+$, $NH_4^+$, trialkylammonium $NHR'_3^+$, $Mg^{2+}$, $Zn^{2+}$ and $Al^{3+}$.

In trialkylammonium $NHR'_3^+$, preferably each R' independently of the other radicals R' denotes an alkyl group having 1 to 30 C-atoms, preferably having 4 to 22 C-atoms. Particular preferred counterions in physiologically, preferably pharmaceutically or nutraceutically, acceptable salts of compounds of formula (I) are selected from the group consisting of $Na^+$, $K^+$, $Ca^{2+}$ and $Mg^{2+}$ and mixtures thereof.

In the context of the present invention, "essentially consists of" or "essentially consisting of" or similar terms mean that the total weight share is 90 wt. % or more, preferably 95 wt. % or more, more preferably 98 wt. % or more, most preferably 99 wt. % or more, in each case based on the total amount used. For example, "plant material essentially consisting of berries" means that the total amount of berries is 90 wt. % or more, preferably 95 wt. % or more, more preferably 98 wt. % or more, most preferably 99 wt. % or more, in each case based on the total amount of plant material employed.

In the context of the present invention, "essentially free of" means that the total weight share is less than 10 wt. %, preferably 5 wt. % or less, more preferably 2 wt. % or less, most preferably 1 wt. % or less, in each case based on the total amount used.

A reference to compound(s) (i.e. one or more compounds) of formula (I) always includes the compound(s) of formula (I) as such and the forms of the physiologically acceptable salts thereof. The compound(s) of formula (I) may be used in the context of the present invention in essentially pure form, as mixtures of compound(s) of formula (I), as part of a plant extract, as part of an enriched plant extract, as part of a composition, or as part of a (preferably pharmaceutical or nutraceutical) formulation.

Where relative amounts of components are given in %, this means weight %, unless indicated otherwise.

As used herein, the term "effective amount" or "effective dose" refers to the (preferably oral) administration of an effective dose of one or more compounds of formula (I) (optionally in form of a mixture, a plant extract, a composition or a formulation as defined in the context of the present invention) that produces the effects for which it is administered.

As used herein, the term "therapeutical" or "therapeutically" refers to the (in particular oral) administration of a therapeutically effective dose of one or more compounds of formula (I) and/or the physiologically acceptable salts thereof (optionally in form of a mixture, a plant extract, a composition or a formulation as defined in the context of the present invention) that produces the effects for which it is administered, i.e. that will elicit the biological or medical response (in vitro or in vivo, preferably in vivo in a mammal, particularly in vivo in human being) that is being sought, in particular the amelioration and/or alleviation of the symptoms of the disorder, disease or condition being treated up to and including complete cure.

As used herein, the term "prophylactic" or "prophylactically" refers to the (in particular oral) administration of a prophylactically effective dose of one or more compounds of formula (I) (optionally in form of a mixture, a plant extract, a composition or a formulation as defined in the context of the present invention) that produces the effects for which it is administered, i.e. that will elicit the biological or medical response (in vitro or in vivo, preferably in vivo in a mammal, particularly in vivo in a human being) that is being sought, in particular the prevention of the onset of a disorder, disease or condition in individuals at risk for such disorder, disease or condition as mentioned herein.

By the term "extract", either a direct extract (in liquid, viscous or dried form), e.g. obtained as described in the context of the present invention, or a further enriched extract (obtainable e.g. by one or more further purification steps after extraction, e.g. chromatography, for example as described below) containing one or more, preferably two or more compounds of formula (I) is meant.

The extracts or compounds according to the present invention may be used as such, or in the form of and as part of (a preferably pharmaceutical or nutraceutical) formulation (the latter term includes food additives, food supplements, functional food products and dietary supplements) or in the form of functional food (products).

Where the compounds of formula (I) or mixture of compounds of formula (I) are used as food or dietary supplement, this means that the compound(s), extracts or (preferably pharmaceutical or nutraceutical) formulations comprising them, each according to the present invention, can be added to any other nutrient, pharmaceutical or nutraceutical. Thus, they can especially serve as food or dietary supplement. However, the compound(s), compositions, or plant extracts may also be administered as such.

"Nutraceuticals", "Functional Food", or "Functional Food products" (sometimes also called "Foodsceuticals", "Medicinal Food" or "Designer Food") for use according to the present invention are defined as food products (including beverages) suitable for human consumption—the expression comprises any fresh or processed food having a health-promoting and/or disease-preventing property beyond the basic nutritional function of supplying nutrients, including food made from functional food ingredients or fortified with health-promoting additives, especially with effects in the prophylaxis or treatment of a disease, disorder or condition that responds to a reduction of the HMG-CoA reductase activity in a mammal, preferably a human being, and in which a compound or a mixture of compounds of formula (I), or an extract comprising one or more of said compound(s), respectively, according to the present invention is used as active ingredient in an effective amount.

"Comprising" or "including" or "having" wherever used herein is meant not to be limiting to any elements stated subsequently to such term but rather to encompass one or more further elements not specifically mentioned with or without functional importance, that is, the listed steps, elements or options need not be exhaustive.

"Obtainable" means that a product (e.g. plant extract, composition or compounds) may be obtained by the specified method, and preferably is obtained by said method.

Where ratios or percentages are given, these refer to the weight (e.g. (w/w) or percent by weight, wt. %), unless indicated otherwise. Where volume ratios (v/v) or volume percentages (vol. %) are given, these refer to the volumes at 25° C. and 1013 mbar.

By the term a "disease, disorder or condition that responds to a reduction of the HMG-CoA reductase activity", preferably a disease is meant that is, in the sense of an amelioration for the mammal, in particular human being, treated, affected by an inhibition (i.e. an antagonistic action) of the HMG-CoA reductase activity. Among such diseases, disorders or conditions, cholesterol disorders are particularly to be mentioned, and preferably selected from the group consisting of hypercholesterolemia, low HDL levels, high LDL levels, arteriosclerosis, and atherosclerosis.

In another aspect, the present invention relates to a composition or plant extract comprising
    euscaphic acid,
    tormentic acid, and
    a total amount of 0 to 10 wt. % of organic solvents having a molecular weight of 100 g/mol or lower, preferably of organic solvents having a molecular weight of 120 g/mol or lower, based on the total weight of the composition or plant extract,
wherein the ratio by weight of euscaphic acid to tormentic acid is greater than 1:1, preferably equal to or greater than 5:2.

The compositions and plant extracts according to the present invention comprising euscaphic acid and tormentic acid in a ratio by weight of 1:1 or more were found to have unexpectedly good HMG-CoA reductase inhibiting activity. This is for example apparent from the data presented in example 4 below: a composition or plant extract according to the present invention exhibits an almost as good HMG-CoA reductase inhibiting activity as euscaphic acid alone, although said extract comprises only a limited amount of euscaphic acid. Another reason for the good HMG-CoA reductase inhibiting activity of the compositions and plant extracts according to the present invention probably is that other constituents accompanying euscaphic acid and tormentic acid (and preferably myrianthic acid) enhance the HMG-CoA reductase inhibiting activity of the compounds of formula (I), in particular of euscaphic acid, such as for example quercetin, quercetin mono-glycosides, and/or one or more ACAT-inhibitors present in said plant extract or composition.

Particularly the presence of one or more quercetin monoglycosides, preferably comprising or consisting of quercetin-3-O-beta-D-galactopyranoside, was found to be advantageous. In our own investigations it was found that quercetin-3-O-beta-D-galactopyranoside has a very good HMG-CoA reductase inhibiting activity as well. Further, the additional presence of one or both ACAT-inhibitors ursolic acid and/or corosolic acid was found to be advantageous in compositions and plant extracts according to the present invention.

The additional advantage of using the compositions and plant extracts according to the present invention is that they are technically much easier (and therefor also cheaper) to produce (also and in particular on a large scale) and are obtained in appreciable higher yields than euscaphic acid in high purity.

Preferably, a composition or plant extract according to the present invention comprises, in each case based on the total weight of the composition or plant extract,
    1 to 50 wt. %, preferably 1 to 35 wt. %, more preferably 3 to 25 wt. % of euscaphic acid,
    0.5 to 15 wt. %, preferably 1 to 10 wt. % of tormentic acid,
    0 to 10 wt. %, preferably 0.5 to 8 wt. % of myrianthic acid, and
    a total amount of 0 to 10 wt. % of organic solvents having a molecular weight of 110 g/mol or lower, preferably of organic solvents having a molecular weight of 120 g/mol or lower,
wherein the ratio by weight of euscaphic acid to tormentic acid is greater than 1:1, preferably equal to or greater than 2:1, more preferably equal to or greater than 5:2, even more preferably equal to or greater than 3:1, particularly preferably equal to or greater than 7:2, especially preferably in the range of 7:2 to 10:1, and most preferably in the range of 4:1 to 8:1.

Preferably, a composition or plant extract according to the present invention comprises
    3 to 25 wt. %, preferably 5 to 20 wt. %, more preferably 8 to 17 wt. % of euscaphic acid,
    1 to 10 wt. %, preferably 1 to 6 wt. % of tormentic acid,
    0.5 to 8 wt. %, preferably 0.75 to 5 wt. % of myrianthic acid, and
    a total amount of 0 to 5 wt. % of organic solvents having a molecular weight of 110 g/mol or lower, preferably of organic solvents having a molecular weight of 120 g/mol or lower,
in each case based on the total weight of the composition or plant extract,
wherein the ratio of euscaphic acid to tormentic acid by weight is equal to or greater than 1:1, preferably equal to or greater than 2:1, more preferably equal to or greater than 3:1, particularly preferably equal to or greater than 7:2, especially preferably in the range of 7:2 to 10:1, and most preferably in the range of 4:1 to 8:1.

Preferably, a composition or plant extract according to the present invention additionally comprising one or more other HMG-CoA reductase inhibitors not corresponding to formula (I) as defined above, preferably other HMG-CoA reductase inhibitors not having a pentacyclic triterpenoid acid structure with 30 carbon atoms, preferably not having a pentacyclic triterpenoid acid structure with 30 or more carbon atoms, wherein preferably one or more of said other HMG-CoA reductase inhibitors are quercetin mono-glycosides, preferably comprising or consisting of quercetin-3-O-beta-D-galactopyranoside.

Preferably a composition or plant extract according to the present invention comprises quercetin mono-glycosides, preferably comprising or consisting of quercetin-3-O-beta-D-galactopyranoside, in a total amount of 0.1 wt. % or more, more preferably in a total amount of 0.25 to 20 wt. %, even more preferably in a total amount of 0.25 to 15 wt. %, particularly preferably in a total amount of 0.3 to 5 wt. %, and most preferably in a total amount of 0.5 to 3 wt. %, in each case based on the total weight of the composition or plant extract.

Preferably, a composition or plant extract according to the present invention additionally comprising one or more inhibitors of LDL oxidation, preferably comprising quercetin and optionally one or more further inhibitors of LDL oxidation.

Preferably a composition or plant extract according to the present invention comprises quercetin in a total amount of 0.1 wt. % or more, more preferably in a total amount of 0.25 to 20 wt. %, even more preferably in a total amount of 0.25 to 15 wt. %, particularly preferably in a total amount of 0.3 to 5 wt. %, and most preferably in a total amount of 0.5 to 3 wt. %, in each case based on the total weight of the composition or plant extract.

Preferably, a composition or plant extract according to the present invention additionally comprising one, two or more further active ingredients selected from the group consisting of acyl CoA:cholesterol acyltransferase (ACAT) inhibitors, preferably one or more substances having ACAT 2-inhibiting activity, particularly one or more substances having human ACAT 2-inhibiting activity.

Preferably, a composition or plant extract according to the present invention additionally comprises
- one, two, three or four different mono-O-caffeoylquinic acids [preferably 1-O-caffeoylquinic acid, 3-O-caffeoylquinic acid (chlorogenic acid), 4-O-caffeoylquinic acid (cryptochlorogenic acid), and/or 5-O-caffeoylquinic acid (neochlorogenic acid)], preferably in a total amount of 1 wt. % or more, more preferably in a total amount of 1 to 25 wt. %, particularly preferably in a total amount of 1.5 to 20 wt. %, in each case based on the total weight of the composition or plant extract, and
- one or more naturally occurring ACAT inhibitors, preferably corosolic acid, oleanolic acid and/or ursolic acid.

Several studies report anticholesterol effects, including lowering of triglycerides, of mono-O-caffeoylquinic acids, in particular of chlorogenic acid, and of corosolic acid which are intertwined with the antioxidative and hypoglycemic effects of these compounds. These compounds are reported to reduce cholesterol and triglycerides, including through reduced oxidative susceptibility of low-density lipoproteins (LDL).

For example, the effect of corosolic acid (e.g. obtainable from *Lagerstroemia speciosa* L.) on hypercholesterolemia and its ACAT-inhibiting activity is described in Biomedical Research 2010, 31(4), 213-218 and the references cited therein.

Corosolic may be obtained from natural sources such as various plants, or synthesized, for example as disclosed in U.S. Pat. No. 7,071,229 B2.

Preferably a composition or plant extract according to the present invention (as defined above) comprises
- two or more different mono-O-caffeoylquinic acids, preferably in a total amount of 1.5 to 25 wt. % based on the total weight of the composition or plant extract, more preferably in a total amount of 2 to 20 wt. %,
- corosolic acid and/or ursolic acid, preferably in a total amount of 1 to 25 wt. % based on the total weight of the composition or plant extract, more preferably in a total amount of 2 to 20 wt. %, and
optionally one or more other ACAT inhibitors (i.e. ACAT inhibitors other than corosolic acid and ursolic acid) selected from group of further naturally occurring ACAT inhibitors (preferably naturally occurring inhibitors of human ACAT isoform ACAT1 and/or isoform ACAT2), preferably selected from the group consisting of maslinic acid, 23-hydroxyursolic acid, oleanolic acid, betulinic acid, betulin, 2,3-dihydroxy-24-nor-4(23),11-ursadien-28,13, -olide, manassantin A, manassantin B, pyripyropenes (preferably pyripyropene A, pyripyropene B, pyripyropene C, pyripyropene D, pyripyropene E, pyripyropene F, pyripyropene M, pyripyropene N, pyripyropene O, pyripyropene P, pyripyropene Q, pyripyropene R, more preferably pyripyropene A, pyripyropene E, pyripyropene F and/or pyripyropene M), dineolignans, sesquineolignans, saucerneol B, obovatol, tetrahydroobovatol, honokiol, magnolol, panaxynol, panaxydol, panaxytriol, ulmoidol, ilekudinol A, ilekudinol B, ilekudinol C, 27-p-coumaroyloxyursolic acid, pheophorbides (preferably pheophorbide A, pheophorbide A-methyl ester), bavachin, isobavachalcone, 9,10-epoxy-16-heptadecene-4,6-diyine-3-one, ilexoside XLVIII, cynarasaponin C, guineesine (preferably (E,E,E)-guineesine), lupeol, glisoprenin A, glisoprenin B, bis(2-hydroxy-3-tert-butyl-5-methylphenyl) methane, beta-sanshool, gamma-sanshool, hydroxyl-beta-sanshool, yakuchinone B, isochromophilones (preferably isochromophilone III, isochromophilone IV, isochromophilone V, isochromophilone VI, isochromophilone VII, isochromophilone VIII), purpactin A, purpactin B, purpactin C, (9Z)-octadecenamide, (9Z,12Z)-octadecadienamide, ginseng saponins, kudingoside A, kudingoside B, decursin, decursinol angelate, lateritin, enniatins (preferably enniatin A, enniatin A1, enniatin B, enniatin B1, enniatin C, enniatin D, enniatin E, beauvericin), beauveriolides (preferably beauveriolide I, beauveriolide III), epi-cochlioquinone A, terpendoles (preferably terpendole A, terpendole B, terpendole C, terpendole D, terpendole E, terpendole F, terpendole G, terpendole H, terpendole I, terpendole J, terpendole K, terpendole L, more preferably terpendole D), spylidone, phenylpyropene A, phenylpyropene B, retrofractamide A, pipericide, piperchabamide, pellitorin, dehydroretrofractamide C, dehydropipernonaline, ixerin M, crepiside I, aurasperone A, aurasperone D, flavasperone, gomisins (preferably gomisin A, gomisin J, gomisin L2, gomisin N), benzoylisogomisin O, schizandrin, schizandrin B, schizandrin C, schizantherins (preferably schizantherin D), licarins (preferably licarin A), machilins (preferably machilin A, machilin F), nectandrin A, nectandrin B, glabrol, esculeogenin A, esculeoside A, aceriphyllic acid A, hypomycine, emindole SB, and paspaline.

Preferably, the one or more further naturally occurring ACAT inhibitors are selected from the group ACAT inhibitors occurring in plants, and are preferably selected from the group consisting of maslinic acid, 23-hydroxyursolic acid, oleanolic acid, betulinic acid, betulin, 2,3-dihydroxy-24-nor-4(23),11-ursadien-28,13,-olide, manassantin A, manassantin B, dineolignans, sesquineolignans, saucerneol B, obovatol, tetrahydroobovatol, honokiol, magnolol, panaxynol, panaxydol, panaxydiol, panaxytriol, ulmoidol, ilekudinol A, ilekudinol B, ilekudinol C, 27-p-coumaroyloxyursolic acid, pheophorbides (preferably pheophorbide A, pheophorbide A-methyl ester), bavachin, isobavachalcone, ilexoside XLVIII, cynarasaponin C, guineesine (preferably (E,E,E)-guineesine), lupeol, beta-sanshool, gamma-sanshool, hydroxyl-beta-sanshool, yakuchinone B, (9Z)-octadecenamide, (9Z,12Z)-octadecadienamide, ginseng saponins, kudingoside A, kudingoside B, decursin, decursinol angelate, retrofractamide A, pipericide, piperchabamide, pellitorin, dehydroretrofractamide C, dehydropipernonaline, ixerin M, crepiside I, gomisins (preferably gomisin A, gomisin J, gomisin L2, gomisin N), benzoylisogomisin O, schizandrin, schizandrin B, schizandrin C, schizantherins (preferably schizantherin D), licarins (preferably licarin A), machilins (preferably machilin A, machilin F), nectandrin A, nectandrin B, glabrol, esculeogenin A, esculeoside A, and aceriphyllic acid A.

Preferably a composition or plant extract according to the present invention (as defined above) comprises
3-18% of euscaphic acid,
0.5-7% of tormentic acid,
0.5-3% of myrianthic acid,
0-20% of ursolic acid,
1-5% of corosolic acid,
0-45% of oleanolic acid,
0-20% in total of caffeoylquinic acids, 0.5-25% in total of quercetin and quercetin mono-glycosides (preferably comprising quercetin 3-O-beta-D-galactopyranoside),
1-50% in total of sugars and sugar alcohols, and
15-40% in total of fatty acids (preferably including linolenic acid, linoleic acid, and (or oleic acid).

More preferably a composition or plant extract according to the present invention (as defined above) comprises
8-17% of euscaphic acid,
1-6% of tormentic acid,
0.75-2.5% of myrianthic acid,
2-20% of ursolic acid,
1.5-5% of corosolic acid,
0-45% of oleanolic acid,
0-18% in total of caffeoylquinic acids,
0.75-25% in total of quercetin and quercetin mono-glycosides (preferably comprising quercetin 3-O-beta-D-galactopyranoside),
2-45% in total of sugars and sugar alcohols, and
20-35% in total of fatty acids (preferably including linolenic acid, linoleic acid, and (or oleic acid).

To a certain extent the amount of the different constituents of a composition or plant extract according to the present invention depends on the solvent mixture used in the extraction step(s).

In a preferred embodiment, a composition or plant extract according to the present invention (as defined above) comprises
8-16% of euscaphic acid,
2-5% of tormentic acid,
0.75-2.5% of myrianthic acid,
10-20% of ursolic acid,
2.5-5% of corosolic acid,
1.5-16% in total of caffeoylquinic acids,
1.25-25% in total of quercetin and quercetin mono-glycosides (preferably comprising quercetin 3-O-beta-D-galactopyranoside),
4-45% in total of sugars and sugar alcohols, and
22-28% in total of fatty acids (preferably including linolenic acid, linoleic acid, and (or oleic acid).

In another preferred embodiment, a composition or plant extract according to the present invention (as defined above) comprises
12-18% of euscaphic acid,
3-7% of tormentic acid,
0.5-2% of myrianthic acid,
0-3% of ursolic acid,
2-5% of corosolic acid,
25-45% of oleanolic acid, preferably 35-45% of oleanolic acid,
0-3% in total of caffeoylquinic acids,
0.5-2.5% in total of quercetin and quercetin mono-glycosides (preferably comprising quercetin 3-O-beta-D-galactopyranoside),
1-5% in total of sugars and sugar alcohols, and
25-35% in total of fatty acids (preferably including linolenic acid, linoleic acid, and (or oleic acid).

The functional food products or pharmaceutical products according to the present invention may be manufactured according to any suitable process, preferably comprising extraction of one or more compounds of formula (I) and admixing to a functional food product or at least one nutraceutically or pharmaceutically acceptable carrier.

A product, in particular a functional food product, comprising one or more compounds of formula (I), particularly of one or more compounds and/or mixture of compounds of formula (I-A), for use according to the present invention, can, for example, be obtained by
(a) extraction of one or more compounds of formula (I), particularly of one or more compounds of formula (I-A), from a suitable plant material, and
(b) mixing the extract obtained in step (a) in an effective amount and/or as active ingredient with one or more other constituents to obtain a product, in particular a functional food product, said other constituents preferably comprising one or more carrier materials, solvents and/or dispersants.

Further processing steps may precede and/or follow the mentioned steps, such as drying (e.g. freeze-drying, spray-drying, fluid bed or spouted bed or evaporation), granulation, agglomeration, concentrating (e.g. to syrups, formed via concentration and/or with the aid of thickeners), pasteurizing, sterilizing, freezing, dissolving, dispersing, filtering, centrifuging, confectioning, and the like.

The (particularly) preferred aspects and embodiments mentioned hereinbefore or hereinafter relating to mixtures, extracts, compositions or plant extracts according to the present invention or produced according to a method of the present invention also apply to and preferably are combined with other (particularly) preferred aspects and embodiments, uses and methods in accordance with the present invention. In particular, the (particularly) preferred embodiments disclosed hereinbefore or hereinafter with respect to a composition or plant extract according to the present invention also apply for a (preferably pharmaceutical or nutraceutical) formulation according to the present invention.

A (preferably pharmaceutical or nutraceutical) formulation according to the present invention differs from the fruit or berry itself. However, a (preferably pharmaceutical or nutraceutical) formulation according to the present invention may be of any form. Such a formulation may additionally comprise one or more further ingredients commonly used in the food or nutraceutical industry, such as flavors, sugars, minerals, vitamins, stabilizers, thickeners, dietary fibers, proteins, amino acids or the like in appropriate amounts, or mixtures of two or more thereof, in accordance with the desired type of formulation.

Examples of (preferably pharmaceutical or nutraceutical) formulations according to the present invention, particularly formulations suitable for oral consumption, are
  fruit or vegetable containing products (preferably products containing juice, extract, puree, mash, pulp, concentrate, dried parts of lemon, lime, grapefruit, orange, sweet orange, bitter orange, bergamot, mandarin, apple, pear, prickly pear, peach, apricot, fig, pineapple, prune, mango, melon, plum, kiwi, lychee, banana, cherry, sweet cherry, strawberry, raspberry, red currant, black currant, blackberry, blueberry, marionberry, passion fruit, grapes (white grape, red grape, green grape, purple grape), pomegranate, acerola, tomato, carrot, parsnip, pumpkin, lettuce, cabbage, fermeted cabbage, bean, pea, potato, bell pepper, red chili, green chili, onion, celery, cucumber, leek, broccoli, cauliflower, radish, aubergibe, zucchini),
  soy based products (preferably soy milk, soy drinks, soy yoghurts),
  non-alcoholic beverages and syrups (preferably lemonades, beverage concentrates (syrups), non-carbonated soft drinks, and carbonated soft drinks),
  alcoholic beverages,
  products containing one or more other extracts from herbs and/or spices (preferably selected from the group consisting of vanilla, cinnamon, anise, fennel, clove, cardamom, tamarind, nutmeg, allspice, black pepper, licorice, ginger, rose hip, green tea, red tea, rooibos tea, mate tea, honeybush tea, pu-erh tea, oolong tea, black tea, coffee bean, cocoa bean, peppermint, spearmint, and wintergreen), non-frozen fermented or non-fermented dairy or dairy-based products (preferably milk, quark, cream cheese, custards, puddings, mousses, milk based drinks, drink yoghurts, and yoghurts), frozen products (preferably ice-cream, frozen yoghurt, sorbet, ice milk, frozen custard, water-ices, granitas, sherbets. and frozen fruit purees), sweet baked goods (preferably bread, buns, cakes, muffins, cupcakes, biscuits, shortbread, and cookies), oil and/or fat containing spreads (preferably margarine, butter products, peanut butter, mayonnaise, and sauces (preferably (salad) dressings and tartar sauce)), sweet snacks and confectionary products, preferably chocolate bars, granola bars (muesli bars), soft candies (such as chewy candy, soft chews, gummy candy, taffy candy, jelly beans, fudge, gumdrops), and hard candies (i.e. boiled sweets, such as toffees, lozenges, candy sticks, lollipops), cereal products (preferably muesli and breakfast cereals), instant powders (preferably instant beverage powders, instant sauce powders or instant dessert powders, more preferably instant coffee, instant tea, instant cocoa, and instant powders for corresponding mix beverages (e.g. cappuccino, latte macchiato), instant sauces (preferably fruit sauces), and instant pudding), savory snacks (preferably crackers, chips (e.g. potato chips, corn chips), extrudated snacks, and pretzels).

The present invention also relates to a formulation, preferably pharmaceutical or nutraceutical formulation, comprising (i) a mixture or extract according to the present invention (as defined above, preferably in one of the preferred or particularly preferred embodiments) or a composition or plant extract according to the present invention (as defined above, preferably in one of the preferred or particularly preferred embodiments), preferably in an effective amount, and (ii) one or more additional ingredients selected from the group consisting of cholesterol uptake inhibiting substances, bile acid circulation regulating substances and/or bile acid excretion regulating substances, preferably selected from the group consisting of phytosterols and $C_2$-$C_{22}$-fatty acid esters of phytosterols, preferably selected from the group of phytosterols occurring in plants (i.e. plant sterols/stanols) and the $C_2$-$C_{22}$-fatty acid esters thereof, more preferably consisting of beta-sitosterol, campesterol, stigmasterol, brassicasterol, stigmastanol (also called beta-sitostanol), campestanol, and the esters thereof, preferably the $C_{10}$-$C_{24}$ esters thereof, more preferably the $C_{12}$-$C_{18}$ esters thereof, particularly the laurates, myristates, palmitates, oleates, stearates and linoleates thereof, wherein preferably the ratio by weight of the total amount of compounds of formula (I) as defined above to the total amount of phytosterols and $C_2$-$C_{22}$-fatty acid esters of phytosterols is greater than 1:4, more preferably greater than 2:5, more preferably greater than 2:3, even more preferably greater than 1:1, especially more preferably greater than 3:2, beta-glucans (preferably beta-glucans from oats, oat bran, barley and/or barley bran), chitosan, galactomannan, glucomannan, arabinoxylan, guar gum, pectins, alginic acid and physiologically acceptable salts thereof, oat fiber, oat bran, flaxseed, flaxseed fiber, barley fiber, fiber from *Psyllium*, *Psyllium* seed husks (husks of the seeds of *Plantago ovata*), and aqueous extracts of *Psyllium* seed husks, and/or di-O-caffeoylquinic acids, tri-O-caffeoylquinic acids, and tetra-O-caffeoylquinic acids, more preferably di-O-caffeoylquinic acids, particularly preferably cynarin (1,5-di-O-caffeoylquinic acid, optionally as constituent of an artichoke extract), 1,3-di-O-caffeoylquinic acid, 3,4-di-O-caffeoylquinic acid, 3,5-di-O-caffeoylquinic acid and/or 4,5-di-O-caffeoylquinic acid, and/or procyanidines (=proanthocyanidines), preferably selected from the group consisting of Procyanidin B1, Procyanidin B2, Procyanidin A2, Procyanidin B5, Procyanidin C1, grape seed proanthocyanidin, and grape seed proanthocyanidin extract, and/or carotenoids, preferably selected from the group consisting of beta-carotene, lycopene, phytoene, and phytofluene, more preferably lycopene, and/or one or more, preferably two, three, four, five, six, seven, eight or more flavoring agents, and/or pharmaceutically or nutraceutically acceptable edible carrier materials, diluents or excipients.

Preferably, a (preferably pharmaceutical or nutraceutical) formulation according to the present invention (which differs from plant parts, in particular fruits, as such) comprises a total amount of compounds of formula (I) for use according to the present invention and the physiologically acceptable salts thereof in the range of 0.005 to 30 wt. %, more preferably in the range of 0.01 to 20 wt. %, even more preferably in the range of 0.05 to 12 wt. %, particularly preferably in the range of 0.1 to 8 wt. %, and most preferably in the range of 0.125 to 6 wt. %, each case based on the total weight of the (preferably pharmaceutical or nutraceutical) formulation.

Preferably, a composition according to the present invention, a plant extract according to the present invention or a formulation according to the present invention (each as defined herein in accordance with the present invention) is not an extract, in particular not an aqueous-methanolic, methanolic, aqueous-ethanolic, ethanolic, chloroformic, or EtOAc extract, obtained from *Brazzeia soyauxii*, *Ilex rotunda* Thunb., *Cornus kousa* Burg. fruits, *Planchonella duclitan* (Blanco) leaves, *Rosa bella* fruits, strawberry fruits (in particular not unripe, wounded strawberry fruits), *Rosa rugosa* roots, *Potentilla chinesis* herbs, the aerial parts of *Salvia miltirrhiza* Bge., dried leaves and/or stems of *Salvia miltiorrhiza*, leaves of *Rubus crataegifolis*, and leaves of *Eriobotrya japonica* (Thunb.) Lindl.

Preferably, a (preferably pharmaceutical or nutraceutical) formulation according to the present invention is suitable for orally consumption by mammals, in particular human beings. i.e. is suitable and intended to be introduced into the oral cavity and swallowed by mammals, in particular human beings.

The different types of fibers preferably used in a (preferably pharmaceutical or nutraceutical) formulation according to the present invention are further described below. In an embodiment the fiber of a (preferably pharmaceutical or nutraceutical) formulation is a plant fiber and/or an algae fiber. When being a combination of two or more types of fibers, any ratio of the different fibers may be used. For example at least 50% of the fibers of a (preferably pharmaceutical or nutraceutical) formulation according to the present invention may be algae fibers. In another embodiment the fiber may be selected from the group of galactomannan, glucomannan, pectin, arabinoxylan, cellulose, alginate, and/or chitosan.

Preferred are natural fibers. Natural fibers are expected not to hamper the individual ingesting a (preferably pharmaceutical or nutraceutical) formulation according to the present invention. More preferred are fibers with gelling properties, preferably alginate, galactomannans, glucomannans and pectin. The mechanical satiety when using fibers with gelling properties is preferably obtained due to the formation of gel in the stomach of an individual.

In an embodiment the galactomannan to be incorporated in a (preferably pharmaceutical or nutraceutical) formulation according to the present invention is selected from the group of fenugreek gum, guar gum, tara gum, and/or locust bean gum (carob gum). If galactomannan is used in a (preferably pharmaceutical or nutraceutical) formulation according to the present invention, galactomannan is preferably mixed with other fibers.

A combination of galactomannan and alginate is preferred, e.g. to obtain a gel forming mix of fibers and/or to obtain a firm and flexible gel.

Guar gum comes from the endosperm of seeds of guar, *Cyamopsis tetragonolobus*, also called Indian cluster bean. It is composed of approximately 83% high molecular weight galactomannans, a water soluble fibre. In the context of the present invention, the guar gum used may advantageously be partially hydrolysed guar gum. The molecular weight of guar gum preferably is in the range of 10 kDa and 300 kDa, more preferably in the range of 10 kDa and 100 kDa, even more preferably in the range 10 kDa and 30 kDa.

Galactomannan may be obtained by using plant parts of *Trigonelle foenumgraecum*, *Cyamopsis tetragonolobus*, *Caesalpinia spinosa*, *Ceratonia siliqua*, and/or plant parts of plant belonging to the family Fabaceae such as Alfalfa (*Medicago sativa*), clover (*Trifolium* species), peas (*Pisum sativum*), beans (species of *Phaseolus, Vicia, Vigna, Cicer, Lathyrus, Lablab, Psophocarpus, Cajanus, Stizolobium, Cyamopsis, Canavalia, Macrotyloma, Erythrina*), lentils (*Lens culinaris*), lupins (*Lupinus* species), mesquite (*Prosopis* species), carob (*Ceratonia siliqua*), soy (*Glycine max*), and/or peanut (*Arachis hypogaea*).

Plant parts may be obtained from beans selected from the group of *Vicia faba* (broad beans, known in the US as fava beans), *Vigna Aconitifolia* (Moth bean), *Vigna Angularis* (azuki bean), *Vigna mungo* (urad bean), *Vigna radiata* (mung bean), *Vigna umbellatta* (ricebean), *Vigna unguiculata* (cowpea—includes the black-eyed pea, yardlong bean and others), *Cicer arietinum* (chickpea also known as the garbanzo bean), *Pisum sativum* (pea), *Lathyrus sativus* (Indian pea), *Lathyrus tuberosus* (Tuberous pea), *Lens culinaris* (lentil), *Lablab purpureus* (hyacinth bean), *Phaseolus acutifolius* (tepary bean), *Phaseolus coccineus* (runner bean), *Phaseolus lunatus* (lima bean), *Phaseolus vulgaris* (common bean, includes the pinto bean, kidney bean, caparrones, and many others), *Glycine max* (soybean), *Psophocarpus tetragonolobus* (winged bean), *Cajanus cajan* (pigeon pea), *Stizolobium* spp (velvet bean), *Cyamopsis tetragonoloba* (guar), *Canavalia ensiformis* (jack bean), *Canavalia gladiata* (sword bean), *Macrotyloma uniflorum* (horse gram), *Lupinus mutabilis* (tarwi), *Lupinus albus* (lupini bean), and/or *Erythrina herbacea* (Coral bean). The *Trifolium* species is preferably *Trifolium repens*. The bean is preferably *Phaseolus vulgaris*.

In an embodiment the glucomannan can be obtained from a plant selected from the group of *Aloe* genus and/or *Amorphophallus* and/or *Phaseolus* spp.; the *Phaseolus* spp is preferably *Phaseolus aureus*.

In the case that plant material, an extract or a constituent of the *Aloe* genus is used in a (preferably pharmaceutical or nutraceutical) formulation according to the present invention, the *Aloe* species preferably is selected from the group consisting of *Aloe vera* (syn *A. barbadensis*, *Aloe indica*, *Aloe perfoliata* and *A. vulgaris*), *Aloe arborescens*, *Aloe aristata*, *Aloe dichotoma*, *Aloe nyeriensis*, *Aloe variegata*, *Aloe barbadensis*, *Aloe wildii*, in turn plant material from *Aloe vera* being preferred.

A preferred species of the *Amorphophallus* species is *Amorphophallus konjac*. Plant parts from dicotyledons can be selected from species belonging to the family Fabaceae and/or Araceae.

The plants belonging to the family Fabaceae can be selected from the species *Medicago sativa*, *Trifolium* species, *Pisum sativum*, *Lens culinaris*, *Lupinus* species, *Prosopis* species, *Ceratonia siliqua*, *Glycine max*, *Arachis hypogaea*, *Vica faba*, *Vigna Aconitifolia*, *Vigna Angularis*, *Vigna mungo*, *Vigna radiata*, *Vigna umbellatta*, *Vigna unguiculata*, *Cicer arietinum*, *Pisum sativum*, *Lathyrus sativus*, *Lathyrus tuberosus*, *Lens culinaris*, *Lablab purpureus*, *Phaseolus acutifolius*, *Phaseolus coccineus*, *Phaseolus lunatus*, *Phaseolus vulgaris*, *Glycine max*, *Psophocarpus tetragonolobus*, *Cajanus cajan*, *Stizolobium* spp, *Cyamopsis tetragonoloba*, *Canavalia ensiformis*, *Canavalia gladiata*, *Macrotyloma uniflorum*, *Lupinus mutabilis*, *Lupinus albus*, and/or *Erythrina herbacea*. In an embodiment pectin used in a (preferably pharmaceutical or nutraceutical) formulation according to the present invention can be obtained from the group of plants of sugar beets (*Beta vulgaris*), carrot (*Daucus carota*), apple (*Malus domestica*), apricot (*Prunus armeniaca*), quince (*Cydonia oblonga*), plum (*Prunus* species), gooseberries (*Ribes uva-crispa*), and/or orange (*Citrus xsinensis*) and or lime (*Citrus×aurantia*, *Citrus×hystrix*) and/or lemon (*Citrus limon*). Preferred is pectin from apple, citrus species, and/or sugarbeet.

Pectins gel at low concentrations. A preferred total amount of pectins of any type or combination of any types of pectins is in the range of 0.1-2 wt. %, more preferred 0.2-1.0 wt. %, further preferred 0.3-0.7% wt., based on the total weight of a (preferably pharmaceutical or nutraceutical) formulation according to the present invention.

Beta-glucans are polysaccharides extracted from the cell wall of green plants, cereals (in particular oats and barley), certain algae and mushrooms (maitake and shiitake). They are primarily composed of glucose molecules or their derivative, bound together by beta bonds (beta1-3 or beta1-4 and/or beta1-6). The source of beta-glucan fibres is generally an extract of oats or barley, enriched in said fibres. Also purified extracts of beta-glucan fibres are commercially available, having a beta-glucan content of about 70% or even more.

Carotenoids are naturally occurring tetraterpenoid organic compounds. There are over 600 known carotenoids; they are generally divided into two classes, the xanthophylls (which contain oxygen) and the carotenes (which are purely hydrocarbons, and contain no oxygen).

Preferred carotenoids that may be used in combination with a composition or plant extract according to the present invention are preferably selected from the group consisting of α-carotene, β-carotene, γ-carotene, δ-carotene, ε-carotene, ζ-carotene, lycopene, neurosporene, phytoene, phytofluene, antheraxanthin, astaxanthin, canthaxanthin, citranaxanthin, cryptoxanthin, diadinoxanthin, diatoxanthin, dinoxanthin, flavoxanthin, fucoxanthin, lutein, neoxanthin, rhodoxanthin, rubixanthin, violaxanthin, zeaxanthin, abscisic acid, apocarotenal, bixin, crocetin, ionones, peridinin, retinal, retinoic acid, and retinol.

Preferably, the total amount of carotenoids in a (preferably pharmaceutical or nutraceutical) formulation according to the present invention is 5 mg/kg or more, preferably 10 mg/kg or more, more preferably 25 mg/kg or more, even more preferably 50 mg/kg or more.

The pharmaceutically or nutraceutically acceptable edible carrier materials, diluents or excipients preferably present in a (preferably pharmaceutical or nutraceutical) formulation according to the present invention are selected from the group consisting of starches (preferably obtained from corn, tapioca, cassava, rice, sago, potato, sweet potato, wheat, buckwheat, rye, oat, yam, chestnut, water chestnut, peas or beans), chemically modified starches (preferably chemically modified corn starch), degraded starches (preferably dextrins and/or maltodextrins (preferably obtained from corn, tapioca, cassava, rice, sago, potato, sweet potato, wheat, buckwheat, rye, oat, yam, chestnut, water chestnut, peas or beans (such as mung beans)), polydextrose (E-number E1200), pectins, hydrolyzed corn gluten, gums (preferably gum Arabic (acacia gum), gum traganth, gum ghatti, gum karaya, xanthan gum, gellan gum, guar gum), agar-agar, alginates (alginic acid and its pharmaceutically or nutraceutically acceptable salts), gelatins (preferably from cattle, chicken, fish and/or pig), carrageenan, cyclodextrins (preferably alpha-cyclodextrin, beta-cyclodextrin and/or gamma-cyclodextrin), silicon dioxide (silica, silica gel), talc, lactose, sorbitol, mannitol, xylitol, glucose (dextrose), sucrose, orally pharmaceutically or nutraceutically acceptable calcium salts, pharmaceutically or nutraceutically acceptable stearate salts, polyvinylpyrrolidones, propylhydroxybenzoates, celluloses and cellulose derivatives (preferably microcrystalline cellulose, methylcellulose, ethylcellulose, hydroxymethyl cellulose, hydroxyethyl cellulose, hydroxypropyl cellulose, hydroxyethyl methylcellulose, hydroxypropyl methylcellulose, carboxymethyl cellulose, sodium carboxymethyl cellulose), milk powders, nonfat dry milk, ethanol, glycerol, triacetin, polyethylene glycols, and fatty oils, (preferably selected from the group consisting of soy oil (soybean oil), olive oil, sunflower oil, safflower oil, corn oil, coconut oil, peanut oil, hazelnut oil, almond oil, walnut oil, palm kernel oil, pumpkin seed oil, canola oil (rapeseed oil), sesame oil, cottonseed oil, wheat germ oil, linseed oil, rice bran oil, MCT oils (medium-chain triglyceride oils), and fractionated coconut oils essentially consisting of fatty acid radicals containing 6 to 8 carbon atoms).

The total amount of pharmaceutically or nutraceutically acceptable, preferably orally consumable edible carrier materials, preferably at 25° C. and 1013 mbar solid carrier materials, is in the range of 5 to 95 wt. %, more preferably in the range of 20 to 95 wt. %, even more preferably in the range of 25 to 90 wt. %, in each case based on the total weight of the formulation.

In a preferred embodiment, one, several, or all pharmaceutically or nutraceutically acceptable, preferably orally consumable edible carrier materials are solid at 25° C. and 1013 mbar. Such carrier materials are particularly suitable to obtain (preferably pharmaceutical or nutraceutical) formulations according to the present invention in the form of capsules (e.g. hard gelatin capsules), tablets (non-coated and coated tablets, for example gastric juice-resistant coatings), dragées, granules, pellets, solid mixes, powders, for example for use as dietary supplements.

Preferably a (preferably pharmaceutical or nutraceutical) formulation according to the present invention comprises one or more pharmaceutically or nutraceutically acceptable edible carrier materials, diluents or excipients preferably selected from the group consisting of are silicon dioxide, guar gum, gum Arabic and maltodextrins. Maltodextrins having DE (Dextrose Equivalent) values in the range of from 5 to 35 are preferred in some formulations according to the present invention, maltodextrins having DE-values in the range of from 10 to 30 being more preferred, and maltodextrins having DE-values in the range of from 10 to 20 being particularly preferred. It is in this case not critical which plant originally provided the starch for producing the starch hydrolysates. Suitable and readily available are corn-based starches and starches made up of tapioca, rice, wheat or potatoes. Said pharmaceutically or nutraceutically acceptable edible carrier materials, diluents or excipients may simultaneously act as anticaking agent (flow auxiliary, for example in case silicon dioxide is used.

Preferably, a (preferably pharmaceutical or nutraceutical) formulation according to the present invention additionally comprises one or more emulsifiers, preferably selected from the group consisting of lecithins (preferably naturally occurring lecithins, particularly lecithin from egg or soy), phospholipids (preferably phosphatidylcholines), monoacylglycerols, and diacylglycerols, and/or one or more vitamins and the physiologically acceptable salts or esters thereof, preferably selected from the group consisting of vitamin A (preferably retinol), vitamin A palmitate, vitamin B1, vitamin B2 (riboflavin), vitamin B3 (niacin), vitamin B6, vitamin B9 (folic acid) vitamin B12, vitamin C, monosodium ascorbate, monopotassium ascorbate, calcium diascorbate, magnesium diascorbate, ascorbyl palmitate, ascorbyl stearate, vitamin D, and vitamin E, vitamin E acetate, vitamin E palmitate, vitamin H (biotin), and/or one or more flavoring agents, preferably one, two, three or more fresh, sweet, fruity, spicy and/or herbal flavoring agents, preferably selected from the group consisting of L-menthol, racemic menthol, menthone, isomenthone, peppermint oil, L-carvone, D-carvone, spearmint oil, cineol, *eucalyptus* oil, cinnamaldehyde (preferably trans-cinnamaldehyde), cinnamic alcohol, cinnamon bark oil, cinnamon leaf oil, methyl cinnamate, benzaldehyde, furfural, furfuryl alcohol, methyl salicylate, wintergreen oil, thyme oil, thymol, carvacrol, clove oil, camphene, p-cymene, alpha-terpinene, borneol, eugenol, anise oil, star anise oil, anethole (preferably trans-anethole), anisole, cis-3-hexenol, cis-3-hexenyl acetate, D-limonene, L-limonene, linalool, citral, geraniol, geranyl acetate, nerol, citronellol, citronellal, alpha-phellandrene, beta-phellandrene, alpha-pinene, beta-pinene, vanilla extract, vanillin, ethylvanillin, 2-hydroxy-4-methoxybenzaldehyde, 2,5-dimethyl-4-hydroxy-3(2H)-furanone, 2-ethyl-4-hydroxy-5-methyl-3(2H)-furanone, 2-ethyl-5-methyl-4-hydroxy-3(2H)-furanone, 5-ethyl-2-methyl-4-hydroxy-3(2H)-furanone, 3-hydroxy-4,5-dimethyl-2(5H)-furanone, maltol, ethylmaltol, coumarin, butyrolactone, gamma-undecalactone, gamma-nonalactone, 4-methyl-delta-lactone, massoia lactone, sotolon, delta-decalactone, tuberolactone, methyl sorbate, 2-hydroxy-3-methyl-2-cyclopentenones, n-butyl acetate, isoamyl acetate, ethyl propionate, ethyl butyrate, n-butyl butyrate, isoamyl butyrate, ethyl 3-methyl-butyrate, ethyl n-hexanoate, allyl n-hexanoate, n-butyl n-hexanoate, ethyl n-octanoate, ethyl-3-methyl-3-phenylglycidate, ethyl-2-trans-4-cis-decadienoate, 4-(p-hydroxyphenyl)-2-butanone, 1,1-dimethoxy-2,2,5-trimethyl-4-hexane, 2,6-dimethyl-5-hepten-1-al, and phenylacetaldehyde.

Preferably, one, two, three or more flavoring agents are sweet, fruity and/or spicy flavoring agents, preferably selected from the group consisting of trans-cinnamaldehyde, cinnamic alcohol, methyl cinnamate, benzaldehyde, furfural, furfuryl alcohol, camphene, p-cymene, alpha-terpinene, borneol, eugenol, trans-anethole, anisole, cis-3-hexenol, cis-3-hexenyl acetate, D-limonene, L-limonene, linalool, citral, geraniol, geranyl acetate, nerol, citronellol, citronellal, alpha-phellandrene, beta-phellandrene, alpha-pinene, beta-pinene, vanilla extract, vanillin, ethylvanillin, 2-hydroxy-4-methoxybenzaldehyde, 2,5-dimethyl-4-hydroxy-3(2H)-furanone, 2-ethyl-4-hydroxy-5-methyl-3(2H)-furanone, 2-ethyl-5-methyl-4-hydroxy-3(2H)-furanone, 5-ethyl-2-methyl-4-hydroxy-3(2H)-furanone, 3-hydroxy-4,5-dimethyl-2(5H)-furanone, maltol, ethylmaltol, coumarin, gamma-undecalactone, gamma-nonalactone, 4-methyl-delta-lactone, massoia lactone, sotolon, delta-decalactone, tuberolactone, methyl sorbate, n-butyl acetate, isoamyl acetate, ethyl propionate, ethyl butyrate, n-butyl butyrate, isoamyl butyrate, ethyl 3-methyl-butyrate, ethyl n-hexanoate, allyl n-hexanoate, n-butyl n-hexanoate, ethyl n-octanoate, ethyl-3-methyl-3-phenylglycidate, ethyl-2-trans-4-cis-decadienoate, 4-(p-hydroxyphenyl)-2-butanone, 2,6-dimethyl-5-hepten-1-al, and phenylacetaldehyde.

A (preferably pharmaceutical or nutraceutical) formulation according to the present invention preferably is selected from the group consisting of powders (preferably freeze-dried or spray-dried powders), dry beverages, fruit preparations (preferably fruit juice, fruit juice concentrate, fruit pulp and/or fruit puree containing food products, said fruit preparations preferably not being obtained from fruits from the genus *Amelanchier*; preferably pourable food products like beverages, milk shakes, fruit drink yoghurts), capsules (preferably hard capsules like hard gelatin capsules), confectionary bars (preferably soft bars, energy bars, granola bars), W/O-emulsions (preferably spreads and margarines), O/W-emulsions (spreads, yoghurts, yoghurt drinks, soy based drinks, flavored milk, fatty oil formulations (preferably comprising 10 wt. % or more of medium chain triglycerides (MCT oils) and/or vegetable oils).

The one or more compounds of formula (I), the compositions or plant extracts according to the present invention can also be comprised in confectioned formulations to be added to foodstuffs or food products (including beverages), e.g. in the form of powders or granules, e.g. freeze-dried or spray-dried, concentrates, solutions, dispersions or other instant form, or the like.

In one embodiment, preferably a composition or plant extract according to the present invention, or a (preferably pharmaceutical or nutraceutical) formulation according to the present invention (each as defined herein) at 25° C. and 1013 mbar are in solid form, more preferably in powdered form, particularly preferably in spray-dried form. With regard to spray drying, reference may be made to U.S. Pat. No. 3,159,585, U.S. Pat. No. 3,971,852, U.S. Pat. No. 4,532,145 or U.S. Pat. No. 5,124,162.

The invention relates to a (preferably pharmaceutical or nutraceutical) formulation, wherein said formulation is a fat based spread comprising a total amount of 10-85 wt. % of fat and a total amount of 10-90 wt. % of water, or a drink, especially a dairy based drink, wherein the drink comprises from 10 to 95 wt % of a dairy base such as cow milk, soy milk or yoghurt, especially preferable cow milk or yoghurt. Said (preferably pharmaceutical or nutraceutical) formulation comprising a total effective amount of one or more compounds of formula (I), a composition or a plant extract according to the present invention exhibits beneficial health properties and preferably still has an acceptable taste and/or color.

In a preferred embodiment, the one or more compounds of formula (I), the compositions or plant extracts according to the present invention are combined with one or more ingredients selected from the group consisting of lactic acid, lactose, sucrose, calcium salts (preferably calcium phosphate, calcium gluconate, calcium lactate, and calcium chloride), calcium oxide, magnesium salts, magnesium oxide, iron salts (preferably ferrous fumarate, ferrous succinate, iron sucrate-malate, iron fructate-malate, iron sucrate-citrate, iron fructatecitrate, iron sucrate-ascorbate, iron fructate-ascorbate, and mixtures thereof), vitamin A (particularly retinol (vitamin A1)), vitamin B6, vitamin B12, vitamin C, vitamin D, vitamin E, thiamine, niacin, biotin, riboflavin, pantothenic acid, phytic acid, daidzein, genistein, proteins (preferably casein, caseinates (preferably sodium caseinate), milk protein, milk protein hydrolyzate, milk protein isolate, whey protein, whey protein hydrolyzate, whey protein isolate, soy protein, soy protein hydrolyzate, soybean protein isolate), milk powder, soy powder, polyunsaturated fatty acids [preferably omega-3-, omega-6- and/or omega-9-fatty acids, preferably selected from the group consisting of docosahexaenoic acid (DHA, all-cis-docosa-4,7,10,13,16,19-hexaenoic acid), eicosatetraenoic acid (ETA, all-cis-8,11,14,17-eicosatetraenoic acid), eicosatetraenoic acid (ETA, all-cis-8,11,14,17-eicosatetraenoic acid), stearidonic acid (SDA, all-cis-6,9,12,15-octadecatetraenoic acid), docosapentaenoic acid (DPA; clupanodonic acid, all-cis-7,10,13,16,19-docosapentaenoic acid), linoleic acid, α-linolenic acid (all-cis-9,12,15-octadecatrienoic acid), and γ-linolenic acid], soy oil, butterfat, (refined) fish oil, algal oil, squid oil, flaxseed oil, grape seed oil, and triglycerides derived from the fatty acids myristic acid, palmitic acid and/or oleic acid, thereby forming preferred (preferably pharmaceutical or nutraceutical) formulations according to the present invention, particularly formulations suitable for oral consumption.

In a preferred embodiment, the (preferably pharmaceutical or nutraceutical) formulations according to the present invention, particularly dairy type formulations, are a fermented food product contain one or more edible bacteria, preferably $10^3$ or more, more preferably $10^5$ or more, particularly preferably $10^7$ or more edible bacteria per gram of formulation. Preferably, said edible bacteria are lactic bacteria.

Preferably, said one or more edible bacteria are selected from the group consisting of Bifidobacteria (preferably *Bifidobacterium animalis*, particularly *Bifidobacterium animalis animalis, Bidifobacterium animalis lactis, Bifidobacterium breve, Bifidobacterium bifidum, Bifidobacterium longum, Bidifobacterium infantis*), *Lactobacillus* spp. (preferably *Lactobacillus delbrueckii bulgaricus, Lactobacillus casei, Lactobacillus reuteri, Lactobacillus acidophilus, Lactobacillus helveticus, Lactobacillus plantarum*), *Lactococcus cremoris, Streptococcus thermophilus, Lactococcus lactis* and/or one or more bacteria of the genus *Leuconostoc*.

The (preferably pharmaceutical or nutraceutical) formulations according to the present invention are preferably suitable for enteral, particularly for oral administration, and can be in various forms, such as capsules, tablets (non-coated and coated tablets, for example gastric juice-resistant coatings, effervescent tablets), dragées, granules, pellets, solid mixes, suspensions, dispersions in liquid phases, emulsions, powders, solutions, semi-solids, pastes, syrups or as other swallowable or chewable products, for example as dietary supplements.

In a preferred embodiment, a (preferably pharmaceutical or nutraceutical) formulation according to the present invention comprises one or more, preferably two, three, four, five or more further additives, preferably selected from the group consisting of stabilizers, thickeners, coloring agents (preferably edible pigments or food dyes), bulking agents, polyols, preservatives (such as sodium or potassium benzoate, sodium or potassium sorbate), antioxidants (such as ascorbic acid, carotenoids, tocopherols, polyphenols), monosaccharides, disaccharides, oligo- or polysaccharides (such as soy-oligosaccharides, xylo-oligosaccharides, galacto-oligosacharides), non- or low-caloric sweeteners, bitterness blockers, acidifiers (preferably food acids such as citric acids, acetic acid, lactic acid, and adipic acid), artificial and/or natural flavors, emulsifiers, wetting agents (moisturizing agents), coating agents (preferably film forming agents), minerals, vegetable oils and fractions thereof, vegetable fats and fractions thereof, animal oils and fractions thereof, animal fats and fractions thereof and absorption promoting or delaying agents.

In a preferred embodiment, a (preferably pharmaceutical or nutraceutical) formulation according to the present invention suitable for oral administration is in solid form, preferably in the form of a capsule, non-coated tablet, coated tablet, effervescent tablet, dragée, granule, pellet, solid mixture or powder, and comprises one or more, preferably two or more additives selected from the group consisting of xylitol, sorbitol, mannitol, isomalt, maltitol, sucrose, lactose, fructose, glucose (dextrose), galactose, maltose, talc, silicon dioxide (preferably amorphous silica, pyrogenic silica, colloidal silica, crystalline silica, silica gel), creatine, alpha-lipoic acid, magnesium oxide, magnesium hydroxide, alkali or alkaline earth carbonates (preferably sodium carbonate), alkali or alkaline earth bicarbonates (preferably sodium bicarbonate), food acids, carbohydrate polymers (polysaccharides, polydextrose (E-number E1200), physically modified starches, chemically modified starches (preferably oxidized starch (E-number E1404), monostarch phosphate (E-number E1410), distarch phosphate (E-number E1412), phosphated distarch phosphate (E-number E1413), acetylated distarch phosphate (E-number E1414), acetylated starch (starch acetate esterified with acetic anhydride; E-number E1420), acetylated distarch adipate (E-number E1422), hydroxy propyl starch (E-number E1440), hydroxy propyl distarch phosphate (E-number E1442) starch sodium octenyl succinate (E-number E1450), acetylated oxidized starch (E-number E1451), and starch aluminium octenyl succinate (E-number E1501)), cyclodextrins (preferably alpha-cyclodextrin, beta-cyclodextrin and/or gamma-cyclodextrin), microcrystalline cellulose, methylcellulose, ethylcellulose, hydroxymethyl cellulose, hydroxyethyl cellulose, hydroxypropyl cellulose, hydroxyethyl methylcellulose, hydroxypropyl methylcellulose (hypromellose), carboxymethyl cellulose and its alkali or alkaline earth salts, gum Arabic (gum acacia), gum ghatti, carrageenan, guar gum, carob gum, alginates, pectins, inulin, xanthan gum, polyethylene glycols, N-vinyl-2-pyrrolidone homo- and copolymers, polyvinyl acetate homo- and copolymers, sodium stearyl fumarate, and magnesium stearate.

In a preferred embodiment, a (preferably pharmaceutical or nutraceutical) formulation according to the present invention for oral administration comprises one or more preservatives suitable for oral consumption by a mammal, particularly a human being, preferably selected from the group consisting of benzoic acid, benzoic acid sodium salt, benzoic acid potassium salt, benzoic acid calcium salt, propionic acid, salicylic acid, sorbic acid, sorbic acid sodium salt, sorbic acid potassium salt, sorbic acid calcium salt, ethyl para-hydroxybenzoate, sodium ethyl para-hydroxybenzoate, propyl para-hydroxybenzoate, sodium propyl para-hydroxybenzoate, methyl para-hydroxybenzoate, sodium methyl para-hydroxybenzoate, sulphur dioxide, sodium sulphite, sodium hydrogen sulphite, sodium metabisulphite, potassium metabisulphite, calcium sulphite, calcium hydrogen sulphite, biphenyl or diphenyl, orthophenyl phenol, sodium orthophenyl phenol, thiabendazole, nisin, natamycin or pimaracin, formic acid, sodium formate, calcium formate, hexamethylene tetramine or hexamine, formaldehyde, dimethyl dicarbonate, sodium nitrite, potassium nitrite, sodium nitrate, potassium nitrate, acetic acid, sodium acetates, e.g. sodium hydrogen acetate, potassium acetate, calcium acetate, ammonium acetate, lactic acid, propionic acid, sodium propinate, potassium propionate, calcium propionate, oric acid, sodium tetraborate (borax), invertase, and lysozyme.

In a preferred embodiment, a (preferably pharmaceutical or nutraceutical) formulation according to the present invention, preferably suitable for oral administration, comprises one or more food acids and/or the physiologically acceptable salts thereof. Preferably the food acids and the physiologically acceptable salts of food acids are selected from the group consisting of acetic acid, adipic acid, caffeotannic acid, citric acid, iso-citric acid, maleic acid, fumaric acid, galacturonic acid, glucuronic acid, glyceric acid, glycolic acid, lactic acid, malic acid, oxalic acid, pyruvic acid, quinic acid, succinic acid, tannic acid, tartaric acid, phosphoric acid, and the physiologically acceptable salts thereof, preferably the sodium, potassium and calcium salts thereof. In a more preferred embodiment, a (preferably pharmaceutical or nutraceutical) formulation according to the present invention, preferably suitable for oral administration, comprises one or more food acids or a physiologically acceptable salt thereof, selected from the group consisting of acetic acid, adipic acid, citric acid, maleic acid, fumaric acid, lactic acid, malic acid, oxalic acid, pyruvic acid, succinic acid tartaric acid, phosphoric acid, and the physiologically acceptable salts thereof, preferably the sodium, potassium and calcium salts thereof.

The flavor of an orally consumable formulation according to the present invention preferably is selected from the group consisting of berries, *citrus* fruits, pomaceous fruit, spices, herbs, mints, teas, coffeas, milk and/or milk products, and more particularly preferably selected from the group consisting of cola, lemon, lime, lemon-lime, grapefruit, orange, sweet orange, bitter orange, bergamot, mandarin, apple, pear, prickly pear, peach, apricot, fig, pineapple, prune, mango, melon, plum, kiwi, lychee, banana, cherry, sweet cherry, strawberry, raspberry, red currant, black currant, blackberry, blueberry, passion fruit, grape, pomegranate, acerola, vanilla, cinnamon, anise, fennel, clove, cardamom, tamarind, nutmeg, allspice, black pepper, honey, licorice, ginger ale, ginger, root beer, rose hip, green tea, red tea, rooibos tea, mate tea, honeybush tea, pu-erh tea, oolong tea, black tea, hibiscus tea, kombucha, milk, coffee, espresso, cocoa, chocolate (including whole milk chocolate, dark chocolate, white chocolate), hazelnut, walnut, almond, peppermint, spearmint, wintergreen and mixtures thereof.

A (preferably orally consumable) formulation according to the present invention preferably comprises one or more sweet-tasting substances, preferably in a sensorially effective amount, more preferably a sweet sensation imparting amount. Said sweet-tasting substances are preferably selected from the group consisting of sweet-tasting carbohydrates (preferably sucrose (saccharose), trehalose, lactose, maltose, melizitose, raffinose, palatinose, lactulose, D-fructose, D-glucose, D-galactose, L-rhamnose, D-sorbose, D-mannose, D-tagatose, D-arabinose, L-arabinose, D-ribose, D-glyceraldehyde) or vegetable preparations containing predominantly (>70 wt. %) or essentially consisting of these carbohydrates (e.g. from sugar beet (*Beta vulgaris* ssp., sugar fractions, sugar syrup, molasses), from sugar cane (*Saccharum officinarum* ssp., e.g. molasses, sugar syrups), from sugar maple (*Acer* ssp.), from agave (agave thick juice), synthetic/enzymatic hydrolysates of starch or sucrose (e.g. invert sugar syrup, highly enriched fructose syrups made from corn starch), fruit concentrates (e.g. from apples or pears, apple syrup, pear syrup), sweet tasting sugar alcohols (preferably glycerol, erythritol, threitol, arabitol, ribitol, xylitol, sorbitol, mannitol, dulcitol, lactitol), sweet tasting proteins (preferably miraculin, monellin, thaumatin, curculin, brazzein), high potency sweeteners (preferably magap, sodium cyclamate, acesulfame K, neohesperidin dihydrochalcone, saccharin sodium salt, aspartame, superaspartame, neotame, alitame, sucralose, stevioside, rebaudiosides, lugduname, carrelame, sucrononate, sucrooctate, monatin, phyllodulcin), certain sweet-tasting amino acids (preferably glycine, D-leucine, D-threonine, D-asparagine, D-phenylalanine, D-tryptophan, L-proline), and other sweet-tasting substances and sweet-tasting extracts, preferably selected from the group consisting of hernandulcin, dihydrochalcone glycosides, glycyrrhizin, glycyrrhetinic acid and its sweet tasting physiologically acceptable salts, preferably glycyrrhetinic acid ammonium salt, mogrosides, liquorice extracts (*Glycyrrhizza glabra* ssp.), *Lippia dulcis* extracts, *Momordica* ssp. extracts (in particular *Momordica grosvenori* [Luo Han Guo]), *Hydrangea dulcis* extracts and *Stevia* ssp. (e.g. *Stevia rebaudiana*) extracts.

A (preferably orally consumable) formulation according to the present invention additionally comprises lactose and/or maltose, and/or one or more sugar alcohols such as dulicitol, fucitol, maltitol, erythritol, isomaltitol (E953), lactitol (E966), maltitol, mannitol (E421), sorbitol (E420), xylitol (E967), and mixtures thereof.

A (preferably orally consumable) formulation according to the present invention may additionally comprise one or more high potency sweeteners are preferably selected from the group consisting of sodium cyclamate, acesulfame K, neohesperidin dihydrochalcone, saccharin, saccharin sodium salt, aspartame, superaspartame, neotame, alitame, sucralose, magap, lugduname, carrelame, sucrononate, sucrooctate, miraculin, curculin, monellin, mabinlin, thaumatin, curculin, brazzein, pentadin, or extracts or fractions of extracts obtained from natural sources containing said amino acids and/or proteins, neohesperidin dihydrochalcone, steviolgylcoside, stevioside, steviolbioside, rebaudiosides (preferably rebaudioside A, rebaudioside B, rebaudioside C, rebaudioside D, rebaudioside E, rebaudioside F, rebaudioside G, rebaudioside H, dulcoside, rubusoside), suavioside A, suavioside B, suavioside G, suavioside H, suavioside I, suavioside J, baiyunoside 1, baiyunoside 2, phlomisoside 1, phlomisoside 2, phlomisoside 3, phlomisoside 4, abrusoside A, abrusoside B, abrusoside C, abrusoside D, cyclocaryoside A and cyclocaryoside I, oslandin, polypodoside A, strogin 1, strogin 2, strogin 4, selligueanin A, dihydroquercetin-3-acetate, perillartine, telosmoside $A_{15}$, periandrin I-V, pterocaryoside, cyclocaryoside, mukuroziosode, bryoside, bryonoside, bryonodulcoside, carnosifloside, scandenoside, gypenoside, trilobatin, phloridzin, dihydroflavanol, hematoxylin, cyanin, albiziasaponin, telosmoside, gaudichaudioside, mogroside, hernandulcine, monatin, glycyrrhetin acid, glycyrrhizin, phyllodulcin, or the physiologically acceptable salts thereof, preferably the respective potassium, sodium, calcium or ammonium salts thereof, liquorice extracts (*Glycyrrhizza glabra* ssp.), *Lippia dulcis* extracts, *Momordica* ssp. extracts or individual substances (in particular *Momordica grosvenori* [Luo Han Guo] and the mogrosides obtained therefrom), *Hydrangea dulcis* or *Stevia* ssp. (e.g. *Stevia rebaudiana*) extracts or individual sweet tasting substances obtained from said extracts.

A (preferably orally consumable) formulation according to the present invention may more preferably additionally comprise one or more high potency sweeteners, preferably selected from the group consisting of aspartame, neotame, superaspartame, advantame, saccharin, sucralose (E955), cyclamate, acesulfam, monellin, stevioside, rebaudioside A, rebaudioside C, rebaudioside D, rubusosid, phyllodulcin, hernandulcin, thaumatin, brazzein, miraculin, glycyrrhizin, glycyrrhetinic acid, the physiologically acceptable salts (preferably the sodium, potassium or calcium salts) of these compounds.

Preferably, a (preferably orally consumable) formulation according to the present invention comprises one or more further constituents suitable for oral consumption, particularly one or more emulsifiers, preferably selected from the group consisting of lecithins (preferably naturally occurring lecithins, particularly lecithin from egg or soy), phospholipids (preferably phosphatidylcholines), monoacylglycerols, and diacylglycerols, and/or one or more antioxidants and optionally one or more substances for intensifying the antioxidative effect of said antioxidants, and/or one or more preservatives (preferably selected from the group consisting of benzoic acid, sodium benzoate, potassium benzoate, sorbic acid, sodium sorbate, sodium sorbate, butylated hydroxyanisole (BHA), and butylated hydroxytoluene (BHT)), preferably in a total amount of from 0.05 to 0.5 wt. %, more preferably of from 0.1 to 0.3 wt. %, based on the total weight of the formulation, and/or one or more vitamins and the physiologically acceptable salts or esters thereof, preferably selected from the group consisting of vitamin A, vitamin A1, vitamin A palmitate, vitamin A1 palmitate, vitamin B1, vitamin B2 (riboflavin), vitamin B3 (niacin), vitamin B6, vitamin B9 (folic acid) vitamin B12, vitamin C (ascorbic acid), monosodium ascorbate, monopotassium ascorbate, calcium diascorbate, magnesium diascorbate, ascorbyl palmitate, ascorbyl stearate, vitamin D, and vitamin E, vitamin E acetate, vitamin E palmitate, vitamin H (biotin), vitamin K, and/or one or more coloring agents, preferably selected form the group consisting of carotenoids (preferably carotenes (E-number E160a), preferably beta-carotene), xanthophylls (preferably lutein (E-number E161b), zeaxanthin (E-number E161h), zeaxanthin palmitate), paprika extract (E-number E160c), red beet juice powder (comprising betanine, beetroot red, E-number E162), annatto (E-number E160b), anthocyanins (E-number E163), chlorophylls (E-number E140), turmeric (E-number E100, comprising curcumin), tartrazine (FD&C Yellow No. 5, E-number E102), amaranth (E-number E123), titanium dioxide (E-number E171), iron oxides and iron hydroxides (E-number E172), erythrosine (E-number E127), caramel color (E-number E150, preferably E150d), FD&C yellow No. 6 (E-number E110), allura red (FD&C red No. 40, E-number E129), FD&C green No. 3 (fast green, E-number E143), FD&C blue No. 1 (brilliant blue, E-number E133) and FD&C blue No. 2 (indigotine, E-number E132), and/or one or more bitter tasting substances selected from the group consisting of quinine, neohesperidin, hesperidin, naringin, quercitrin, phloridzin, phloretin-2-O'-xyloglucoside, caffeic acid, limonoids (preferably limonin or nomilin from *citrus* fruits), lupolones from hops, humulones from hops, gallic and ellagic acid esters of carbohydrates (preferably pentagalloylglucose), catechins and epicatechins (preferably selected from the group consisting of galloylated catechins, galloylated epicatechins, gallocatechins or epigallocatechins, galloylated gallocatechins or galloylated epigallocatechins), theaflavins (in particular theaflavin, isotheaflavin, neotheaflavin), and galloylated theaflavins, and/or one or more (additional) solid stabilizers and/or thickeners.

Examples of stabilizers and/or thickeners which may be part of a (preferably orally consumable) formulation according to the present invention are preferably selected from the group consisting of carbohydrate polymers (polysaccharides, preferably starches, polydextrose (E-number E1200), physically modified starches, chemically modified starches (preferably oxidized starch (E-number E1404), monostarch phosphate (E-number E1410), distarch phosphate (E-number E1412), phosphated distarch phosphate (E-number E1413), acetylated distarch phosphate (E-number E1414), acetylated starch (starch acetate esterified with acetic anhydride; E-number E1420), acetylated distarch adipate (E-number E1422), hydroxy propyl starch (E-number E1440), hydroxy propyl distarch phosphate (E-number E1442) starch sodium octenyl succinate (E-number E1450), and acetylated oxidized starch (E-number E1451)), cyclodextrins, celluloses, modified celluloses (preferably methylcellulose, ethylcellulose, hydroxymethyl cellulose, hydroxyethyl cellulose, hydroxypropyl cellulose, hydroxyethyl methylcellulose, hydroxypropyl methylcellulose), gum Arabic (gum acacia), gum ghatti, gum tragacanth, gum karaya, carrageenan, guar gum, carob gum (carob flour, locust bean gum, E-number E410), alginates, pectins, inulin and xanthan gum.

Preferred stabilizers and/or thickeners are selected from the group consisting of starch sodium octenyl succinate, carboxymethyl cellulose, maltodextrin, polydextrose (E-number E1200), gum Arabic, guar gum, carob gum, alginates, pectin, and xanthan gum.

Preferably, an orally consumable formulation, in particular an orally consumable formulation for use as dietary or food supplement according to the present invention comprises one or more proteins, preferably selected from the group consisting of isolated soy protein, whey protein, caseinate, milk protein (particularly cow's milk protein), sunflower protein, safflower protein, linseed protein, almond protein, peanut protein, walnut protein, cottonseed protein, sesame protein. The total amount of proteins preferably is in the range of 3 to 60 wt. %, more preferably in the range of 5 to 50 wt. %, even more preferably in the range of 8 to 38 wt. %, particularly preferably in the range of 10 to 35 wt. %, in each case based on the total weight of the (preferably orally consumable) formulation. Preferably, such formulations are in solid form, preferably powdered form.

Preferably, an orally consumable formulation, in particular an orally consumable formulation for use as dietary or food supplement according to the present invention comprises one or more (further) fibers and/or flours, preferably selected from the group consisting of fruit fibers (preferably apple fiber, pear fiber, orange fiber, lemon fiber, banana fiber, grape fiber, date fiber, prune fiber), grain fibers (preferably oat fiber, barley fiber, wheat fiber, corn fiber, rye fiber), legume fibers (preferably bean fiber, pea fiber), avocado fiber, beet fiber, soy fiber, sesame flour, wheat flour, corn flour, rice flour, soy flour, and barley flour.

Preferably, a (preferably nutraceutical or pharmaceutical) formulation according to the present invention, in particular when used as food or dietary supplement, is administered orally prior to or at the start of a meal. The overall daily dosage should be based on the weight of the patient and the individual requirements, and thus may deviate to some extent from the daily dosages indicated hereinafter.

Preferably, a mixture, a composition, a plant extract, or a formulation each as defined herein in the context of the present invention is orally administered 1 second to 90 minutes, preferably 1 to 60 minutes, more preferably 2 to 50 minutes, most preferably 5 to 40 minutes, before food uptake, or during food uptake (i.e. uptake of a foodstuff, a food product, a meal, or the like).

Preferably, the amount of the one or more compounds of formula (I) in a (preferably nutraceutical (including food or dietary supplements) or pharmaceutical) formulation according to the present invention is such that—when administered to a patient—the total amount is effective in the inhibition of HMG-CoA reductase. Generally a total daily dose in the range of from 0.1 to 20 g is preferred, more preferred in the range of from 0.1 to 10 g. More preferably, the total daily dose is in the range of from 0.15 to 8 g, even more preferred in the range of from 0.2 to 5 g, and most preferably in the range of from 0.25 to 2.5 g. Preferably, the total daily dose is administered to a patient in one or more dosages, preferably in 1, 2, 3 or 4 dosages. These daily doses are calculated for a person weighing about 75 kg. The total daily dose may of course vary for patients with strongly differing weights, such as children. These patients should receive a correspondingly modified daily dose proportional to the patient's weight.

A mammal or human being, especially a "patient" or "individual" for the purposes of the present invention, includes especially human beings and further other mammals. Thus, the compound or extract comprising a compound of formula (I), respectively, or a mixture of compounds of formula (I), are applicable to both humans and animals. In the preferred embodiment the patient is a human.

The patients may be treated in prophylactic or therapeutic intention, thereby avoiding an unwanted increase of the cholesterol level, in particular of the LDL level, or reducing (lowering) an already elevated cholesterol level.

In a preferred embodiment, the plant extracts, the compositions or formulations according to the present invention are preferably formulated in a unit dosage from. The term "unit dosage form" refers to physically discrete units suitable as unitary dosages to be administered to mammals (preferably human beings), each unit containing a predetermined quantity of compounds of formula (I) (in pure form or in form of a mixture of compounds of formula (I), a composition according to the present invention, a plant extract according to the present invention, or (a preferably pharmaceutical or nutraceutical) formulation according to the present invention) effective to produce the desired prophylactic or therapeutic effect, preferably in combination with a suitable physiologically acceptable carrier.

The compound(s) of formula (I) as such, as mixtures, compositions or plant extracts as defined according to the present invention may be administered alone or in combination with other physiologically (e.g. pharmaceutically) active substances or drugs, i.e., anti-obesity agents, lipid-lowering agents or the like. Thus, the present invention also encompasses combinations comprising one or more compounds of formula (I), or a physiologically acceptable salt thereof, and one or more other drug compounds in free form or as physiologically acceptable salt, and optionally one or more physiologically acceptable carrier materials.

The overall daily dosage should be based on the weight of the patient and the individual requirements, and thus may deviate to some extent from the daily dosages indicated hereinafter.

Preferably, a composition, a plant extract or a (preferably pharmaceutical or nutraceutical) formulation according to the present invention is formulated as unit dosage form, preferably selected from the group consisting of granules, tablets, pills, capsules, pellets, and powders, wherein each unit dosage form preferably contains a total amount of 30 mg to 2500 mg, preferably from 50 mg to 1500 mg, more preferably from 75 mg to 1250 mg, particularly preferably from 100 mg to 1000 mg, and most preferably from 125 mg to 750 mg of the compounds of formula (I) for use according to the present invention.

If a composition, a plant extract or a (preferably pharmaceutical or nutraceutical) formulation according to the present invention is formulated as unit dosage form, preferably said unit dosage form is administered one time to ten times per day (24 h), more preferably one time to five times per day (24 h), even more preferably one time to three times per day (24 h).

The total amount of the compounds of formula (I) for use according to the present invention administered per individual or patient per day (24 h) preferably is in the range of 0.1 g to 16 g, more preferably from 0.25 g to 13 g, even more preferably from 0.4 g to 10 g, particularly preferably from 0.5 g to 8 g, and especially preferably from 0.5 g to 5 g.

The term "combination" does not necessarily mean a fixed combination but may also mean that the compound(s) of formula (I) may be administered in a chronologically staggered manner with the one or more combination partner substances, e.g. in the form of a kit of parts (which also is an embodiment of the present invention). Preferably, the chronologically staggered administration takes place such that the combination partners mutually influence, particularly intensify (e.g. by way of an additive or preferably synergistic effect), their therapeutic effects and/or efficiency.

Among other anti-obesity agents that may be combined, antilipidemics, e.g. atorvastatin, cerivastatin, fluvastatin, lovastatin, pravastatin, rosuvastatin, simvastatin, anti-obesity drugs, such as suppressants of the appetite, stimulators of the body's metabolism, or drugs or compositions interfering with the body's ability to absorb specific nutrients, such as sibutramine, diethylpropion, phendimetrazine, phentermine, fenfluramine, sibutramine, lipase inhibitors, such as orlistat; anorectics, such as dexedrine; cannabinoid receptor antagonists, such as rimonabant; acarbose; or the like, can be mentioned, without, however, limiting the possible combination partners. Other helpful drugs or active agents may be administered, e.g. psychoactive agents, agents that help in the treatment of addictive behaviour, especially in so far as they help to support the prophylaxis or treatment intended according to the present invention.

The compound(s) of formula (I), the plant extracts according to the present invention, the compositions according to the present invention, and the (preferably pharmaceutical or nutraceutical) formulations according to the present invention are particular useful for the prophylactic and/or therapeutic treatment of hypercholesterolemia.

The one or more compounds of formula (I) or a plant extract comprising one or more compounds of formula (I) (for use) according to the present invention can be obtained by extraction of the respective plant material(s), preferably by extracting plant material from the genus *Amelanchier.*

In another aspect, the present invention relates to a process for producing
(i) euscaphic acid, tormentic acid and/or myrianthic acid, or
(ii) a composition or plant extract according to the present invention as defined above, including the following steps:
(1) providing plant material from the genus *Amelanchier*, preferably from one or more species selected from the group consisting of *Amelanchier alabamensis, Amelanchier alnifolia, Amelanchier amabilis, Amelanchier amelanchier, Amelanchier andina, Amelanchier arborea, Amelanchier asiatica, Amelanchier australis, Amelanchier austromontana, Amelanchier bakeri, Amelanchier bartramiana, Amelanchier basalticola, Amelanchier beata, Amelanchier Canadensis, Amelanchier carrii, Amelanchier covillei, Amelanchier crenata, Amelanchier cuneata, Amelanchier cusickii, Amelanchier denticulate, Amelanchier elliptica, Amelanchier ephemerotricha, Amelanchier ephemerotricha* var. *silvicola, Amelanchier femaldii, Amelanchier florida, Amelanchier gaspensis, Amelanchier glabra, Amelanchier goldmanii, Amelanchier gormanii, Amelanchier gracilis, Amelanchier grandiflora, Amelanchier humilis, Amelanchier huronensis, Amelanchier integrifolia, Amelanchier interior, Amelanchier intermedia, Amelanchier japonica, Amelanchier laevis, Amelanchier lamarckii, Amelanchier leptodendron, Amelanchier leptosepala, Amelanchier lucida, Amelanchier macrocarpa, Amelanchier mormonica, Amelanchier mucronata, Amelanchier nantucketensis, Amelanchier neglecta, Amelanchier nervosa, Amelanchier nitens, Amelanchier oblongifolia, Amelanchier obovalis, Amelanchier oreophila, Amelanchier ovalis, Amelanchier pallida, Amelanchier paniculata, Amelanchier polycarpa, Amelanchier pringlei, Amelanchier prunifolia, Amelanchier pumila, Amelanchier quinti-martii, Amelanchier racemosa, Amelanchier recurvata, Amelanchier rotundifolia, Amelanchier rubescens, Amelanchier sanguinea, Amelanchier saxatilis, Amelanchier sinica, Amelanchier siskiyouensis, Amelanchier spicata, Amelanchier stolo-* nifera, *Amelanchier subintegra, Amelanchier turkestanica, Amelanchier ulmifolia, Amelanchier utahensis, Amelanchier venulosa, Amelanchier vestita, Amelanchier vulgaris* and *Amelanchier wiegandii*, (2) extracting the plant material provided in step (1), preferably with (i) a supercritical solvent, preferably carbon dioxide or fluorocarbons, preferably supercritical $CO_2$ or a mixture of supercritical $CO_2$ and one or more polarity modifiers, preferably supercritical $CO_2$ or a mixture of supercritical $CO_2$ and one or more polarity modifiers selected from the group consisting of methanol, ethanol, and isopropanol, wherein preferably the total amount of the polarity modifiers does not exceed 25 wt. %, based on the total weight of the solvent mixture, or (ii) a solvent or solvent mixture having a polarity characterized by an $E_T(30)$ value at 25° C. and 1 bar of 60 kcal/mol or lower, preferably in the range of 33 kcal/mol to 58 kcal/mol, (3) partially or fully removing the solvent used in extracting step (2), and (4) optionally carrying out further enrichment or isolation steps.

The one or more extraction steps are preferably performed using a solvent or solvent mixture with moderate polarity, i.e. being less polar than water, and more polar than n-hexane.

Preferably, the polarity of the solvent or solvent mixture has an $E_T(30)$ value of 58 kcal/mol or lower (at 25° C. and 1 bar (=$10^5$ Pa)), water has an $E_T(30)$ of 63.1. The $E_T(30)$ method is an empirical solvent polarity parameter, said method makes use of the stabilisation of the ground state of the betaine dye 2,6-diphenyl-4-(2,4,6-triphenyl-1-pyridinio) phenolate, CAS Registry Number 10081-39-7. Numerous $E_T(30)$ values have been reported in the literature for many different solvents and solvent mixtures, as for example summarized in Chem. Rev. 1994, 94, 2319-2358.

Preferably, the plant material used in step (1) comprises, essentially consists or consists of fruit (i.e. berry) material from species selected from the group consisting of *Amelanchier alnifolia, Amelanchier arborea, Amelanchier asiatica, Amelanchier bartramiana, Amelanchier basalticola, Amelanchier canadensis, Amelanchier confusa, Amelanchier denticulata, Amelanchier femaldii, Amelanchier humilis, Amelanchier interior, Amelanchier laevis, Amelanchier lamarckii, Amelanchier nantucketensis, Amelanchier obovalis, Amelanchier ovalis, Amelanchier pallida, Amelanchier pumila, Amelanchier sanguinea, Amelanchier sinica, Amelanchier spicata, Amelanchier stolonifera*, and *Amelanchier utahensis*, more preferably from *Amelanchier alnifolia, Amelanchier asiatica, Amelanchier laevis, Amelanchier lamarckii, Amelanchier nantucketensis, Amelanchier obovalis*, and *Amelanchier ovalis*.

Particularly preferably, the plant material used in step (1) comprises, essentially consists or consists of fruit (i.e. berry) material from *Amelanchier alnifolia* (*Amelanchier alnifolia* (Nutt.) Nutt. ex M. Roem.) and its subtaxa (preferably as listed in the following table).

| | |
|---|---|
| Species | *Amelanchier alnifolia* (Nutt.) Nutt. ex M. Roem. |
| Globally Unique Identifier | 721172-1 |
| Family | Rosaceae |
| Scientific | *Amelanchier canadensis* var. *alnifolia* (Nutt.) Torr. & A. Gray |
| Synonyms | *Amelanchier sanguinea* var. *alnifolia* (Nutt.) P. Landry |
| | *Aronia alnifolia* Nutt. |
| Subordinate Taxa | *Amelanchier alnifolia* fo. *alba* E.L. Nielsen |
| | *Amelanchier alnifolia* fo. *alnifolia* |
| | *Amelanchier alnifolia* var. *alnifolia* |
| | *Amelanchier alnifolia* var. *covillei* (Standl.) Jeps. |
| | *Amelanchier alnifolia* var. *cusickii* (Fernald) C.L. Hitchc. |
| | *Amelanchier alnifolia* var. *cuyamacensis* Munz |
| | *Amelanchier alnifolia* var. *dakotensis* E.L. Nielsen |
| | *Amelanchier alnifolia* subsp. *florida* (Lindl.) Hultén |
| | *Amelanchier alnifolia* var. *humptulipensis* (G.N. Jones) C.L. Hitchc. |
| | *Amelanchier alnifolia* var. *nitens* (Tidestr.) Munz |
| | *Amelanchier alnifolia* var. *oreophila* (A. Nelson) R.J. Davis |
| | *Amelanchier alnifolia* subsp. *pallida* (Greene) A.E. Murray |
| | *Amelanchier alnifolia* var. *pallida* (Greene) Jeps. |
| | *Amelanchier alnifolia* var. *pumila* (Torr. & A. Gray) C.K. Schneid. |
| | *Amelanchier alnifolia* var. *semiintegrifolia* (Hook.) C.L. Hitchc. |
| | *Amelanchier alnifolia* subsp. *siskiyouensis* (C.K. Schneid.) A.E. Murray |
| | *Amelanchier alnifolia* subsp. *subintegra* (Greene) A.E. Murray |
| | *Amelanchier alnifolia* var. *utahensis* (Koehne) M.E. Jones |
| | *Amelanchier alnifolia* var. *venulosa* (Greene) Jeps. |
| Common names | Saskatoon berry |
| | Saskatoon service berry |
| | Western service berry |
| | (Western) Juneberry |
| | (Erlenblättrige) Felsenbirne |

Preferably, in a process according to the present invention step (2) is performed comprising or consisting of the following steps (2-a), (2-b) and (2-c):

(2-a) extracting the plant material provided in step (1) with a solvent or solvent mixture having a polarity characterized by an $E_T(30)$ value at 25° C. and 1 bar in the range of 48 to 57 kcal/mol, preferably in the range of 50 to 56 kcal/mol, preferably selected from the group consisting of aqueous ethanol (i.e. a mixture essentially consisting of water and ethanol), preferably aqueous ethanol having an ethanol content of 60 vol. % or more, more preferably an ethanol content of 75 vol. % or more, and particularly preferably an ethanol content in the range of from 85 to 98 vol. %), ethanol, and methanol, (2-b) partially or fully removing the solvent or solvent mixture used in step (2-a), (2-c) optionally extracting the residue obtained in step (2-b) with a second solvent or solvent mixture, said second solvent or solvent mixture having an $E_T(30)$ value at 25° C. and 1 bar in the range of 33 to 47 Kcal/mol, preferably in the range of 35 to 46 Kcal/mol, more preferably in the range of 36 to 44 Kcal/mol, most preferably in the range of 37 to 42 Kcal/mol, and particularly preferably being selected from the group consisting of ethyl acetate, propyl acetate, butyl acetate, dimethyl carbonate, diethyl carbonate, ethyl benzoate, and triacetin.

When plant material (in particular fruit/berry material) from the genus *Amelanchier*, in particular from *Amelanchier alnifolia* (*Amelanchier alnifolia* (Nutt.), is used in step (1) of the process according to the present invention, particularly active and therefore preferred plant extracts according to the present invention are obtained, i.e. plant extracts exhibiting a strong HMG-CoA reductase activity in a mammal.

More specifically, the (particularly) preferred plant extracts and compositions according to the present invention defined and described in detail above are obtainable from *Amelanchier alnifolia* (*Amelanchier alnifolia* (Nutt.) using the (particularly) preferred production processes according to the present invention.

In another aspect the present invention therefore relates to a plant extract obtainable or obtained according to a process according to the present invention, in particular a plant extract obtainable or obtained according to a preferred or particularly preferred process according to the present invention, wherein preferably the plant material used in step (1) comprises, essentially consists or consists of fruit material from *Amelanchier alnifolia, Amelanchier asiatica, Amelanchier laevis, Amelanchier lamarckii, Amelanchier nantucketensis, Amelanchier obovalis*, and/or *Amelanchier ovalis*, more preferably the plant material used in step (1) essentially consists or consists of fruit material from *Amelanchier alnifolia*.

Preferred fruit materials to be used in an extraction process according to the present invention are whole fruits, fruit puree, fruit pulp, fruit concentrate, fruit mash, fruit pomace, fruit press cake, or mixtures thereof, each in wet, dry or frozen form.

In a preferred embodiment of the present invention, the fruits are dejuiced prior to the extraction step(s), and are preferably used in form of fruit mash, fruit pomace or fruit press cake, i.e. the remaining fruit material after pressing the fruit and removing the fruit juice, said remaining fruit material including fruit fibers, fruit pulp, fruit peel (skin) and fruit seeds, but lacking most of the fruit juice originally present in the fruits.

Preferably, dried or frozen plant material, in particular mash, pomace or press cake is used in the extraction step (of a process according to the present invention).

The respective plant material may be used without prior treatment or after treatment, such as drying, slicing, or the like. Prior to performing the extraction step(s) (according to the present invention), the plant material is preferably comminuted, e.g. via chopping, crushing, breaking, milling or grinding or combinations thereof.

Preferred plant material used in the context of the present invention comprises, essentially consists or consists of fruits (berries) from the genus *Amelanchier*, preferably comprises, essentially consists or consists of ripe fruits (berries) from the genus *Amelanchier*, preferably from *Amelanchier alnifolia*.

Preferred fruit materials to be used in an extraction process according to the present invention are whole berries, berry puree, berry pulp, berry concentrate, berry mash, berry pomace and/or berry press cake from *Amelanchier*, each in wet, dry or frozen form.

Auxiliary means such as (especially ultrasonic) sonication, warming/heating, and/or stirring, may be used to allow for appropriate extraction, enrichment and purification.

The extraction can be carried out at lower or elevated or ambient temperature, e.g. in the range from 0° C. to the boiling point of the solvent or solvent mixture employed, e.g. from ambient temperature (about 20° C.) to said boiling point. The extraction may be improved by moving the solvent and/or the plant material, e.g. by stirring, and/or by ultrasonication during extraction.

The compounds of formula (I), mixtures thereof or an extract comprising one or more of said compound for use according to the present invention can be obtained by extracting and subsequently preferably enriching (up to isolating) them from the corresponding plant materials.

Auxiliary means such as (especially ultrasonic) sonication, heating (e.g. extracting the plant material at temperatures in the range from 20° C. to 100° C., preferably up to a maximum of 60° C.), stirring, re-extraction, evaporation or the like, may be used to allow for appropriate extraction.

Additional further processing of the compositions or plant extracts according to the present invention is possible, e.g. by filtering (e.g. through paper, sintered glass, silica, charcoal (also allowing for decoloration).

Preferably, 90 wt. % or more, more preferably 95 wt. % or more, most preferably 98 wt. % or more of the total amount of plant material of the genus *Amelanchier* used in the extraction step (2) according to the present invention has a particle size of less than 20 mm, more preferably of 10 mm or less, even more preferably of 6 mm or less, particularly preferably of 4 mm or less, most preferably of 2 mm or less.

The compound(s) of formula (I), or an extract comprising one or more compound(s) of formula (I) are well soluble at 20° C. in organic solvents like alcohols, e.g. in ethanol. The solubility is generally 10 mg/ml or more, typically 50 mg/ml or more. Less polar solvents like hydrocarbons, medium-chain triglycerides (MCT) or vegetable oils are good solvents, whereas water is less appropriate solvent, e.g. the solubility is less than 1 mg/ml. Examples of appropriate solvents are organic solvents or solvent mixtures, e.g. a ketone and/or an ester, such as acetone and/or ethyl acetate, an ether, e.g. a cyclic ether such as dioxane, and/or (also in a specific embodiment) an alcohol e.g. ethanol, and/or a liquid or superfluid (supercritical) gas, especially superfluid $CO_2$.

In a preferred embodiment, in a process according to the present invention the solvent or solvent mixture used in step (2) is selected from the group consisting of supercritical $CO_2$ or a mixture of supercritical $CO_2$ and ethanol, wherein the amount of ethanol is in the range of from 1 to 20 wt. %, based on the total weight of the solvent mixture. More preferably, the extraction or one of the extraction steps is performed with mixture of supercritical $CO_2$ and 10 to 20 vol. % of ethanol, preferably at a pressure in the range of 150 to 600 bar, more preferably at 220 to 350 bar, at a temperature in the range of 25 to 90° C., more preferably in the range of 35 to 75° C.

The pH value of the extractant (i.e. the solvent or solvent mixture used in the extraction step) can be modified by adding acids (trifluoroacetic acid, acetic and formic acid) or ammonium acetate, respectively.

Preferably, the extracts can subsequently be further enriched by one or more additional purification steps, such as distribution, e.g. between an aqueous and an ether or ester (e.g. diethyl ether or ethyl acetate) phase for one or more times, precipitation (e.g. crystallisation) or especially chromatography, e.g. by HPLC or MPLC, by which it is possible to obtain further enriched extracts or isolated compounds of formula (I).

It is also possible to use other chromatographic methods such as gel permeation chromatography, countercurrent chromatography, or high speed counter current chromatography instead of the absorption chromatography described above.

Subsequent further purification or isolation may be carried out by preparative HPLC well-known to the person skilled in the art, e.g. using stationary phases such as RP8, RP18, phenyl, DIOL, C2, C4, C8 or amino. The mobile phase mixtures may also contain additional other acids (for example formic acid) or additional buffers (for example ammonium acetate).

The compound(s) of formula (I) can e.g. be isolated or the extracts prepared as described in the appended examples. The method for detection can comprise high pressure liquid chromatography (HPLC) or on reversed phase silica gel (C18) with water/acetonitrile-gradient as an elution solvent with UV as well as MS detection which are used for the product analysis and production optimization. It will be clear to those having ordinary skill in this art that the compound(s) of formula (I), though per se natural products, can alternatively be synthesized according to or in analogy to methods described in the literature.

Where "use" is mentioned, this especially refers to one or more of the following embodiments of the present invention which can be inserted wherever use is mentioned:

(1) A compound of formula (I), an extract comprising a compound of formula (I) or a mixture of compounds of formula (I), for use in therapeutic (including prophylactic) treatment of an animal, preferably a mammal, especially a human, against a disease, disorder or condition that responds to HMG-CoA reductase inhibiton, in particular a cholesterol disorder.

(2) A (preferably pharmaceutical or nutraceutical) formulation comprising a compound of formula (I), or a mixture of compounds of formula (I), as active ingredient together with a pharmaceutically or nutraceutically acceptable diluent or carrier, especially for use in the therapeutic and/or prophylactic treatment mentioned under (1).

(2') A (preferably pharmaceutical or nutraceutical) formulation for the treatment as mentioned under (1) comprising a compound of formula (I), or a mixture of compounds of formula (I), or especially a composition or plant extract comprising one or more compounds of formula (I), and a pharmaceutically or nutraceutically acceptable diluent or carrier, as active ingredient supplement to a food.

(3) A functional food comprising a compound of formula (I), or a mixture of compounds of formula (I), or especially a (preferably further enriched) extract, as active ingredient for the treatment as mentioned under (1).

(4) A method for the treatment as mentioned under (1), especially for the treatment of one or more cholesterol disorders, preferably selected from the group consisting of hypercholesterolemia, low HDL levels, high LDL levels, arteriosclerosis, and atherosclerosis, and/or for increasing the HDL/LDL ratio, in an individual in need of such treatment, comprising administering a (preferably pharmaceutically or nutraceutically) effective amount of one or more compounds of formula (I), as active ingredient, to an individual, especially to an individual in need thereof.

(5) The use of a compound of formula (I), or a mixture of compounds of formula (I), as active ingredient for the manufacture of a medicament or nutraceutical or (food or dietary) supplement for the treatment mentioned under (1).

(6) A method or use as defined under (4), comprising co-administration, e.g. concomitantly or in sequence, of a therapeutically effective amount of compound of formula (I), or a mixture of compounds of formula (I), as active ingredient and a different pharmaceutically active compound and/or a pharmaceutically acceptable salt thereof, said different pharmaceutically active compound and/or salt thereof being especially for use in the treatment as mentioned under (1).

(7) A combination product comprising a therapeutically effective amount of a compound of formula (I), or a mixture of compounds of formula (I), as active ingredient, and a different pharmaceutically active compound and/or a pharmaceutically acceptable salt thereof, said second pharmaceutically active compound being especially for use or of use in the treatment mentioned under (1).

The uses disclosed in the context of the present invention may also be for purely cosmetic purposes or generally for non-therapeutic use, where in all embodiments of the present invention, such as the above embodiments (1) to (7), "pharmaceutical", "pharmaceutically", "nutraceutical" and "nutraceutically" are replaced with "cosmetic" or "cosmetically", respectively, thus providing the corresponding embodiments for non-therapeutic use.

The (preferably pharmaceutical or nutraceutical) formulations according to the present invention may be sterilized and/or may contain further adjuvants such as preservatives, binders, disintegrants, moisturizing gents, skin or mucuous membrane penetration enhancers, emulsifiers, salts for varying the osmotic pressure and/or buffers, or other ingredients, excipients or carrier materials known in the art.

In a preferred embodiment, a composition or plant extract according to the present invention does not comprise euscaphic acid and tormentic acid in a ratio of 8.9:3.9 by weight.

In a preferred embodiment, a composition or plant extract according to the present invention does not comprise euscaphic acid, tormentic acid and myrianthic acid in a ratio of 8.9:3.9:4.3 by weight.

In a preferred embodiment, a (preferably pharmaceutical or nutraceutical) formulation according to the present invention does not comprise euscaphic acid and tormentic acid in a ratio of 8.9:3.9 by weight.

In a preferred embodiment, a (preferably pharmaceutical or nutraceutical) formulation according to the present invention does not comprise does not comprise euscaphic acid, tormentic acid and myrianthic acid in a ratio of 8.9:3.9:4.3 by weight.

Preferably, a composition or a plant extract according to the present invention (as defined above) comprises one, two or more unsaturated fatty acids with 18 carbon atoms, preferably with 18 carbon atoms (preferably linolenic acid, linoleic acid, and/or oleic acid), having one, two or three carbon-carbon double bonds, preferably in a total amount of 5 to 40 wt. % based on the total weight of the enriched extract, more preferably in a total amount of 10 to 30 wt. %.

Alternatively or additionally, in a composition or a plant extract according to the present invention (as defined above), preferably the ratio by weight of the total amount of unsaturated fatty acids with 18 carbon atoms having one, two or three carbon-carbon double bonds, (preferably of the total amount of linolenic acid, linoleic acid and oleic acid) to the total amount of the compounds of formula (I) is in the range of from 8:1 to 1:10, more preferably in the range of from 6:1 to 1:5, even more preferably in the range of from 4:1 to 1:3, particularly preferably in the range of from 3:1 to 1:2.

In a preferred embodiment, a composition according to the present invention and/or a plant extract according to the present invention does not comprise an effective amount of beta-sitosterol, and more preferably does not comprise an effective amount of phytosterols.

In a preferred embodiment, a composition according to the present invention and/or a plant extract according to the present invention comprises beta-sitosterol in an amount of 0 to 0.7 wt. %, preferably in an amount of 0 to 0.5 wt. %, more preferably in an amount of 0 to 0.2 wt. %, based on the total weight of said composition or said plant extract.

Preferably, the total amount of phytosterols and esters thereof, particularly of beta-sitosterol, campesterol, stigmasterol, brassicasterol, stigmastanol, campestanol, and the esters thereof, in a composition according to the present invention and/or a plant extract according to the present invention is less than 0.5 wt. %, more preferably less than 0.2 wt. %, even more preferably less than 0.1 wt. %, particularly preferably less than 0.05 wt. %, in each case based on the total weight of the composition or the plant extract.

In a preferred embodiment, in a composition according to the present invention and/or in a plant extract according to the present invention, the ratio by weight of the total amount compounds of formula (I) as defined above to the total amount of phytosterols and esters thereof, particularly of beta-sitosterol, campesterol, stigmasterol, brassicasterol, stigmastanol, campestanol, and the esters thereof, is greater than 50:1, more preferably greater than 75:1, even more preferably greater than 100:1, particularly preferably greater than 200:1, especially preferably greater than 300:1, and most preferably greater than 400:1.

If a formulation according to the present invention comprises one or more phytosterols (i.e. sterols/stanols) and/or $C_2$-$C_{22}$-fatty acid esters of phytosterols, the total amount of phytosterols and the $C_2$-$C_{22}$-fatty acid esters thereof, particularly of beta-sitosterol, campesterol, stigmasterol, brassicasterol, stigmastanol, campestanol, and the $C_2$-$C_{22}$-fatty acid esters thereof, preferably is in the range of 0.25 wt. % to 25 wt. %, more preferably in the range of 0.4 wt. % to 20 wt. %, even more preferably in the range of 0.6 wt. % to 15 wt. %, particularly preferably in the range of 0.7 wt. % to 12.5 wt. %, in each case based on the total weight of the formulation.

The preferred total amount of phytosterols and the $C_2$-$C_{22}$-fatty acid esters thereof, also depends on the form of the formulation according to the present invention.

For example, if the formulation according to the present invention is a non-frozen fermented or non-fermented dairy or dairy-based product (preferably a milk, a milk type drink, a drink yoghurt or a yoghurt), the total amount of phytosterols and the $C_2$-$C_{22}$-fatty acid esters thereof preferably is in the range of 3 wt. % to 22 wt. %, more preferably in the range of 4 wt. % to 18 wt. %, even more preferably in the range of 5 wt. % to 15 wt. %, and particularly preferably in the range of 8 wt. % to 12 wt. %, in each case based on the total weight of the formulation.

If the formulation according to the present invention is a spread (preferably a margarine, a butter product, or a mayonnaise), the total amount of phytosterols and the $C_2$-$C_{22}$-fatty acid esters thereof preferably is in the range of 0.2 wt. % to 8 wt. %, more preferably in the range of 0.3 wt. % to 5 wt. %, even more preferably in the range of 0.45 wt. % to 4 wt. %, and particularly preferably in the range of 0.6 wt. % to 2.5 wt. %, in each case based on the total weight of the formulation.

In a preferred embodiment, a composition according to the present invention and/or a plant extract according to the present invention does not comprise alpha-amyrin and/or beta-amyrin.

In a preferred embodiment, a composition according to the present invention and/or a plant extract according to the present invention does not comprise beta-sitosterol and/or beta-sitosterol-3-O-beta-D-glucopyranoside.

In a preferred embodiment, a composition according to the present invention and/or a plant extract according to the present invention does not comprise beta-sitosterol, 1-beta-hydroxyeuscaphic acid and/or oleanolic acid.

In a preferred embodiment, a composition according to the present invention and/or a plant extract according to the present invention does not comprise methyl betuliate, methyl maslinate, methyl corosolate, hoslunddiol, hoslundin and/or hoslundal.

In a preferred embodiment, a composition according to the present invention, a plant extract according to the present invention and/or a (preferably pharmaceutical or nutraceutical) formulation according to the present invention does not comprise gemin A, casuarinin, tellimagrandin II, potentillin and/or ellagic acid. In a preferred embodiment, a composition according to the present invention, a plant extract according to the present invention and/or a (preferably pharmaceutical or nutraceutical) formulation according to the present invention does not comprise gemin A, casuarinin, tellimagrandin II, and potentillin.

In a preferred embodiment, a composition according to the present invention and/or a plant extract according to the present invention does not comprise rosamultin (tormentic acid 28-beta-D-glucopyranosyl ester; CAS Registry Number 88515-58-6) and/or kaji-ichigoside $F_1$ (euscaphic acid 28-O-beta-D-glucopyranosyl ester).

In a preferred embodiment, a composition according to the present invention and/or a plant extract according to the present invention is free of beta-D-glucopyranosyl esters of a compound of formula (I) as defined above for use in accordance with the present invention.

In a preferred embodiment, a composition according to the present invention and/or a plant extract according to the present invention does not comprise tiliroside (CAS Registry Number 20316-62-5) and/or daucosterol (CAS Registry Number 474-58-8).

In a preferred embodiment, a composition according to the present invention and/or a plant extract according to the present invention does not comprise madecassic acid (CAS Registry Number 18449-41-7), madecassoside (CAS Registry Number 34540-22-2), maslinic acid (CAS Registry Number 4373-41-5), asiatic acid (CAS Registry Number 464-92-6), asiaticoside (CAS Registry Number 16830-15-2), taraxerol (CAS Registry Number 127-22-0), 2-alpha-hydroxyursolic acid, 23-hydroxyursolic acid, 23-hydroxy-tormentic acid-28-O-methyl ester and/or niga-ichigoside $F_1$ (CAS Registry Number 95262-48-9).

In a preferred embodiment, a composition according to the present invention and/or a plant extract according to the present invention is free of methyl betuliate, methyl maslinate, methyl corosolate, beta-sitosterol, beta-sitosterol-3-O-beta-D-glucopyranoside, alpha-amyrin, beta-amyrin, 1-beta-hydroxyeuscaphic acid, oleanolic acid, hoslunddiol, hoslundin and hoslundal.

In a preferred embodiment, a composition according to the present invention and/or a plant extract according to the present invention is free of rosamultin, kaji-ichigoside $F_1$, tiliroside, daucosterol, madecassic acid, madecassoside, maslinic acid, asiatic acid, asiaticoside, taraxerol, 2-alpha-hydroxyursolic acid, 23-hydroxyursolic acid, 23-hydroxy-tormentic acid-28-O-methyl ester and niga-ichigoside $F_1$.

In a preferred embodiment, a (preferably pharmaceutical or nutraceutical) formulation according to the present invention comprises beta-sitosterol in an amount of 1 wt. % or more, preferably of 2 wt. % or more, based on the total weight of the formulation.

In a further aspect, the present invention also relates to a composition or plant extract according to the present invention or formulation according to the present invention for use in the prophylactic and/or therapeutic treatment of a cholesterol disorder, preferably a disease, disorder or condition selected from the group consisting of hypercholesterolemia, low HDL levels, high LDL levels, arteriosclerosis, atherosclerosis, hyperlipemia, hyperlipidemia, hypertriglyceridemia and/or for increasing the HDL/LDL ratio.

The present invention also relates to a method of reducing the HMG-CoA reductase activity in a mammal, comprising the following step:
administering (preferably orally) to said mammal, preferably to a mammal (preferably a human being) in need of such treatment, a pharmaceutically or nutraceutically effective total amount of
- one or more compounds of formula (I) or formula (I-A) as defined above, preferably of a mixture of euscaphic acid and tormentic acid, wherein the ratio of euscaphic acid to tormentic acid by weight is greater than 1:1 (preferably equal to or greater than 2:1, more preferably equal to or greater than 5:2, even more preferably equal to or greater than 3:1, particularly preferably equal to or greater than 7:2, especially preferably in the range of 7:2 to 10:1), and most preferably in the range of 4:1 to 8:1, a composition according to the present invention (as defined above), or
- a composition or plant extract according to the present invention (as defined above), or
- a (preferably pharmaceutical or nutraceutical) formulation according to the present invention (as defined above).

The present invention also relates to a method of treating a disease, disorder or condition that responds to the modulation of the HMG-CoA reductase activity, comprising the following step:
administering (preferably orally) to said mammal, preferably to a mammal (preferably a human being) in need of such treatment, a pharmaceutically or nutraceutically effective total amount of
- one or more compounds of formula (I) or formula (I-A) as defined above, preferably of a mixture of euscaphic acid and tormentic acid, wherein the ratio of euscaphic acid to tormentic acid by weight is greater than 1:1 (preferably equal to or greater than 2:1, more preferably equal to or greater than 5:2, even more preferably equal to or greater than 3:1, particularly preferably equal to or greater than 7:2, especially preferably in the range of 7:2 to 10:1), and most preferably in the range of 4:1 to 8:1, a composition according to the present invention (as defined above), or
- a composition or plant extract according to the present invention (as defined above), or
- a (preferably pharmaceutical or nutraceutical) formulation according to the present invention (as defined above).

The present invention also relates to a method for producing a formulation according to the present invention as defined above, preferably in one of the preferred or particularly preferred embodiments including the following step:
mixing a compound of formula (I), preferably of formula (I-A), as defined above, or a composition or plant extract according to the present invention as defined above,
or
embedding a compound of formula (I), preferably of formula (I-A), as defined above, or a composition or plant extract according to the present invention as defined above in an enveloping or matrix material and subsequently mixing the resulting material,
with one, several or all further constituents of the said formulation.

EXAMPLES

The following Examples illustrate the present invention without limiting its scope. Unless indicated otherwise, all amounts, data and percentages relate to the weight.

The "Vanilla flavor A" (Madagascan vanilla type flavor) used in certain application examples as described hereinafter essentially consisted of diacetyl, acetic acid, acetoin, 1,3-butanediol, 2,3-butanediol, furfural, butyrolactone, furfuryl alcohol, benzaldehyde, p-hydroxybenzaldehyde, guaiacol, nonanal, eugenol, methyl cinnamate, and vanillin (1.70%, based on the total weight of "Vanilla flavor A").

The "Vanilla flavor B" (Tahitian vanilla type flavor) used in certain application examples as described hereinafter essentially consisted of diacetyl, acetic acid, isovaleraldehyde, pentanal, acetoin, hexanal, furfural, heptanal, benzaldehyde, methyl pyruvate, acetylfuran, octanal, limonene, nonanal, decanal, menthol, ethyl octanoate, methyl salicylate, dodecanal, anisaldehyde, anisyl alcohol, methyl-p-anisate, methyl cinnamate, maltol, vanillin (0.88%, based on the total weight of "Vanilla flavor B"), acetovanillone, and anisyl acetate.

General Experimental Procedures:

If not mentioned otherwise, chemicals are obtained in analytical grade from Merck (Darmstadt, Germany) or Sigma-Aldrich (Deisenhofen, Germany). The mobile phases are defined: A is water, B is acetonitrile.

HPLC-MS/UV/ELSD analyses were performed using an Agilent HP1100 (Agilent, Waldbronn, Germany) liquid chromatograph coupled with a LCT mass spectrometer (Waters GmbH, Eschborn, Germany) in the positive and negative electrospray ionization (ESI) mode. A Waters symmetry column (Waters Symmetry®) C18, 3.5 µm, 2.1 mm×150 mm, Waters GmbH, Eschborn, Germany) was used as stationary phase with a flow rate of 0.4 ml/min at 40° C. Mobile phases were acidified with 0.1% (v/v) formic acid; gradient: 0-1 min. 98% A, from 1-21 min to 100% B, from 21-27 min 100% B. The UV/Vis (ultraviolet/visible light) spectra were recorded between 200-500 nm, the HPLC-MS (Liquid Chromatography-Mass Spectrometry coupling) spectra were recorded in the range of molecular weights between 100 and 1.600 U.

Example 1

Preparation of an Enriched *Amelanchier alnifolia* Berry Extract 950 g of dried *Amelanchier alnifolia* berries (obtained from freshly collected berries in Sasketchewan, harvest season 2008) were powdered by using a laboratory mill and extracted for 30 minutes at room temperature with 1600 ml of 70 vol. % ethanol twice using ultrasonic irradiation. The resulting supernatant was separated from the remaining material and concentrated under reduced pressure. The remaining aqueous phase was adjusted with water to a final volume of 750 ml and was extracted two times with 750 ml ethyl acetate by liquid/liquid separation. The organic phases were combined and the organic solvents evaporated under reduced pressure. The resulting residue was then freeze-dried and the amount of the resulting dry extract was determined. Typical yields were about 5.4 g which typically contained about 4% of euscaphic acid, 1% of tormentic acid, 1% of myrianthic acid, 15% of ursolic acid, 3% of corosolic acid, 15% in total of caffeoylquinic acids, 20% in total of quercetin and quercetin mono-glycosides (mainly quercetin 3-O-beta-D-galactopyranoside), 15% of sugars and sugar alcohols, and 25% in total of linolenic acid, linoleic acid, and oleic acid.

Example 2

Preparation of an Enriched *Amelanchier alnifolia* Berry Pomace Extract 100 g of wet *Amelanchier alnifolia* berry pomace (obtained from freshly collected berries in Sasketchewan, harvest season 2011) were extracted for 30 minutes at room temperature with 600 ml of 70 vol. % ethanol twice using ultrasonic irradiation. The resulting supernatant was separated from the remaining material and concentrated under reduced pressure. The remaining aqueous phase was adjusted with water to a final volume of 250 ml and was extracted two times with 250 ml ethyl acetate by liquid/liquid separation. After evaporation of the organic solvents under reduced pressure, the resulting residue was freeze-dried and the amount of the dry extract determined. Typical yields were about 370 mg of dry extract containing 10% of euscaphic acid, 2% of tormentic acid, 2% of myrianthic acid, 2% of ursolic acid, 2% of corosolic acid, 15% in total of caffeoylquinic acids, 24% in total of quercetin and quercetin mono-glycosides (mainly quercetin 3-O-beta-D-galactopyranoside), 5% of sugars and sugar alcohols, and 25% in total of linolenic acid, linoleic acid, and oleic acid.

Example 3

Isolation of Euscaphic Acid

Four liquid chromatography steps were optimised for purification of euscaphic acid. All purification steps were performed at room temperature (about 20° C.) on a preparative HPLC system (Gilson Abimed, Ratingen, Germany), comprising Gilson Unipoint software, 305 or 306 binary pump system, 204 fraction collector, 155 UV-Vis detector, 806 manometric module, and 811C dynamic mixer, using gradients and stationary phases as described below. A total of 4.8 g of the dry extract obtained according to example 1 were separated on a reversed phase material by medium pressure liquid chromatography on a Chromabond® (Trademark by Machery-Nagel GmbH & Co. KG, Düren, Germany) 100-20 C18ec column, 130×40 mm, (Macherey & Nagel) with a flow rate of 20 ml/min whereas the fractions were collected each minute using the following binary gradient and solvents, which were acidified with 0.1 vol. % of trifluoric acid (TFA): begin 10% (v/v) B, 60 min 70% (v/v) B, 70 min 100% (v/v) B. The signals were detected at 210 nm and 254 nm. The separation was performed with a pressure of 4 bar at room temperature. The resulting fractions were analysed by analytical HPLC-MS/UV/ELSD.

Fractions containing euscaphic acid were combined. Euscaphic acid elutes after 38-73 minutes. A typical yield of this fraction was 243 mg. The second purification step for euscaphic acid was performed at 40° C. with a pressure of 130 bar on a Nucleodur 100-5 C18 column (250×21 mm, Macherey & Nagel) with a flow rate of 20 ml/min whereas the fractions were collected each half minute using following gradient and solvents, which were acidified with 0.1% (v/v) TFA: begin 40% (v/v) B, 30 min 60% (v/v) B, 35 min 100% (v/v) B, 45 min 100% (v/v) B. The signals were detected at 210 nm and 254 nm. Euscaphic acid eluted typically in the range of 12-32 minutes. A typical yield of the procedure was 70 mg enriched fraction. The next purification step was performed at 40° C. with a pressure of 130 bar on a Nucleosil 100-7 C18 column (250×10 mm, Macherey & Nagel) with a flow rate of 8 ml/min whereas the fractions were collected each half minute using following gradient and solvents, which were acidified with 0.1% (v/v) TFA: begin 40% (v/v) B, 30 min 50% (v/v) B, 35 min 100% (v/v) B, 50 min 100% (v/v) B. The signals were detected at 210 nm and 254 nm. Euscaphic acid eluted typically in the range of 25-49 minutes. A typical yield of the procedure was 30 mg enriched fraction. The final purification step for euscaphic acid was performed at room temperature with a pressure of 3 bar on a LiChrogel PS1 gel filtration (250×25 mm, Merck) with a flow rate of 4 ml/min whereas the fractions were collected each minute using 100% Acetonitrile as solvent. The signals were detected at 210 nm and 254 nm. Euscaphic acid eluted typically in the range of 43-49 minutes. This procedure typically yielded 3.0 mg of euscaphic acid. The structure was elucidated by NMR according to literature data (Numata et al, Chem. Pharm. Bull. 1989, 648). NMR spectra were recorded in DMSO-$d_6$ on a Bruker Avance spectrometer at 300 K, operating at 500.13 MHz proton frequency. The residual solvent signal was used for internal calibration ($\delta_C$ 39.5; $\delta_H$ 2.50). Peak assignment and structure elucidation was done on basis of 1D NMR spectra ($^1$H NMR) and 2D NMR correlations ($^1$H,$^1$H-gCOSY, $^1$H,$^{13}$C-gHSQC, $^1$H,$^{13}$C-gHMBC spectra).

Example 4

HMG-CoA Reductase Inhibition Test

Inhibition of HMG-CoA reductase was determined under following conditions. Human recombinant HMG-CoA reductase were pre-incubated with 35 ng/ml enzyme in reaction buffer, pH 7.5 (100 mM $KH_2PO_4$, 8 mM Glucose-6-Phosphate, 1 mM nicotinamide adenine dinucleotide phosphate, 4 mM ethylenediaminetetraacetic acid, 2 mM dithiothreitol, 0.6 Units glucose-6-phosphate dehydrogenase) for 15 minutes at 37° C. The reaction was initiated by addition of 2.5 µM [14C]HMG-CoA for another 20 minute incubation period and terminated by further addition of 1 N HCl. An aliquot was removed and then counted to determine the amount of [14C]Mevalonate formed. Lovastatin was used as positive control and inhibits HMG-CoA reductase with an $IC_{50}$ value of 74 nm. All samples were measured in duplicates.

TABLE E1

Results of the HMG-CoA reductase inhibition assay

| Test sample | Inhibition of HMG-CoA reductase at [30 µM] | Inhibition of HMG-CoA reductase at [3 µM] |
|---|---|---|
| Euscaphic acid | Not measured | 91% |
| Extract of example 1 | 92% | 72% |
| Barbinervic acid | 37% | Not measured |
| Pomolic acid | 25% | Not measured |
| Ursolic acid | 0% | 0% |
| Quercetin-3-O-beta-D-galactopyranoside | Not measured | 75% |
| Lovastatin | 100% | 100% |

Example 5

In Vivo Food Cholesterol Reduction

The dry extract of example 1 was evaluated for possible hypocholesterolemic activity in hamsters fed with a high-cholesterol diet. Groups of 10 male golden Syrian hamsters were induced to hypercholesterolemia by a high cholesterol diet (g/100 g: 5.0 corn oil, 5.0 coconut oil, 0.2 cholesterol and 89.8 standard diet throughout the 28-day experimental period. After the test animals had been kept on the high cholesterol diet for 7 days, vehicle (1% Cremophor EL in phosphate buffered saline) and extract of example 1 (incorporated into said vehicle) were administered orally, starting on day 1, for 28 days at 100 mg/kg, once a day, were administered orally for 28 consecutive days. Ezetimibe, the positive control, was also administered orally (at 1 mg/kg) for 28 consecutive days. Blood was drawn in overnight fasted animals on day 1 (pre-treatment), day 8, day 15, and day 29 for measurements of serum total cholesterol (Total plasma cholesterol), high density lipoprotein (HDL), low density lipoprotein (LDL) and triglyceride (TG) levels. The measurement values on day 8, day 15, day 22 and day 29 were transformed into percentage. One-way ANOVA and Dunnett's test were used to ascertain difference between vehicle control and treated groups.

TABLE E2

Effects on total plasma cholesterol. The percentage (%) indicates the total plasma cholesterol levels relative to day one (pre-treatment).

| Group | Total plasma cholesterol | | |
| --- | --- | --- | --- |
| | t = day 1 | t = day 15 | t = day 29 |
| Vehicle group | 100% | 137% | 155% |
| Extract group | 100% | 129% | 134%* |
| Ezetimibe | 100% | 61%* | 41%* |

*$p < 0.05$ indicates significant activity

TABLE E3

Effects on LDL. The percentage (%) indicates the LDL levels relative to day one.

| Group | LDL | | |
| --- | --- | --- | --- |
| | t = day 1 | t = day 15 | t = day 29 |
| Vehicle group | 100% | 263% | 373% |
| Extract group | 100% | 214% | 280%* |
| Ezetimibe | 100% | 22%* | 15%* |

*$p < 0.05$ indicates significant activity

Example 6

Preparation of an Enriched *Amelanchier alnifolia* Berry Pomace Extract 100 g of freeze-dried and powdered *Amelanchier alnifolia* berry pomace obtained from freshly collected berries around Saskatoon in 2011 were extracted for 3 hours at room temperature with 500 ml 98 vol. % ethanol under continuous stirring conditions. The resulting supernatant was separated from the remaining material and concentrated under reduced pressure. About 14.3 g of extract were obtained containing about 14% of euscaphic acid, 4% of tormentic acid, 1% of myrianthic acid, 18% of ursolic acid, 4% of corosolic acid, 2% in total of caffeoylquinic acids, a total of 2% of quercetin and quercetin 3-O-beta-D-galactopyranoside, 25% of sugars and sugar alcohols, and a total of 24% of fatty acids and fats (including 1% linolenic acid and 1% oleic acid).

Example 7

Preparation of an Enriched *Amelanchier alnifolia* Berry Pomace Extract 92.8 g of freeze-dried and powdered *Amelanchier alnifolia* berry pomace obtained from freshly collected berries in Sasketchewan in 2011 were extracted for 3 hours at room temperature with 1100 ml 96 vol. % ethanol under continuous stirring conditions. The resulting supernatant was separated from the remaining material and concentrated under reduced pressure. About 20.2 g of extract were obtained containing about 9% of euscaphic acid, 3% of tormentic acid, 1% of myrianthic acid, 12% of ursolic acid, 3% of corosolic acid, 2% in total of caffeoylquinic acids, a total of 2% of quercetin and quercetin 3-O-beta-D-galactopyranoside, 40% of sugars and sugar alcohols, and a total of 26% of fatty acids and fats (including 16% linolenic acid and 4% oleic acid).

Example 8

Preparation of a Supercritical Fluid *Amelanchier alnifolia* Berry Pomace Extract 1700 g of freeze-dried and powdered *Amelanchier alnifolia* berry pomace (obtained from freshly collected berries in Sasketchewan in 2011) were placed in the extraction vessel of the supercritical fluid extraction (SFE) apparatus. Extraction with 15 vol. % ethanol as co-solvent in supercritical fluid $CO_2$ was operated with a flow rate of 100 g/min at 290 bar and 60° C. About 153.8 g of extract were recovered after desolvatization. The extract contains about 16% of euscaphic acid, 5% of tormentic acid, 1% of myrianthic acid, 38% of oleanolic acid acid, 3% of corosolic acid, 1% in total of quercetin and quercetin mono-glycosides (mainly quercetin 3-O-beta-D-galactopyranoside), 3% of sugars and sugar alcohols, and 30% in total of linolenic acid, linoleic acid, oleic acid and other fatty acids.

Application Example F1

Spray-Dried Extract in Powder Form

| Ingredient | A wt. % | B wt. % | C wt. % | D wt. % |
| --- | --- | --- | --- | --- |
| Dried extract of Example 6 | 15 | — | — | — |
| Dried extract of Example 7 | — | 10 | — | — |
| Dried extract of Example 2 | — | — | 20 | — |
| Euscaphic acid, tormentic acid and myrianthic acid (14:5:1) (w/w/w) | — | — | — | 4.5 |
| Maltodextrin (DE = 18) | — | — | Ad 100 | — |
| Maltodextrin and gum Arabic (10:1) | Ad 100 | Ad 100 | — | Ad 100 |
| Lactose and glucose (1:2) | — | — | — | 6 |
| Zeaxanthin (E-number E161h) | — | 0.1 | — | 0.06 |
| Beta-carotene | — | — | — | 0.05 |

The constituents are dissolved in a mixture of ethanol and demineralized water and subsequently spray-dried to give a free flowing powder.

Application Examples F2 to F5

Example F2=Instant drink powder
Example F3=Instant drink powder, sugar-reduced
Example F4=Carbonated lemonade (soft drink)
Example F5=Soy fruit drink

| | F2 | F3 | F4 | F5 |
| --- | --- | --- | --- | --- |
| Dried extract of Example 6 | 4.50 | — | — | 2.35 |
| Euscaphic acid and tormentic acid (3:1) (w/w) | — | 20.00 | 0.95 | 0.50 |

|  | F2 | F3 | F4 | F5 |
|---|---|---|---|---|
| Sucrose (saccharose) | Ad 100 | 22.00 | 9.00 | 8.50 |
| Citric acid | 4.00 | 22.33 | 0.20 | — |
| Trisodiumcitrate | 0.26 | — | — | — |
| Tricalciumphosphate | 0.22 | — | — | — |
| Ascorbic acid (vitamin C) | 0.24 | 0.42 | — | — |
| Titanium dioxide (E-number E171) | 0.20 | — | — | 0.10 |
| Xanthan gum (E-number E415) | 0.072 | — | — | — |
| Sodiumcarboxymethylcellulose (E467) | 0.064 | — | — | — |
| Pectin (E440) | 0.04 | — | — | — |
| Spray-dried pineapple flavor, containing yellow colorant tartrazine | 0.50 | — | — | — |
| Spray-dried vanilla flavor A (85% carrier material) | 0.65 | — | — | — |
| Spray-dried raspberry flavor (containg raspberry ketone and red colorant) | — | 10.25 | — | — |
| Lemon-peach flavor | — | — | 0.01 | — |
| D-Limonene | — | — | 0.005 | — |
| Maltodextrin (powder, DE 15) | — | Ad 100 | — | — |
| Aspartame | — | 3.00 | — | — |
| Vanilla flavor B | — | — | — | 0.10 |
| Vanillin | — | — | 15 ppb | — |
| 2,5-dimethyl-4-hydroxy-2H-furan-3-one | — | — | 3 ppb | — |
| Sotolon | — | — | 10 ppb | — |
| Maltol | — | — | 300 ppb | — |
| Mixture of fruit juice concentrates | — | — | — | 25.00 |
| Soy powder | — | — | — | 6.00 |
| Drinking water | — | — | Ad 100 | Ad 100 |

The compositions of examples F2 and F3 are ready-to-drink beverage compositions after dissolution in an appropriate amount in tap water or mineral water. The lemonade of example F4 is carbonated with 4 volumes of carbon dioxide after filling into bottles.

Application Example F6

Ready-to-Drink Beverage

| Ingredient | A in wt. % | B in wt. % | C in wt. % |
|---|---|---|---|
| Sugar syrup, 71.7° Brix | 12.50 | 9.00 | 10.00 |
| Citric acid, anhydrous | 0.25 | 0.235 | 0.235 |
| Sodium benzoate | 0.16 | 0.10 | 0.10 |
| Potassium sorbate | — | 0.13 | 0.13 |
| Ascorbic acid | 0.14 | 0.15 | 0.15 |
| Lemon oil, cold pressed | 0.08 | — | — |
| Orange oil, cold pressed | 0.02 | 0.09 | 0.09 |
| FD&C Yellow 5 | 0.003 | 0.007 | 0.007 |
| FD&C blue No. 1 | 0.006 | 0.004 | — |
| Rebaudioside A | — | 0.005 | 0.005 |
| Dried extract of Example 1 | 2.65 | — | — |
| Dried extract of Example 6 | — | 1.35 | — |
| Dried extract of Example 8 | — | — | 1.10 |
| Tap water | Ad 100 | Ad 100 | Ad 100 |

Application Example F7

Ready-to-Drink Flavored Milk

| Ingredient | A in wt. % | B in wt. % | C in wt. % |
|---|---|---|---|
| Sucrose | 7.50 | 8.20 | 8.20 |
| Glucose | — | 0.50 | 0.50 |
| Fructose | 0.50 | — | — |
| Mango-peach flavor | 0.90 | — | — |
| Strawberry-banana flavor | — | 1.00 | 1.00 |
| Dried extract of Example 6 | 1.40 | — | — |
| Dried extract of Example 7 | — | 1.90 | — |
| Product D from Application Example F1 | — | — | 3.10 |
| UHT-milk (1.5 wt. % fat) | Ad 100 | Ad 100 | Ad 100 |

Application Example F8

Frozen Yoghurt Desserts

| Ingredient | A in wt. % | B in wt. % | C in wt. % | D in wt. % | E in wt. % |
|---|---|---|---|---|---|
| Plain yoghurt* | Ad 100 | Ad 100 | Ad 100 | Ad 100 | Ad 100 |
| Sucrose | 3.00 | — | 11.00 | — | 4.00 |
| Maltitol | — | 3.00 | — | — | 5.00 |
| Isomalt | — | 3.00 | — | 4.00 | — |
| Raspberry puree (flash pasteurized) | 31.50 | 25.00 | — | — | 28.00 |
| Mango puree (flash pasteurized) | — | — | 22.00 | 10.00 | — |
| Passion fruit and pineapple puree | — | — | — | 21.50 | — |
| Apple juice concentrate (64 wt. % dry matter) | — | 12.00 | — | — | 4.50 |
| Rapeseed oil** | — | — | — | — | 3.80 |
| Dried extract of Example 6 | 1.20 | — | — | 2.30 | 3.80 |
| Dried extract of Example 1 | — | 2.25 | 3.00 | — | — |

*The commercially available plain yoghurt used contained skimmed milk, concentrated or powdered skimmed milk, lactose, milk proteins, and yoghurt lactic ferments. Nutritional information: the plain yoghurt consisted of 1 wt. % of fats, 6.8 wt. % of carbohydrates, 3.8 wt. % of proteins and 88.4 wt. % of water and minerals.
**The commercially available rapeseed oil contained 60% of oleic acid, 21% of linoleic acid, 10% of alpha-linolenc acid, 4% of palmitic acid and 2% of stearic acid.

The cold fruit puree(s) are first mixed with the dried extract from Example 6 or Example 7. Then, sucrose, sugar alcohol(s), apple juice concentrate and/or rapeseed oil as indicated above are added thereto, and the respective resulting mixture is subsequently combined with the yoghurt (4° C.). The resulting mixture is transferred into a container for a Pacojet™ ice cream maker, closed by a lid and then frozen until the core temperature reached about −28° C.

Application Example F9

Frozen Yoghurt Desserts

| Ingredient | A in wt. % | B in wt. % | C in wt. % | D in wt. % |
|---|---|---|---|---|
| Plain cream yoghurt* | Ad 100 | — | Ad 100 | Ad 100 |
| Plain Bio yoghurt** | — | Ad 100 | — | — |
| Vanilla flavor A | 0.10 | — | 0.10 | 0.10 |
| Sucrose | 8.50 | 6.00 | 11.00 | 8.50 |

-continued

| Ingredient | A in wt. % | B in wt. % | C in wt. % | D in wt. % |
|---|---|---|---|---|
| Blueberry puree | 31.60 | — | — | 31.60 |
| Mango puree (flash pasteurized) | — | 31.00 | 29.00 | — |
| Dried extract of Example 6 | 0.80 | 1.40 | — | — |
| Dried extract of Example 2 | — | — | 2.90 | — |
| Product D from Application Example F1 | — | — | — | 4.00 |

*The commercially available plain cream yoghurt used contained whole milk, cream, concentrated or powdered skimmed milk and yoghurt lactic ferments. Nutritional information: the plain cream yoghurt contained 9 wt. % of fats, 4.3 wt. % of carbohydrates, 3.2 wt. % of proteins and more than 83 wt. % of water and minerals.
**The commercially available plain Bio yoghurt used contained whole milk, powdered skimmed milk and lactic ferments including Bifidobacterium. Nutritional information: the plain Bio yoghurt contained 3.4 wt. % of fats, 5 wt. % of carbohydrates, 3.7 wt. % of proteins and more than 87.5 wt. % of water and minerals.

The respective cold yoghurt (4° C.) is first mixed with the dried extract from Example 6 or Example 2. Then, sucrose and optionally vanilla flavor are added thereto, and the respective resulting mixture is subsequently combined with the respective cold fruit puree as indicated above. Then, each mixture is transferred into a container for a Pacojet™ ice cream maker, closed by a lid and then frozen until the core temperature reached about −28° C.

Application Example F10

Yoghurts with Improved Health Benefits

To 250 g of powdered whole milk was added water to make a total of 1200 g, the mixture was homogenized at 150 bar and sterilized by heating at 125° C. for 5 seconds, and then cooled to 37° C. Then it was inoculated with 1% of a starter of *Lactobacillus acidophilus* and 1% of a starter of *Bifidobacterium breve* and cultured at 37° C. until the pH-value of the culture reached 5.2.

Syrup A: 35 g of sucrose and 40 g of maltose were dissolved in 175 g sterilized drinking water.

Yoghurt A: To a 400 g portion of the above-mentioned culture were added 150 mg of refined fish oil and 8 g of the dried extract of Example 6. Thereto were added 250 g of Syrup A and the resulting mixture was homogenized. After completely filling the resulting homogenized liquid yoghurt A into a glass container it was kept at 10° C. for 14 days.

Syrup B: 50 g of High Fructose Corn Syrup (HFCS-55, containing 23% of water and 77% of carbohydrates, consisting of 55% fructose, 41% glucose, 2% maltose and 2% higher carbohydrates) and 45 g of isomaltulose were dissolved in 155 g sterilized drinking water.

Yoghurt B: To a 400 g portion of the above-mentioned culture were added 125 mg of docosahexaenoic acid (DHA, all-cis-docosa-4,7,10,13,16,19-hexaenoic acid) and 7 g of the dried extract of Example 6. Thereto were added 250 g of Syrup B and the resulting mixture was homogenized. After completely filling the resulting homogenized liquid yoghurt B into a glass container it was kept at 10° C. for 14 days.

Syrup C: 40 g of isomalt and 50 g of maltose were dissolved in 160 g sterilized drinking water.

Yoghurt C: To a 400 g portion of the above-mentioned culture were added 100 mg of docosahexaenoic acid (DHA, all-cis-docosa-4,7,10,13,16,19-hexaenoic acid), 30 mg of eicosatetraenoic acid (ETA, all-cis-8,11,14,17-eicosatetraenoic acid) and 8.5 g of the dried extract of Example 7. Thereto were added 250 g of Syrup C and the resulting mixture was homogenized. After completely filling the resulting homogenized liquid yoghurt C into a glass container it was kept at 10° C. for 14 days.

Application Example F11

Yoghurt with Refined Fish Oil

Water was added to 88 g of skimmed milk powder to make a total of 350 g, said mixture heated at 135° C. for 3 seconds, sterilized, cooled to 37° C., and then inoculated with 0.5% of a starter of *Lactobacillus acidophilus* and 0.75% of a starter of *Bifidobacterium bifidum* and cultured at 37° C. until the pH-value of the culture reached 4.5.

A syrup was produced by adding water to 90 g of isomalt, 60 g of maltose, refined fish oil (200 mg in terms of DHA), and 9.9 g of the dried extract of Example 6 to make a total of 650 g, the resulting syrup heated at 110° C. for 3 seconds, sterilized, and then cooled to a temperature of 8° C.

350 g of the above-mentioned culture and 650 g of the above-mentioned syrup were mixed, and a container made of an aluminium foil-laminated paper was completely filled with the resulting liquid yoghurt, hermetically sealed, and stored at 7° C. for 18 days.

Application Example F12

Yoghurt

Water was added to 120 g of powdered whole milk, 170 g of High Fructose Corn Syrup (HFCS-42; containing 24% of water and 76% of carbohydrates (consisting of 42% fructose, 50% glucose, and 8% other carbohydrates)), 80 g of High Maltose Corn Syrup, and 11.5 g of the dried extract of Example 7 to make a total of 1 kg, the resulting mixture was subjected to homogenization and heat sterilization, then inoculated with 1% of a starter of *Bifidobacterium bifidum* and 0.5% of a starter of *Streptococcus thermophilus*, and cultured at 37° C. until the pH-value of the mixture reached 4.4. Then, the resulting yoghurt was transferred into a glass container, and stored at 8° C. for 9 days.

Application Example F13

Strawberry Fruit Preparation

| Ingredient | A in wt. % | B in wt. % | C in wt. % |
|---|---|---|---|
| Strawberries (individually quick frozen) | 15.00 | 8.00 | 3.00 |
| Strawberry puree (flash pasteurized) | 25.00 | 24.00 | 37.00 |
| Banana puree | — | 14.00 | — |
| Vanilla flavor B | — | — | 0.25 |
| Sucrose | 10.50 | 13.50 | 9.90 |
| Polydextrose | 13.00 | 3.50 | 12.50 |
| Acacia gum | 11.00 | 13.00 | 13.00 |
| Wheat fiber (cellulose fiber) | 1.25 | 3.00 | 0.50 |
| High Fructose Corn Syrup (HFCS-55) | 2.70 | — | 3.90 |
| Citric acid | 0.25 | 0.10 | 0.20 |
| Red colorant | 0.01 | — | 0.01 |
| Dried extract of Example 6 | 1.75 | 3.10 | — |
| Dried extract of Example 2 | — | — | 4.20 |
| Water | Ad 100 | Ad 100 | Ad 100 |

Manufacturing process: heat the strawberries and the fruit puree(s) at 85° C., then add thereto the sugar(s), polydextrose, acacia gum and wheat fibre as indicated above. During cooling of the resulting mixture, add citric acid, the dried extract of Example 6 or Example 2, and optionally vanilla flavor as indicated above.

Each three parts by weight of Plain Bio yoghurt (as described in Application Example F9) were mixed separately with each one part by weight of the above-mentioned strawberry fruit preparations A, B and C. The three different strawberry yoghurts were sufficiently stable during storage at 8° C. for 23 days.

Separately, 5 parts by weight of the yoghurt of Application Example F12 after storage at 8° C. for 9 days were mixed with two parts by weight of the above-mentioned strawberry fruit preparation A, stored for a few hours at 5° C., and then consumed.

Application Example F14

Calcium Enriched Yoghurt Drinks

Water was added to 176 g of skimmed milk powder to make a total of 700 g, said mixture pasteurized at 100° C. for 15 minutes, cooled to 37° C., and then inoculated with *Streptococcus thermophilus* and *Lactobacillus bulgaricus* cultured at 37° C. until the pH-value of the culture reached 4.3.

A separate solution C1 was prepared by dissolving 4.5 g of calcium gluconate in 145.5 g water, pasteurized at 100° C. for 15 minutes and then cooled to a temperature of 7° C.

A separate solution C2 was prepared by dissolving 5.5 g of calcium lactate pentahydrate in 144.5 g water, pasteurized at 100° C. for 15 minutes and then cooled to a temperature of 7° C.

A syrup S1 was produced by adding water to a mixture of 8.2 g of sucrose, 10 g of orange juice concentrate, 3.5 g of HM (high methoxyl) pectin ((degree of esterification 70%) and 7.2 g of the dried extract of Example 6 to make a total of 500 g, the resulting syrup pasteurized at 100° C. for 10 minutes, sterilized, and then cooled to a temperature of 7° C.

A syrup S2 was produced by adding water to a mixture of 14 g of High Fructose Corn Syrup (HFCS-55), 7 g of condensed strawberry juice, 4 g of condensed raspberry juice, 3.25 g of blockwise-type HM (high methoxyl) pectin (degree of esterification 80%) and 7.9 g of the dried extract of Example 7 to make a total of 500 g, the resulting syrup pasteurized at 100° C. for 10 minutes, sterilized, and then cooled to a temperature of 7° C.

Then, 350 g of the above-mentioned culture, 500 g of the above-mentioned syrup S1 and 150 g of the above-mentioned calcium gluconate solution C1 were mixed and homogenized at a pressure of 150 bar to obtain a calcium-enriched yoghurt drink.

Finally, 350 g of the above-mentioned culture, 500 g of the above-mentioned syrup S2 and 150 g of the above-mentioned calcium lactate solution C2 were mixed and homogenized at a pressure of 150 bar to obtain another calcium-enriched yoghurt drink.

Application Example F15

Dietary Supplements

| Ingredient | A in wt. % | B in wt. % | C in wt. % | D in wt. % |
|---|---|---|---|---|
| Soy protein concentrate (72% proteins) | Ad 100 | Ad 100 | — | — |
| Soy protein isolate (88% proteins) | — | — | Ad 100 | Ad 100 |
| Oat bran | 11.50 | 14.50 | 3.00 | — |
| Oat beta-glucan | — | — | 7.50 | 8.00 |
| Barley bran | 9.00 | 9.50 | — | — |
| Soy fiber | 10.00 | 8.00 | 12.00 | 11.00 |
| Rice bran | 7.00 | 7.00 | — | — |
| Beet fiber | 7.00 | 7.00 | — | 1.00 |
| Psyllium fiber (40 mesh) | 8.00 | 4.00 | 10.00 | 11.00 |
| Flaxseed | — | — | 10.00 | 8.00 |
| Ingestible dextrin | — | — | 10.00 | — |
| Sesame flour | 2.00 | — | 5.00 | 2.00 |
| Pectin | — | — | 2.00 | 1.50 |
| Carrageenan | 1.00 | 1.00 | 2.00 | 2.00 |
| Guar Gum | 4.00 | 3.00 | 3.00 | 3.50 |
| Lecithin | 1.20 | — | — | — |
| Oligofructose | 0.50 | — | 0.30 | 0.30 |
| Fructose | — | 0.50 | 0.60 | 0.60 |
| Citric acid, anhydrous | 0.65 | — | 1.00 | 1.00 |
| FD&C yellow #6 (colorant) | 0.20 | — | 0.25 | 0.25 |
| D-Limonene and citrus extract (1:1) | — | 0.10 | 0.10 | — |
| Vanilla flavor A | 0.15 | — | 0.25 | 0.30 |
| Dried extract of Example 6 | 7.00 | — | — | — |
| Dried extract of Example 2 | — | 12.00 | — | — |
| Product D from Application Example F1 | — | — | 5.00 | — |
| Product A from Application Example F1 | — | — | — | 17.50 |

Application Example F16

Liquid Yoghurt and Capsules Filled Therewith

Skimmed milk and whole milk were mixed in proportions to give milk with 1.1% fat, then 5 wt. % of sucrose were added thereto, and heated to 82° C. for 30 minutes. After cooling to 45° C., an appropriate amount of commercial yoghurt culture was added, and the mixture incubated at 45° C. for 5 hours (the pH-value reached 4.4). The resulting firm yoghurt curd was then broken by stirring, and split in two portions (portion A and portion B).

Application Example F16A

Preparation of LiqYog A: To stirred portion A were added 0.4 wt. % (based on the mass of firm yoghurt) of high methoxyl *citrus* pectin as 5 wt. % solution in water and the mixture cooled with stirring to 5° C. This product was then passed through a sterilized homogenizer at 40 bar to give a liquid yoghurt having a dynamic viscosity of 380 mPas at 10° C. Thereto were first added with stirring 6 wt. % of the dried extract of Example 6, and then 9.0 wt. % of a pasteurized peach pulp, in both cases based on the total weight of the liquid yoghurt. The resulting mixture was homogenized giving LiqYog A which was stored at 10° C. before further processing.

The encapsulation of LiqYog A was carried out similar to the method described in U.S. Pat. No. 6,627,236 B1 by dripping drops thereof into an immersion bath. LiqYog A was cooled to 5° C. and drops of 7 mm in diameter are formed using a rigid tube placed 4 cm above the immersion bath, said bath being at a temperature of 25° C. The immersion bath consisted of 0.6 wt. % highly gelling sodium alginate (molecular weight 90000 daltons), 0.2 wt. % of weakly gelling sodium alginate M (molecular weight 18000 daltons), 1.45 wt. % of weakly gelling pectin (46% degree of esterification, 9% degree of amidation), 5% of glycerol, 5% of sucrose and 87.75% of deionized water. Once formed, and after an immersion time of 10 minutes, the capsules are recovered and rinsed three times with deionized water. The amount of LiqYog A in the thus obtained capsules was in the range of 58-60 wt. %.

Application Example F16B

Preparation of LiqYog B: To stirred portion B were added 0.6 wt. % (based on the mass of firm yoghurt) of high methoxyl apple pectin as 5 wt. % solution in water and the mixture cooled with stirring to 5° C. This product was then passed through a sterilized homogenizer at 15 bar to give a liquid yoghurt having a dynamic viscosity of 600 mPas at 10° C. Thereto were first added with stirring 1.4 wt. % of a mixture consisting of euscaphic acid and tormentic acid (7:2) (w/w), and then 7.3 wt. % of a pasteurized strawberry-blueberry puree, in both cases based on the total weight of the liquid yoghurt. The resulting mixture was homogenized giving LiqYog B which was stored at 10° C. before further processing.

LiqYog B (5° C.) was mixed with 0.025 wt. % of aspartame, and 0.025 wt. % acesulfame K, and the resulting mixture used as core liquid in an coextrusion encapsulation process similar to the method described in U.S. Pat. No. 6,627,236 B1. The shell composition (biopolymer solution) used consisted of 0.8 wt. % highly gelling sodium alginate (molecular weight 90000 daltons), 2.0 wt. % of LM (low methoxyl) pectin (degree of esterification 10%), 0.5 wt. % of carob gum (E410), 5% of sucrose, 0.2 wt. % brilliant blue (E-number E133), and 91.5% of deionized water. A concentric two-component nozzle was used to coextrude the above-mentioned core liquid (via the inner tube of the coextruder, diameter 3.5 mm) and the above-mentioned shell composition (via the outer tube of the coextruder, diameter 5.5 mm), said outer tube protruding 5 mm relative to the inner tube. The core liquid drops forming at the outlet of the inner tube of the coextruder, under the effect of gravity, are instantaneously coated with the shell material solution coming from the outer tube. The drops thus preformed fall, by a height of 8 cm into a gelling bath (20° C.) consisting of a 2.1 wt. % calcium chloride solution in deionized water. After 2 minutes of immersion in said gelling bath calcium ions have sufficiently diffused into the shell of the spherical beads obtained and gelation and hardening of the shell is completed. The spherical beads are then transferred from the gelling bath into a rinsing bath, and are rinsed in 3 successive baths of deionized water, thereby also preventing reaggregation of the spherical beads. After the final rinsing, the spherical beads are drained and packaged. The amount of LiqYog B in the thus obtained spherical beads (diameter about 8 mm) is in the range of 35 to 40 wt. %.

25 of the above-mentioned 8 mm blue beads containing LiqYog B and the high potency sweeteners were placed into a 400 ml yoghurt drink container which was then filled with yellow-colored banana-vanilla-flavored liquid yoghurt having a dynamic viscosity of 145 mPas at 10° C.

Application Example F17

Supplement and Drink Compositions

| Ingredient | A in wt. % | B in wt. % | C in wt. % | D in wt. % |
|---|---|---|---|---|
| Isolated soy protein | Ad 100 | — | Ad 100 | — |
| Milk protein isolate (spray-dried, soluble casein and whey proteins isolated from fresh skimmed milk) | 21.00 | — | 20.00 | — |
| Skimmed milk powder | — | 15.00 | — | 11.50 |
| Fructose | 14.56 | — | 7.56 | 5.00 |
| Granular sucrose | — | Ad 100 | 7.00 | Ad 100 |
| Chicory inulin | 8.79 | — | 8.00 | — |
| Cocoa powder (14% fat) | — | 16.00 | — | 16.00 |
| Oat beta-glucan | 2.50 | — | — | 2.00 |
| Guar Gum | 2.30 | — | 2.56 | 0.90 |
| Potassium chloride | 3.11 | — | 3.00 | 0.1 |
| Sodium chloride | 0.30 | 0.4 | 0.30 | 0.4 |
| Lecithin | — | 1.00 | — | 1.10 |
| Spray-dried strawberry flavor | 1.20 | — | 1.20 | — |
| Spray-dried Vanilla Flavor B | 0.53 | — | 0.53 | — |
| Vanilla Flavor A | — | 0.04 | — | 0.10 |
| Chocolate flavor | — | 0.12 | — | 0.10 |
| Microcrystalline cellulose | 1.28 | — | 1.22 | — |
| Vitamin-Mix-1* | 0.12 | — | 0.20 | — |
| Vitamin-Mix-2** | — | 0.22 | — | 0.26 |
| Mineral-Mix*** | 0.24 | — | 0.14 | — |
| Methionine | 0.33 | — | 0.30 | — |
| Magnesium oxide | 0.33 | — | 0.30 | — |
| FD&C Red #40 (colorant) | 0.02 | 0.05 | — | 0.05 |
| Silicon dioxide | 0.22 | — | 0.25 | — |
| Acesulfam K | 0.25 | — | — | 0.10 |
| Citric acid, anhydrous | 0.25 | — | 0.10 | — |
| Butylated hydroxytoluene (BHT) | — | 0.0003 | 0.0002 | 0.0003 |
| Calcium phosphate | — | 0.05 | 0.04 | 0.05 |
| Calcium panthothenate | — | 0.003 | — | 0.003 |
| Ferrous fumarate | — | 0.06 | 0.04 | 0.06 |
| Dried extract of Example 6 | 4.00 | — | 4.00 | 6.00 |
| Dried extract of Example 7 | — | 6.00 | — | — |
| Product D from Application Example F1 | — | — | 3.00 | — |

Vitamin-Mix-1* consisted of 13 vitamins, including retinol (vitamin A1), vitamin A plamitate, thiamine mononitrate (vitamin B1), riboflavin (vitamin B1), niacinamide (vitamin B3), vitamin B6, vitamin B12, vitamin C (ascorbic acid), vitamin D3 (cholecalciferol), vitamin E acetate and vitamin K (phytonadione).
Vitamin-Mix-2** consisted of 0.0007% riboflavin, 0.21% ascorbic acid, 0.023% niacinamide, 0.001% of thiamine mononitrate, 0.001% retinol (vitamin A1), 0.001% beta-carotene and 0.001% vitamin D, said percentages relating to the total weight of the final composition.
Mineral-Mix*** consisted of 11 minerals, including dicalcium phosphate, ferric orthophosphate, zinc oxide, copper sulfate, potassium iodide, manganese sulfate, sodium molybdate, and sodium selenite.

25 g of composition B were dissolved in 240 g of semi-skimmed milk to give a chocolate and vanilla flavored beverage.

Application Example F18

Soy Milk Based Beverage 92 parts by weight of soy milk and 5.5 parts by weight of the dried extract of Example 6 are mixed with 1.3 parts by weight of pectin and are then brought a pH value of 3.9 by adding about 1.2 parts by weight of lactic acid. Subsequently, the mixture is heated to 90° C. for 1 minute, it is homogenized at 250/50 bar and cooled down to 20° C. In the subsequent spray drying process a powder is obtained with a protein content of about 38 wt. %. Subsequently, 25 g of said powder are dissolved in one liter of fruit juice with a fruit content of 30%, the pH value is set to 3.9 with sodium citrate, thereby obtaining a protein-enriched beverage. After heating to 90° C. for 1 minute homogenization at 250/50 bar is carried out. Subsequently, the beverage is cooled to 7° C.

The stability of a drink obtained in this manner does not show ring formation for several weeks. The stability in view of the sedimentation is also very good.

Application Example F19

Chocolate Bars

| Ingredient | A in wt. % | B in wt. % | C in wt. % |
|---|---|---|---|
| Corn syrup (DE 63) | Ad 100 | Ad 100 | Ad 100 |
| Cane sugar | 21.00 | 21.00 | 21.00 |
| Sweetened condensed skimmed milk | 15.00 | 15.00 | 15.00 |
| Dark chocolate liquor* | 20.00 | — | 10.00 |
| Milk chocolate liquor | — | 14.00 | 10.00 |
| Cocoa powder (12% fat; total procyanidin content: 65 mg/g cocoa powder) | 8.00 | 8.00 | 8.00 |
| Canola stanol esters** | 2.00 | — | 3.50 |
| Phytosterol mixture*** | — | 3.00 | — |
| Soy lecithin | 0.125 | 0.125 | 0.125 |
| Water | — | 8.00 | 3.00 |
| Sodium chloride | 0.08 | 0.05 | 0.05 |
| Vanilla and cream flavor | 0.75 | — | 0.40 |
| Almond, cinnamon and vanilla flavor | — | 0.75 | 0.40 |
| Dried extract of Example 1 | 3.55 | — | — |
| Dried extract of Example 6 | — | 1.90 | — |
| Dried extract of Example 8 | — | — | 2.50 |

Dark chocolate liquor* said liquor was made by cracking infra-red heated beans, separating and collecting the cocoa nibs, crushing at 50° C. and finally milling the nibs for one hour into a coarse dark chocolate liquor. The total cocoa procyanidin content was 49 mg/g of dark chocolate liquor.
Canola stanol esters** the canola stanol ester mixture was prepared by interesterification of a mixture consisting of stigmastanol (beta-sitostanol) (70%), and campestanol (30%) according to the process described is U.S. Pat. No. 5,502,045.
Phytosterol mixture*** consisted of beta-sitosterol (44%), campesterol (27%), and stigmasterol (10%), brassicasterol (8 wt.%), stigmastanol (6%), ergostanol (3%), and citrostadienol (2%).

Dark chocolate liquor*: said liquor was made by cracking infra-red heated beans, separating and collecting the cocoa nibs, crushing at 50° C. and finally milling the nibs for one hour into a coarse dark chocolate liquor. The total cocoa procyanidin content was 49 mg/g of dark chocolate liquor.

Canola stanol esters**: the canola stanol ester mixture was prepared by interesterification of a mixture consisting of stigmastanol (beta-sitostanol) (70%), and campestanol (30%) according to the process described in U.S. Pat. No. 5,502,045.

Phytosterol mixture***: consisted of beta-sitosterol (44%), campesterol (27%), and stigmasterol (10%), brassicasterol (8 wt. %), stigmastanol (6%), ergostanol (3%), and citrostadienol (2%).

The bars were prepared from the ingredients indicated above by pre-mixing stanol esters or phytosterols, the dried extract of Example 6 or Example 8, cocoa powder, soy lecithin, and dark chocolate liquor or milk chocolate liquor in a Z-blade mixer. The thus obtained pre-mixes each were incorporated separately into the respective syrup (heated to 66° C.) containing the remaining ingredients indicated in the table above. The resulting mixtures were each slowly cooled, rolled, and enwrapped. The moisture content of the final bars was about 8.5%.

Application Example F20

Granola Bars

| Ingredient | A in wt. % | B in wt. % | C in wt. % | D in wt. % |
|---|---|---|---|---|
| Part A | | | | |
| Corn syrup (DE 55) | Ad 100 | Ad 100 | Ad 100 | Ad 100 |
| Corn syrup (DE 63) | 8.00 | 7.50 | 8.50 | 9.00 |
| Fructose | 0.60 | 1.00 | 1.50 | 2.00 |
| Brown sugar | 0.30 | 0.50 | 0.70 | — |
| Sodium chloride | 0.35 | 0.40 | 0.25 | 0.25 |
| Vitamin-Mix-2** | 0.25 | 0.50 | 0.75 | 0.80 |
| Vanilla and cream flavor | 0.25 | — | 0.10 | 0.30 |
| Almond, cinnamon and vanilla flavor | — | 0.30 | 0.15 | — |
| Water | 8.50 | 9.00 | 8.00 | 8.00 |
| Part B | | | | |
| Dark chocolate liquor* | 1.25 | — | 0.60 | 0.45 |
| Milk chocolate liquor | — | 1.40 | 1.00 | 0.95 |
| Cocoa powder* | 7.50 | 7.00 | 8.00 | 8.00 |
| Canola stanol esters* | 3.65 | — | — | — |
| Phytosterol mixture* | — | 1.90 | 2.15 | — |
| Soybean oil*** | — | — | 0.85 | 3.90 |
| Soy lecithin | 0.20 | 0.20 | 0.20 | 0.22 |
| Dried extract of Example 6 | 4.40 | 2.80 | — | — |
| Dried extract of Example 1 | — | — | 4.50 | — |
| Dried extract of Example 8 | — | — | — | 2.50 |
| Part C | | | | |
| Soy crisps | 10.00 | 6.00 | 8.00 | 5.00 |
| Rice crisps | 8.00 | 8.00 | 4.00 | 6.00 |
| Oats | 5.50 | 11.00 | 8.00 | 9.00 |
| Chopped almonds and hazelnuts (1:1) | — | 4.00 | 3.50 | 3.00 |
| Coconut flakes and raisins (1:4) | 3.50 | 3.00 | — | 2.00 |
| Dried apple pieces | 3.00 | — | — | 2.50 |
| Dried blueberries and cranberries (1:1) | 2.00 | — | 3.50 | 3.00 |
| Dried and crushed cherries | — | 3.00 | 2.00 | — |
| Part D | | | | |
| Milk chocolate for enrobing | 17.00 | — | — | 17.50 |
| Dark chocolate for enrobing | — | — | 12.00 | — |
| White chocolate for enrobing | — | 19.00 | 6.00 | — |

*see Application Example F19
Vitamin-Mix-2** see Application Example F17
Soybean oil*** containing 360 mg of plant sterols per 100 g of soybean oil; the main soy sterols were beta-sitosterol (54%), campesterol (22%), and stigmasterol (19%).

A mixture containing all ingredients of part A was prepared by blending the ingredients at about 55° C. for 15 minutes in a high speed mixer to give an aqueous syrup. A second mixture containing all ingredients of part B was prepared by blending said ingredients for 15 minutes in a high speed mixer to create a pretreated solids mixture. The aqueous syrup and the pretreated solids mixture were mixed to yield a binder mixture which was then blended with the dry ingredients of part C. Each resulting mixture was deposited separately as a slab, compressed, slit into bars, and then cooled. Each bar was then covered with molten chocolate (part D). Finally, after cooling, the obtained chocolate covered granola bars were enwrapped.

Application Example F21

Elliptical Hard Gelatin Capsules

| Ingredient | A in mg | B in mg | C in mg | D in mg | E in mg | F in mg |
|---|---|---|---|---|---|---|
| Filling of the elliptical hard gelatin capsule | | | | | | |
| Microcrystalline cellulose | 70 | 70 | 50 | 30 | — | — |
| Anhydrous colloidal silica | 5 | 1 | 5 | 1 | — | 1 |
| Magnesium stearate | — | 3 | — | 3 | 5 | 3 |
| Dicalcium phosphate dihydrate | 30 | 60 | 50 | 50 | — | 50 |
| Phytosterol mixture* | — | 200 | — | — | 150 | — |
| Zeaxanthin palmitate | 40 | — | 25 | — | — | — |
| Ascorbic acid | 12 | — | — | 20 | — | 15 |
| Peppermint flavor** | 15 | — | 26 | 12 | 30 | — |
| Fresh spicy flavor*** | — | 27 | — | 12 | — | 20 |
| Dried extract of Example 2 | 600 | — | — | — | — | — |
| Dried extract of Example 6 | — | 220 | 450 | — | — | — |
| Dried extract of Example 7 | — | — | — | 500 | — | — |
| Dried extract of Example 8 | — | — | — | — | 380 | — |
| Product B from Application Example F1 | — | — | — | — | — | 450 |
| Coating of the filled elliptical hard gelatin capsule | | | | | | |
| Peppermint flavor** | 8 | — | 10 | 3 | 8 | — |
| Shellac | 5 | 5 | 5 | — | 5 | — |
| Talc | 60 | — | 50 | — | 40 | 60 |
| Sucrose | 250 | 300 | — | — | 220 | — |
| Isomalt and xylitol (1:1) | — | — | 240 | 300 | — | 250 |
| Polyvidone (Polyvinylpyrrolidone) | 6 | — | — | — | 8 | — |
| Titanium dioxide (E-number E171) | 0.3 | 1 | 5 | — | 0.3 | — |
| FD&C Red #40 (colorant) | — | 5 | — | 3 | — | 7 |
| Brillliant blue (E-number E133) | 5 | — | — | 4 | 7 | — |

*see Application Example F19
Peppermint flavor** consisted of 0.05 wt. % Isobutyraldehyde, 0.05 wt. % 3-octanol, 0.05 wt. % dimethylsulfide, 0.1 wt. % trans-2-hexenal, 0.1 wt. % cis-hexenol, 0.1 wt. % 4-terpineol, 0.1 wt. % isopulegol, 0.2 wt. % piperitone, 0.3 wt. % linaool, 0.3 wt. % 8-ocimenyl acetate, 0.7 wt. % isoamylalcohol, 0.7 wt. % isovaleraldehyde, 2.5 wt. % alpha-pinene, 2.0 wt. % beta-pinene, 3.8 wt. % neo-menthol, 4.0 wt. % eucalyptol, 5.0 wt. % d-isomenthone, 7.0 wt. % I-menthyl acetate, 21.0 wt. % I-menthone, 3.4 wt. % I-menthyl-l-lactate, 0.8 wt.% N-2,3-trimethyl-2-propan-2-ylbutanamide (WS-23), and I-menthol (ad 100%).
Fresh spicy flavor*** consisted of 5.0 wt. % eugenol, 7.0 wt. % cinnamaldehyde, 8.0 wt. % I-carvone, 12.0 wt. % anethole, 18 wt. % *Mentha piperita* oil, 18 wt. % *Mentha arvensis* oil, 1.2 wt. % N-ethyl-p-menthane-3-carboxamide (WS-3), and l-menthol (ad 100%).

Application Example F22

Powder Containing Whey Protein Isolate and Lycopene 20 parts by weight of whey protein isolate and 11 parts by weight of soybean extract (comprising 33% of isoflavones) are dissolved in 550 parts by weight of demineralized water and the mixture is stirred for six hours at 25° C. Separately, 1.0 part by weight of natural tomato lycopene oleoresin (comprising 8% of lycopene), are mixed with 580 parts by weight of acetone with stirring. Both solutions are then mixed and stirred for one hour at 30° C. The resulting mixture is moderately heated and the acetone and the major part of water removed under reduced pressure. Finally, about 150 parts by weight of an aqueous mixture of whey protein isolate, soybean extract and tomato lycopene oleoresin are obtained. Separately, 12 parts by weight of modified starch, 10 parts by weight of the dried extract of Example 7, 15 parts of maltodextrin (DE 12), and 1 part gum Arabic are combined with 120 parts of a mixture of ethanol and water. The resulting mixture is combined with the 150 parts by weight of the above-mentioned aqueous mixture and subsequently spray-dried to give a powder.

Application Example F23

Pressed Tablets

| Ingredient | A in wt. % | B in wt. % | C in wt. % | D in wt. % | E in wt. % |
|---|---|---|---|---|---|
| Glucose | — | Ad 100 | Ad 100 | — | 22.00 |
| Ludiflash ®* | Ad 100 | — | 25.00 | Ad 100 | Ad 100 |
| Magnesium stearate | — | 0.90 | 0.80 | 0.60 | 0.80 |
| Sodium stearyl fumarate | 0.90 | — | — | 0.60 | 0.20 |
| Citric acid | 0.20 | 0.10 | — | 0.20 | — |
| Ascorbic acid | — | 0.10 | 0.50 | 2.00 | 5.00 |
| Phytosterol mixture** | — | 0.80 | — | 1.00 | — |
| Honey flavor | 0.70 | — | 0.30 | — | 0.60 |
| Orange flavor | — | 0.85 | 0.40 | 0.80 | 0.50 |
| Dried extract of Example 6 | 2.55 | — | — | 1.50 | — |
| Dried extract of Example 7 | — | 1.80 | — | — | — |
| Product B from Application Example F1 | — | — | 13.50 | 6.00 | — |
| Powder from Application Example F22 | — | — | — | — | 30.00 |

Ludiflash ®* (commercially available from BASF SE): fast dispersable excipient based on mannitol, polyvinyl acetate and crospovidone (crospovidone is a highly cross-linked homopolymer of N-vinyl-2-pyrrolidone; E-number E1202)
Phytosterol mixture**see Application Example F19

The 10 mm round flat bevelled edge pressed tablets were produced at a compression force of 200 MPa.

Application Example F24

Mononuclearly Filled Spherical Seamless Gelatin Capsules

Coating-free core-shell seamless capsules were prepared as described in US 2008/0317824 A1 or US 2005/0123601 A1, having the following composition:

| Core composition | A in wt. % | B in wt. % | C in wt. % |
| --- | --- | --- | --- |
| Peppermint oil (Mentha arvensis) | 29.8 | 25.8 | 23.8 |
| Fractionated coconut oil | Ad 100 | — | Ad 100 |
| Soybean oil* | — | Ad 100 | 28.00 |
| Euscaphic acid and tormentic acid (7:2) | 1.25 | — | — |
| Dried extract of Example 6 | — | 4.50 | — |
| Dried extract of Example 8 | — | — | 6.00 |
| Neotame | 0.06 | 0.05 | — |
| Sucralose | 1.1 | 1.0 | 1.14 |
| Limonene | 2.0 | 2.5 | 2.5 |
| L-menthyl acetate | 3.50 | 1.00 | 4.00 |
| L-Menthyl-l-lactate | 2.3 | 1.3 | — |
| WS-3 | 1.4 | 2.4 | 3.1 |
| Diethyl tartrate | 1.0 | — | 2.0 |
| Triacetin | 1.0 | 2.2 | — |
| Ethanol | 0.5 | 0.5 | 0.6 |
| Vitamin E-acetate | 0.3 | 0.3 | 0.3 |

Soybean oil* see Application Example F20

| Shell composition | A in wt. % | B in wt. % | C in wt. % |
| --- | --- | --- | --- |
| Water | 2.9 | 3.0 | 2.8 |
| Glycerol | 10.3 | 20.5 | 5.0 |
| Sorbitol | 10.0 | — | 15.0 |
| Fish gelatin 0 Bloom | — | — | 17.5 |
| Pig gelatin 260 Bloom | Ad 100 | — | Ad 100 |
| Chicken gelatin 250 Bloom | — | Ad 100 | — |
| Sucralose | 0.6 | — | 0.4 |
| Acesulfam K | — | 0.4 | — |
| Aspartame | — | 0.35 | 0.3 |
| Allura Red | — | 0.05 | 0.1 |
| FD&C Blue #5 | 0.1 | 0.05 | — |

A coating-free seamless capsule A had the following properties: 5 mm diameter; 11% shell, 89% core liquid. A coating-free seamless capsule B had the following properties: 3.5 mm diameter; 18% shell, 82% core liquid. A coating-free seamless capsule C had the following properties: 8 mm diameter; 6% shell, 94% core liquid.

Coating of the Coating-Free Gelatin Spherical Capsules A:

All coating steps were carried out in a panning machine. To improve the adhesion of the sugar alcohol coating to be applied in the next step, two layers of gum arabic (50% in water) were applied to the coating-free capsules. These capsules were then placed on trays and dried in a drying chamber at 35 to 45° C.

In a first coating step, a 70% aqueous solution of isomalt was used as coating mixture and 10 layers were applied to the dried gum arabic encased capsules. In the next coating step, these capsules were then coated with 12 layers using the following coating mixture: 68% isomalt, 5% titanium dioxide and 27% of water. The capsules now have a bright white appearance. In a further step the obtained capsules were then coated with 8 layers using the following coating mixture: 65% isomalt and 35% water. The capsules now have a smoother surface. In a further step the obtained capsules were then coated with about 10 layers using the following coating mixture: 65% isomalt, 5% of an aqueous solution of a mixture of FD&C Blue #1 and D&C Red #33, and 30% water. The capsules now have a smoother surface and a purple color. The resulting capsules are then placed on trays and dried for 12 hours in a drying chamber at 32° C. Finally, a shiny layer of carnauba wax was added to the coated capsules.

The coating of the coating-free gelatin spherical capsules B was performed as described for the coating-free gelatin spherical capsules A, with the sole difference that isomalt was replaced in all steps with xylitol. The coating of the coating-free gelatin spherical capsules C was performed as described for the coating-free gelatin spherical capsules A, with the sole difference that isomalt was replaced in all steps with dextrose.

Application Example F25

Powder Blends and Effervescent Tablets

| Ingredient | A in wt. % | B in wt. % | C in wt. % | D in wt. % | E in wt. % |
| --- | --- | --- | --- | --- | --- |
| Creatine monohydrate | Ad 100 | Ad 100 | Ad 100 | Ad 100 | Ad 100 |
| Glucose | 1.00 | 6.50 | — | 4.00 | — |
| Acesulfame K | 0.50 | — | 0.50 | 0.15 | 0.50 |
| Aspartame | 0.50 | — | 0.50 | 0.15 | 0.50 |
| Gamma-Cyclodextrin | — | 3.00 | — | 3.50 | 5.00 |
| Sodium carbonate | 5.5 | 5.0 | 6.0 | 5.0 | 5.0 |
| Sodium bicarbonate | 12.00 | 15.00 | 13.00 | 15.00 | 14.00 |
| Magnesium hydroxide | 4.00 | 4.00 | 4.00 | 4.00 | 4.00 |
| Alpha-lipoic acid | 0.20 | — | 0.25 | — | 0.20 |
| Alpha-lipoic acid (ALA)/alpha-cyclodextrin complex (20% of ALA) | — | 1.25 | 1.00 | 1.00 | — |
| Citric acid | 18.00 | 17.50 | 18.00 | 16.50 | 18.00 |
| Ascorbic acid | — | 2.50 | 0.50 | — | 0.50 |
| Malic acid | — | — | 0.50 | 2.50 | 0.50 |
| Lemon-grapefruit flavor, spray-dried | 3.70 | — | 2.60 | — | 4.75 |
| Apple-rose hip flavor, spray-dried | — | 4.90 | 2.40 | 4.75 | — |
| Dried extract of Example 6 | 6.55 | — | — | — | — |
| Dried extract of Example 8 | — | 7.60 | — | — | — |
| Product C from Application Example F1 | — | — | 19.50 | — | — |
| Euscaphic acid, tormentic acid and myrianthic acid (13:5:1) (w/w/w) | — | — | — | 3.25 | — |
| Powder from Application Example F22 | — | — | — | — | 35.00 |

Application Example F26

Probiotic Fermented Milk Product

| Ingredient | A | B | C | D | E |
| --- | --- | --- | --- | --- | --- |
| | in parts by weight | | | | |
| Yakult ®* | 65 | — | 65 | — | 65 |
| Yakult ® light** | — | 65 | — | 65 | — |
| Phytosterol mixture*** | — | — | 0.60 | 0.40 | — |
| Oat beta-glucan | 0.50 | — | — | — | 1.00 |
| Glucomannan | — | — | 0.50 | 0.50 | — |
| Aqueous extract of Psyllium seed husks | — | 1.00 | 1.00 | 1.00 | 1.00 |
| Dried extract of Example 6 | 1.00 | — | 0.90 | — | — |
| Dried extract of Example 7 | — | 1.50 | — | — | — |

-continued

| Ingredient | A | B | C | D | E |
|---|---|---|---|---|---|
| | in parts by weight | | | | |
| Euscaphic acid, tormentic acid and myrianthic acid (14:5:1) (w/w/w) | — | — | — | 0.45 | — |
| Product D from Application Example F1 | — | — | 0.45 | — | 4.30 |

Yakult ®* the Yakult ® product (65 g per serving) was purchased in a local supermarket. The product contained a total of 1.3 wt. % of proteins, <0.1 wt. % of fat, and 17.9 wt. % of carbohydrates (including 15.7% of sucrose, 0.4% of glucose, 1.8% of lactose), 0.0156 wt. % of sodium, skimmed milk powder, flavors, *Lactobacillus casei* Shirota strain (a total of 6.5 billion bacteria, corresponding to 100 million bacteria per gramm Yakult ®), and added water.

Yakult ® light** the Yakult ® light (65 g per serving) was purchased in a local supermarket. The product contained a total of 1.3 wt. % of proteins, <0.1 wt. % of fat, and 13.8 wt. % of carbohydrates (including 8.7% of sucrose, 0.4% of glucose, 1.8% of lactose, and 2.6% dietary fiber (polydextrose, E1200)), 0.0156 wt. % of sodium, sucralose (E-number E955) skimmed milk powder, flavors, *Lactobacillus casei* Shirota strain (a total of 6.5 billion bacteria, corresponding to 100 million bacteria per gramm Yakult ® light), and added water.

Phytosterol mixture*** the mixture consisted of beta-sitosterol (40.1%), campesterol (20.0%), stigmasterol (15.0%) and a total of 25% of brassicasterol, stigmastanol, and campestanol.

Application Example F27

Powder Compositions

| Ingredient | A | B | C | D | E |
|---|---|---|---|---|---|
| | in mg | | | | |
| Sodium hydrogen carbonate | 400 | — | — | 450 | 100 |
| Calcium carbonate | — | 500 | 380 | — | 100 |
| Sorbitol | 100 | 420 | — | — | 150 |
| Mannitol | 250 | — | 380 | 400 | 150 |
| Pregelatinized corn starch | 20 | 20 | — | 25 | — |
| Potato starch | 13 | — | 13 | — | — |
| Talc | 36 | 40 | — | 35 | 15 |
| Magnesium stearate | 11 | 14 | — | 10 | 20 |
| Light liquid paraffin | — | 5 | — | 5 | — |
| Spearmint oil | 10 | — | 20 | — | — |
| Lemon flavor, spray-dried | — | — | 10 | 10 | 10 |
| Menthol-cherry flavor, spray-dried | — | 10 | — | — | 10 |
| Sodium saccharin | 1 | — | 1 | 2 | 2 |
| Dried extract of Example 6 | 150 | — | 125 | — | — |
| Dried extract of Example 2 | — | 290 | — | — | — |
| Euscaphic acid, tormentic acid and myrianthic acid (14:5:1) (w/w/w) | — | — | — | 100 | — |
| Product D from Application Example F1 | — | — | — | — | 493 |
| Total weight in mg: | 996 | 1294 | 929 | 1037 | 1050 |

Powder compositions A and E were each separately pressed into single tablets, and subsequently coated with a peppermint flavored isomalt/xylitol mixture (similar to the method described in Application Example F24).

Powder composition B was packaged in a sachet sealed against light and air.

Powder compositions C and D were each separately fully included into a two-piece hard gelatin capsule.

Application Example F28

Dairy Drink with Phytosterols

| Ingredient | A | B | C | D | E |
|---|---|---|---|---|---|
| | in parts by weight | | | | |
| Danacol* (classic) | 100 | — | 100 | 100 | — |
| Danacol* (with strawberry flavor) | — | 100 | — | — | 100 |
| Aqueous extract of Psyllium seed husks | — | 0.60 | — | 1.00 | — |
| Dried extract of Example 6 | 1.80 | — | — | — | — |
| Dried extract of Example 7 | — | 2.50 | — | — | — |
| Dried extract of Example 8 | — | — | 3.25 | — | — |
| Euscaphic acid, tormentic acid and myrianthic acid (16:5:2) (w/w/w) | — | — | — | 0.75 | — |
| Product D from Application Example F1 | — | — | — | — | 5.00 |

Danacol*: the dairy drink from Danone GmbH (100 g per serving) was purchased in a local supermarket. The product contained a total of 3.3 wt. % of proteins, 1.1 wt. % of fat (including 0.1% saturated fats), and 4.4 wt. % of carbohydrates (including 4.2% of sugars), 0.04 wt. % of sodium, 0.123% of calcium, 0.7 wt. % of dietary fibers, and a total of 1.6 g plant phytosterols.

Application Example F29

Salad Dressings

| Ingredient | A in wt. % | B in wt. % | C in wt. % |
|---|---|---|---|
| Sunflower and olive oil (1:1) | 26.50 | 35.00 | 21.00 |
| Soybean oil* | 11.00 | — | 15.00 |
| White wine vinegar (acid content 9%) | 11.00 | 12.00 | 12.70 |
| Sucrose | 6.00 | 7.00 | 8.00 |
| Egg yolk | 1.70 | 2.00 | 1.80 |
| Sodium chloride | 0.50 | 0.70 | 0.70 |
| Monosodium glutamate | 0.50 | 0.40 | 0.40 |
| Thickener | 0.25 | 0.22 | 0.05 |
| Onion and garlic powder | 0.60 | 0.70 | 0.55 |
| Lemon juice | 0.40 | 0.50 | 0.60 |
| Lemon oil | 0.007 | 0.01 | — |
| Mustard | 1.60 | 1.25 | 1.80 |
| Product D from Application Example F1 | — | — | 1.95 |
| Dried extract of Example 6 | 1.45 | — | — |
| Euscaphic acid, tormentic acid and myrianthic acid (16:5:1) (w/w/w) | — | 0.65 | — |
| Drinking water | Ad 100 | Ad 100 | Ad 100 |

Soybean oil* see Application Example F20

Application Example F30

Pina Colada Mix

| Ingredient | A in wt. % | B in wt. % | C in wt. % |
|---|---|---|---|
| Part A | | | |
| Stabilizer/thickener | 0.15 | 0.10 | 0.10 |
| Sodium benzoate | 0.10 | 0.12 | 0.14 |
| Potassium sorbate | 0.10 | 0.12 | 0.16 |
| Emulsifier | 0.10 | 0.10 | 0.10 |
| Sodium hexametaphosphate | 0.10 | — | — |
| Clouding agent (TiO$_2$) | 0.07 | — | 0.05 |
| Drinking water | Ad 100 | Ad 100 | Ad 100 |
| Part B | | | |
| Cream of coconut | 18.50 | 21.00 | 21.00 |
| Pineapple juice concentrate, 45° Brix | 12.00 | 14.00 | 13.50 |
| High fructose corn syrup (HFCS-42)* | 9.50 | 10.20 | 10.60 |
| Citric acid, anhydrous | 0.32 | 0.38 | 0.35 |
| Coconut flavor | 0.10 | 0.13 | 0.13 |

-continued

| Ingredient | A in wt. % | B in wt. % | C in wt. % |
|---|---|---|---|
| Dried extract of Example 2 | 2.40 | — | — |
| Dried extract of Example 6 | — | 1.80 | — |
| Euscaphic acid, tormentic acid and myrianthic acid (16:5:2) (w/w/w) | — | — | 0.75 |

High fructose corn syrup (HFCS-42)* see Application Example F12

The ingredients of Part A were blended at 35° C. Then, the ingredients of Part B are added with stirring, following homogenization at 60° C. and 3500 psi and filling into bottles.

Application Example F31

Seasonings for Chips

| Ingredient | A in wt. % | B in wt. % | C in wt. % |
|---|---|---|---|
| Maltodextrin | Ad 100 | Ad 100 | Ad 100 |
| Sodium chloride | 20.00 | 13.00 | 18.00 |
| Sodium glutamate | 5.00 | 6.00 | 6.00 |
| Yeast extract | 4.00 | 3.00 | 4.00 |
| White pepper | 0.02 | 0.01 | 0.02 |
| Black pepper | 0.01 | 0.03 | 0.01 |
| Onion powder | 1.50 | 1.70 | 1.50 |
| Garlic powder | 1.00 | 1.10 | 1.00 |
| Cheese powder | 8.00 | — | 10.00 |
| Whey powder | 8.00 | 15.00 | — |
| Paprika powder | 8.00 | 2.00 | 1.00 |
| Tomato powder | 9.00 | 2.00 | — |
| Silicon dioxide | 0.03 | — | 0.05 |
| Sucrose | 7.50 | 12.00 | 9.50 |
| Dextrose | 5.00 | 1.00 | 5.00 |
| Mexican-type flavor (spray-dried) | — | 20.00 | — |
| Cheese and onion-type flavor (spray-dried) | 9.00 | 3.00 | 21.00 |
| Dried extract of Example 2 | 2.15 | — | — |
| Dried extract of Example 6 | — | 1.35 | — |
| Product D from Application Example F1 | — | — | 7.00 |

6 g of spice mixture A were sprinkled onto 94 g of freshly fried potato chips.

7 g of spice mixture B were uniformly applied onto 93 g of freshly deep-fried taco corn chips.

8 g of spice mixture C were uniformly applied onto 92 g of freshly deep-fried corn and whole-grain oat chips.

Application Example F32

Liquid Yoghurts with Health Benefits

Five commercially available flavored standard yoghurt drinks (150 g each, three with strawberry flavor and two with peach flavor) were purchased at the local supermarket. Each of said yoghurt drinks contained 2.8% of proteins, 11.5% of carbohydrates, and 0.9% of fats.

To the first strawberry flavored yoghurt drink were added with stirring 2.5 g of the dried extract of Example 2, 0.35 g of alpha-linolenic acid, and 0.001 g of vitamin E.

To the second strawberry flavored yoghurt drink were added with stirring 4.5 g of the dried extract of Example 2, 0.42 g of alpha-linolenic acid, 0.002 g of vitamin E, and 0.70 g of the phytosterol mixture described in Application example F19.

To the third strawberry flavored yoghurt drink were added with stirring 3.5 g of the dried extract of Example 6, 0.50 g of alpha-linolenic acid, 0.002 g of vitamin E, and 0.85 g of the phytosterol mixture described in Application example F20.

To the first peach flavored yoghurt drink were added with stirring 1.2 g of a mixture consisting of euscaphic acid, tormentic acid and myrianthic acid (16:5:1) (w/w/w), 0.38 g of alpha-linolenic acid, 0.002 g of vitamin E, and 0.95 g of the canola stanol esters described in Application example F19.

To the other peach flavored yoghurt drink were added with stirring 2.75 g of the dried extract of Example 7, 0.40 g of alpha-linolenic acid, 0.001 g of vitamin E, and 1.05 g of the phytosterol mixture described in Application example F20.

Application Example F33

Soft Candies (Chewing Candy)

| Ingredient | A in wt. % | B in wt. % | C in wt. % |
|---|---|---|---|
| Water | 7.00 | 7.50 | 7.00 |
| Sucrose | Ad 100 | Ad 100 | Ad 100 |
| Glucose syrup ("liquid glucose", DE 40) | 36.40 | 36.60 | 36.60 |
| Hydrogenated vegetable oil (fat) (m.p. 32-36° C.) | 6.50 | 6.50 | 6.50 |
| Soy lecithin | 0.30 | 0.30 | 0.30 |
| Gelatin | 0.80 | 0.80 | 0.80 |
| Fondant | 4.80 | 4.80 | 4.80 |
| Orange flavor | — | 0.60 | — |
| Coffee-cream--caramel flavor | — | — | 0.40 |
| Strawberry-vanilla flavor | 0.40 | — | — |
| Colorant | 0.02 | 0.02 | 0.01 |
| Dried extract of Example 6 | 1.25 | — | — |
| Dried extract of Example 8 | — | 4.75 | — |
| Product D from Application Example F1 | — | — | 7.60 |

Manufacturing Procedure:
a) Allow the gelatin to swell with water (1.8 times the amount of gelatine) at 70° C. for 1 hour,
b) Heat the sugar, glucose syrup, the remaining water, fat and lecithin at 123° C.,
c) Slowly mix the gelatin solution a) and the boiled mixture b),
d) Stir in the dried extract of Example 6 or 8, or product D from Application Example F1, respectively, then add the respective flavor and colorant,
e) Control the temperature of the resulting mass to about 70° C. on a cooling bench, then add the fondant and aerate on a drawing machine for approx. 3 minutes,
f) Cut and package the obtained soft candy mass.

Application Example F34

Biscuits (Industrial Quality)

| Ingredient | A in wt. % | B in wt. % | C in wt. % |
|---|---|---|---|
| Wheat flour | Ad 100 | Ad 100 | Ad 100 |
| Potato starch | — | 6.00 | 11.00 |
| Vegetable soft fat | 19.00 | 18.00 | 18.00 |
| Powdered sucrose | 19.00 | 20.00 | 19.00 |
| Sodium chloride | 0.30 | 0.40 | 0.40 |
| Ammonium bicarbonate | 0.40 | 0.45 | 0.40 |
| Skimmed milk powder | 1.50 | 2.20 | 1.25 |

-continued

| Ingredient | A in wt. % | B in wt. % | C in wt. % |
|---|---|---|---|
| Maltose syrup (DE 60) | 1.25 | 1.20 | 1.20 |
| Water | 5.60 | 7.00 | 6.50 |
| Lemon flavor oil | 0.30 | — | 0.25 |
| Chocolate flavor (spray-dried) | — | 2.00 | — |
| Cocoa powder (14 wt. % fat) | — | 2.00 | — |
| Phytosterol mixture* | — | 1.10 | — |
| Dried extract of Example 6 | 1.65 | — | — |
| Dried extract of Example 8 | — | 2.35 | — |
| Product D from Application Example F1 | — | — | 5.50 |

Phytosterol mixture* see Application Example F19

Manufacturing Procedure:

a) Allow the powdered sucrose, maltose syrup, skimmed milk powder and vegetable soft fat to run smooth in a Hobart laboratory kneader, b) Dissolve the ammonium bicarbonate with some of the water and add the remaining water to a) and mix briefly, c) Add the dried extract of Example 6 or 8, or product D from Application Example F1, respectively, and subsequently add the remaining ingredients and work to a smooth dough, d) Roll out the dough to a thickness of 2.8 mm with a rolling machine, if desired apply a pattern with a relief bar, and punch out in the desired shape. Finally bake at an oven temperature: 200° C.

Application Example F35

Plain Cake

| Ingredient | A in wt. % | B in wt. % | C in wt. % |
|---|---|---|---|
| Wheat flour (plain, type 405) | Ad 100 | Ad 100 | Ad 100 |
| Wheat starch | 4.90 | 9.90 | — |
| Potato flour | 7.09 | — | 9.00 |
| Butterfat | 14.90 | 15.00 | 14.90 |
| Powdered sucrose | 20.20 | 19.50 | 20.00 |
| Baking powder (raising agent) | 0.75 | 0.75 | 0.75 |
| Sodium chloride | 0.15 | 0.15 | 0.15 |
| Egg yolk powder | 1.80 | 1.80 | 1.80 |
| Eggs | 17.00 | 17.00 | 16.00 |
| Emulsifier (mono-and diglycerides) | 1.40 | 1.40 | 1.40 |
| Phytosterol mixture* | — | 0.80 | — |
| Beta-carotene (0.5% solution in sunflower oil) | 1.40 | — | 0.50 |
| Water | 13.50 | 13.00 | 13.50 |
| Lemon flavor oil | 0.30 | — | 0.60 |
| Vanilla flavor A (spray-dried) | 0.50 | 2.00 | 0.10 |
| Dried extract of Example 6 | 1.95 | — | — |
| Dried extract of Example 8 | — | 2.85 | — |
| Product D from Application Example F1 | — | — | 6.50 |

Phytosterol mixture* see Application Example F26

Produce a dough according to a known procedure for cake dough making. Introduce the dough into a baking mould and bake at 180° C. for about 55 minutes.

Application Example F36

Margarine-Like Light Spread

| Ingredient | A | B | C | D | E |
|---|---|---|---|---|---|
| | in parts by weight | | | | |
| Light Spread* | 100 | 100 | 100 | 100 | 100 |
| Aqueous extract of Psyllium seed husks | — | 0.60 | — | — | 1.00 |
| Canola stanol esters* | — | — | — | 6.00 | — |
| Phytosterol mixture** | — | 5.00 | — | — | — |
| Dried extract of Example 6 | 3.90 | — | — | — | — |
| Dried extract of Example 7 | — | 5.35 | — | — | — |
| Dried extract of Example 8 | — | — | 6.25 | — | — |
| Euscaphic acid, tormentic acid and myrianthic acid (17:5:1) (w/w/w) | — | — | — | 2.85 | — |
| Product D from Application Example F1 | — | — | — | — | 13.40 |

Light Spread* a commercially available margarine-like light spread was used containing (per 100 g) a total of 38.7 wt. % of fats and fatty acids (including 4.8 wt. % saturated fats, 18.9 wt. % monounsaturated fats, 11.9 wt. % polyunsaturated fats, a total of 2187 mg of omega-3 fatty acids, a total of 9763 mg of omega-6 fatty acids), 5.7 wt. % of carbohydrates, 53.7 wt. % of water, 670 mg sodium, 4.0 mg potassium, 4.0 mg phosphorus, 4.0 mg calcium, 1.0 mg magnesium, 37.2 mg alpha-tocopherol, 13.8 mg gamma-tocopherol, 2.6 mg delta-tocopherol, 1370 µg retinol, and 56.5 µg vitamin K.
Canola stanol esters* see Application Example F19
Phytosterol mixture** see Application Example F26

Application Example F37

Orange Juice

| Ingredient | A | B | C | D | E |
|---|---|---|---|---|---|
| | in parts by weight | | | | |
| Orange juice* | 100 | 100 | 100 | 100 | 100 |
| Aqueous extract of Psyllium seed husks | 0.60 | — | — | — | 1.00 |
| Phytosterol mixture** | — | 0.40 | — | 0.30 | 0.25 |
| Dried extract of Example 6 | 3.90 | — | — | — | — |
| Dried extract of Example 7 | — | 5.35 | — | — | — |
| Dried extract of Example 8 | — | — | 6.25 | — | — |
| Euscaphic acid, tormentic acid and myrianthic acid (10:3:1) (w/w/w) | — | — | — | 2.85 | — |
| Product D from Application Example F1 | — | — | — | — | 13.40 |

Orange juice* a commercially available ready-to-drink orange juice (from concentrate) was used containing (per 100 g) a total of 10.8 wt. % of carbohydrates (including 8.4 wt. % of sugars and 0.2 wt. % of dietary fibers), a total 0.1 wt. % of fats and fatty acids (including a total of 3.0 mg of omega-3 fatty acids, a total of 9.0 mg of omega-6 fatty acids), a total 0.7 wt. % of proteins, 88.1 wt. % of water, 1.0 mg sodium, 0.1 µg selenium, 0.1 mg zinc, 0.1 mg iron, 190.0 mg potassium, 16.0 mg phosphorus, 9.0 mg calcium, 10.0 mg magnesium, 58.2 µg fluoride, 5.6 mg choline, 0.2 mg pantothenic acid, 44 µg folate (vitamin B9), 0.2 mg niacin, 0.1 mg thiamin, 0.2 mg alpha-tocopherol, 38.9 mg vitamin C, 32.1 µg retinol, and 0.1 µg vitamin K.
Phytosterol mixture** see Application Example F26

Application Example F38

Spreads

A commercially available spread was purchased containing a total of 55 wt % of vegetable oils (liquid canola oil, partially hydrogenated soybean oil, soybean oil, and hydrogenated soybean oil), water, plant stanol esters, salt, emulsifier (vegetable mono- and diglycerides, soy lecithin, polyglycerol esters of fatty acids), potassium sorbate, citric acid, calcium disodium EDTA, natural and artificial flavor, dl-tocopheryl acetate, vitamin A palmitate, vitamin B6, vitamin B12, beta-carotene. Said spread contained a total 57.1 wt. % of fats and fatty acids (including 7.1% of saturated fats, 14.3% of polyunsaturated fats and 28.6% of monounsaturated fats), a total of 2.85 wt. % plant stanol esters, 785.0 mg sodium, no proteins, and no carbohydrates.

To 100 g of said spread were added with stirring 2.25 g of the dried extract of Example 6 and 0.42 g of alpha-linolenic acid.

To 100 g of the above-mentioned spread were added with stirring 2.80 g of the dried extract of Example 7.

To 100 g of the above-mentioned spread were added with stirring 3.50 g of the dried extract of Example 8 and 0.30 g of alpha-linolenic acid.

To 100 g of the above-mentioned spread were added with stirring 1.25 g of a mixture consisting of euscaphic acid, tormentic acid and myrianthic acid (10:3:1) (w/w/w).

Application Example F39

Margarine-Like Spreads

| Ingredient | A | B | C | D | E |
|---|---|---|---|---|---|
| | \multicolumn{5}{c}{in wt. %} | | | | |
| Rapeseed oil | Ad 100 | Ad 100 | Ad 100 | Ad 100 | Ad 100 |
| Partially hydrogenated soybean oil | 35.00 | 32.00 | 30.00 | 30.00 | 30.00 |
| Coconut oil | 5.00 | 5.00 | 3.00 | — | — |
| Canola stanol esters* | — | — | 5.00 | 8.00 | 12.00 |
| Dried extract of Example 6 | 4.90 | — | 1.60 | — | — |
| Euscaphic acid, tormentic acid and myrianthic acid (10:3:1) (w/w/w) | — | 3.60 | 1.50 | 3.85 | 2.50 |

Canola stanol esters* see Application Example F19

Application Example F40

Mayonnaise

| Ingredient | A | B | C | D | E |
|---|---|---|---|---|---|
| | \multicolumn{5}{c}{in wt. %} | | | | |
| Rapeseed oil | Ad 100 | Ad 100 | Ad 100 | Ad 100 | Ad 100 |
| Partially hydrogenated soybean oil | 35.00 | 32.00 | 30.00 | 30.00 | 25.00 |
| Coconut oil | 5.00 | 5.00 | 3.00 | — | — |
| Canola stanol esters* | — | — | 5.00 | 8.00 | 12.00 |
| Dried extract of Example 6 | 4.90 | — | 1.60 | — | — |
| Euscaphic acid, tormentic acid and myrianthic acid (10:3:1) (w/w/w) | — | 3.60 | 1.50 | 3.85 | 2.50 |

Canola stanol esters* see Application Example F19

The above indicated ingredients were mixed accordingly to give five different mixtures A-E. Then, five different margarines were produced according to a conventional method, each margarine containing 67 wt. % of the above-indicated mixtures A-E.

Application Example F41

Margarine-Like Low-Fat Spreads

| Ingredient | A | B | C | D | E |
|---|---|---|---|---|---|
| | \multicolumn{5}{c}{in wt. %} | | | | |
| Water | Ad 100 | Ad 100 | Ad 100 | Ad 100 | Ad 100 |
| Cream (36% butter fat) | 10.20 | 8.00 | 9.00 | 7.50 | 8.15 |
| Dry curd cottage cheese | 37.00 | 40.00 | 38.00 | 39.00 | 40.00 |
| Non-fat dry milk | 4.50 | — | 5.00 | — | — |
| Lactose | — | 2.50 | — | 2.50 | 2.60 |
| Paselli™ SA 2 maltodextrin | 3.00 | 4.00 | 1.50 | 3.50 | 2.00 |
| Milk protein isolate | 3.00 | 3.20 | — | 3.50 | — |
| Gelatin | 0.75 | 0.73 | 0.75 | 0.73 | 0.75 |
| Sodium chloride | 1.00 | 0.90 | 0.90 | 0.90 | 1.00 |
| Carboxymethyl cellulose | 0.30 | 0.29 | 0.30 | 0.31 | 0.30 |
| Guar gum | 0.15 | 0.14 | 0.15 | 0.14 | 0.15 |
| Locust bean gum | 0.036 | 0.03 | 0.036 | 0.03 | 0.036 |
| Beta-carotene (1% solution) | 0.05 | 0.04 | 0.06 | 0.06 | 0.05 |
| Butter flavor | 0.02 | 0.02 | — | 0.02 | 0.02 |
| Canola stanol esters* | — | — | 5.00 | 1.00 | 4.00 |
| Dried extract of Example 6 | 4.50 | — | 1.60 | 2.00 | — |
| Product D from Application Example F1 | — | — | — | — | 6.00 |
| Euscaphic acid, tormentic acid and myrianthic acid (10:3:1) (w/w/w) | — | 3.60 | 1.50 | 3.85 | — |

Canola stanol esters* see Application Example F19

The resulting spreads each contained less than 5 wt. % of fats. The pH-value of the resulting spreads was in the range of 5.1-5.4.

Application Example F42

Fat-Reduced Butter Spreads

| Ingredient | A | B | C | D | E |
|---|---|---|---|---|---|
| | \multicolumn{5}{c}{in wt. %} | | | | |
| Water | Ad 100 | Ad 100 | — | Ad 100 | Ad 100 |
| Fresh creamery butter* | 46.59 | 49.60 | 49.60 | 48.95 | 44.70 |
| Skimmed Milk | — | — | Ad 100 | — | 10.00 |
| Gelatin | 0.90 | 1.25 | 1.55 | 1.55 | 1.85 |
| Soy lecithin (native) | 0.15 | 0.20 | — | 0.20 | 0.25 |
| Mono- and diglycerides | 0.30 | 0.30 | — | — | 0.18 |
| Lactic acid | 0.13 | 0.13 | # | 0.13 | 0.13 |
| Sodium benzoate | 0.13 | 0.10 | 0.10 | 0.09 | 0.13 |
| Potassium sorbate | 0.13 | 0.14 | 0.13 | 0.09 | 0.10 |
| Sodium chloride | 0.40 | 0.58 | 0.20 | 0.75 | 1.00 |
| Beta-carotene (1% solution in vegetable oil) | 0.05 | 0.04 | 0.06 | 0.06 | 0.05 |
| Canola stanol esters** | — | — | 4.00 | — | 2.40 |
| Dried extract of Example 6 | 4.40 | — | 1.20 | 3.00 | — |
| Product D from Application Example F1 | — | — | 1.45 | — | 7.10 |
| Euscaphic acid and tormentic acid (13:4) (w/w) | — | 3.90 | 1.20 | 1.85 | — |

Fresh creamery butter* contained a total of 1.75 wt. % of sodium chloride
Canola stanol esters** see Application Example F19
: Lactic acid is added until a pH-value of 4.0 is reached
The pH-value of the resulting spreads A, B, D and E was about 4.2.

Application Example F43

Spreadable Margarines

| Ingredient | A | B | C | D | E |
|---|---|---|---|---|---|
| | | | in wt. % | | |
| Sunflower oil | Ad 100 | Ad 100 | Ad 100 | Ad 100 | Ad 100 |
| Corn oil | — | 5.00 | — | 10.87 | — |
| Olive oil | — | — | 5.00 | — | 6.00 |
| Micronized hardstock fat powder (comprising 47 wt. % of phytosterols)* | 6.10 | 5.60 | — | 5.45 | 4.90 |
| Micronized hardstock fat powder (comprising 54 wt. % of stanol esters)** | 3.30 | — | — | — | 2.25 |
| Native soy lecithin | 0.33 | 0.33 | 0.30 | — | — |
| Distilled saturated mono- and diglyceride (>90% monoglyceride) | 0.20 | 0.35 | 0.33 | — | — |
| Beta-carotene (0.4% solution in sunflower oil) | 0.15 | 0.10 | 0.13 | 0.15 | 0.16 |
| Dried extract of Example 6 | 4.90 | — | 1.60 | — | 3.80 |
| Dried extract of Example 8 | — | 3.00 | — | — | — |
| Euscaphic acid, tormentic acid and myrianthic acid (10:3:1) (w/w/w) | — | — | 1.50 | 2.65 | — |
| Water | 29.65 | 63.60 | 60.00 | 58.00 | 57.00 |
| Modifiied waxy maize starch (distarch phosphate, E-number E1412) | — | — | — | 1.00 | 1.10 |
| Potassium sorbate | 0.08 | 0.11 | 0.07 | 0.05 | 0.08 |
| Sodium benzoate | — | — | 0.06 | 0.05 | — |
| Sodium chloride | 0.30 | 0.28 | 0.30 | 0.50 | 0.45 |

Micronized fat powder (comprising 47 wt. % of phytosterols)* Hardstock fat prepared as described in example 1 of EP 0 089 082 was micronized. The resulting powder was mixed with an appropriate amount of the phytosterol mixture described in Application Example F26.
Micronized hardstock fat powder (comprising 54 wt. % of stanol esters)** Hardstock fat prepared as described in example 1 of EP 0 089 082 was micronized. The resulting powder was mixed with an appropriate amount of the canola stanol esters described in Application Example F19.

The invention claimed is:

1. A method for reducing the HMG-CoA reductase activity in a patient in need thereof, comprising administering to said patient a pharmaceutically or nutraceutically effective total amount of a composition comprising a solvent based-plant extract containing:
   an amount of euscaphic acid,
   an amount of tormentic acid, and
   a total amount of 0 to 10 wt. % of organic solvents, based on the total weight of the composition,
   wherein the amount of euscaphic acid and tormentic acid is in a ratio ranging from 4:1 to 5:1.

2. The method according to claim 1 wherein the step of administering is effective in treating a disease involving a metabolic disorder.

3. The method according to claim 1, wherein the composition administered additionally includes quercetin.

4. The method according to claim 3, wherein the composition administered includes quercetin in a total amount of from 0.25 to 20 wt. %.

5. A method for reducing the HMG-CoA reductase activity in a patient in need thereof, comprising administering to said patient a pharmaceutically or nutraceutically effective total amount of a composition comprising a solvent-based plant extract derived from a plant selected from the group consisting of *Amelanchier alnifolia, Amelanchier arborea, Amelanchier asiatica, Amelanchier bartramiana, Amelanchier basalticola, Amelanchier canadensis, Amelanchier confusa, Amelanchier denticulata, Amelanchier fernaldii, Amelanchier humilis, Amelanchier interior, Amelanchier laevis, Amelanchier lamarckii, Amelanchier nantucketensis, Amelanchier obovalis, Amelanchier ovalis, Amelanchier pallida, Amelanchier pumila, Amelanchier sanquinea, Amelanchier sinica, Amelanchier spicata, Amelanchier stolonifera,* and *Amelanchier utahensis,* and containing:
   an amount of euscaphic acid,
   an amount of tormentic acid, and
   a total amount of 0 to 10 wt. % of organic solvents, based on the total weight of the composition,
   wherein the amount of euscaphic acid and tormentic acid is in a ratio ranging from 2:1 to 8:1.

6. The method according to claim 5 wherein the step of administering is effective in treating a disease involving a metabolic disorder.

7. The method according to claim 5, wherein the composition administered additionally includes quercetin.

8. The method according to claim 7, wherein the composition administered includes quercetin in a total amount of from 0.25 to 20 wt. %.

* * * * *